United States Patent [19]

Vick et al.

[11] 4,124,894
[45] Nov. 7, 1978

[54] APPARATUS AND METHOD FOR REPORTING DETECTED ERROR IN A CARDIAC SIGNAL

[75] Inventors: Howard A. Vick, Pearland; Donald B. Johnson, Houston, both of Tex.

[73] Assignee: Hycel, Inc., Houston, Tex.

[21] Appl. No.: 791,557

[22] Filed: Apr. 27, 1977

Related U.S. Application Data

[63] Continuation of Ser. No. 515,106, Oct. 15, 1974, abandoned.

[51] Int. Cl.² .................. G06F 15/42; A61B 5/04
[52] U.S. Cl. .................. 364/417; 128/2.06 A; 364/550
[58] Field of Search ............ 364/300, 417, 550; 128/2.06 A, 2.06 G

[56] References Cited

U.S. PATENT DOCUMENTS

| 3,799,148 | 3/1974 | Rowen | 128/2.06 A |
| 3,807,392 | 4/1974 | Harris | 128/2.06 A |
| 3,885,456 | 12/1974 | Summers et al. | 235/151.3 |
| 4,006,737 | 2/1977 | Cherry | 128/2.06 G |

OTHER PUBLICATIONS

Hill: Monitoring of Surgical Patients by Digital Computer, Medical Engineering, Year Book Medical Publ., Chicago, pp. 374-384.
Bonner: Two-mode ECG Monitoring System Defensive Publication T 916.007, Nov. 1973.

*Primary Examiner*—Felix D. Gruber
*Attorney, Agent, or Firm*—Robert P. Cogan

[57] ABSTRACT

A system for simultaneously monitoring one or a plurality of patients samples each electrocardiac waveform of each patient to generate a model waveform for each patient. The image is resolved into contour intervals, e.g. PR, QR, ST and T intervals, and the system establishes a set of interval limits for each patient to which samples of subsequently monitored waveforms are compared. Errors associated with each patient are separately stored and reported by the system in an order which may correspond to a priority ranking of the seriousness of the conditions with which the errors are associated.

6 Claims, 30 Drawing Figures

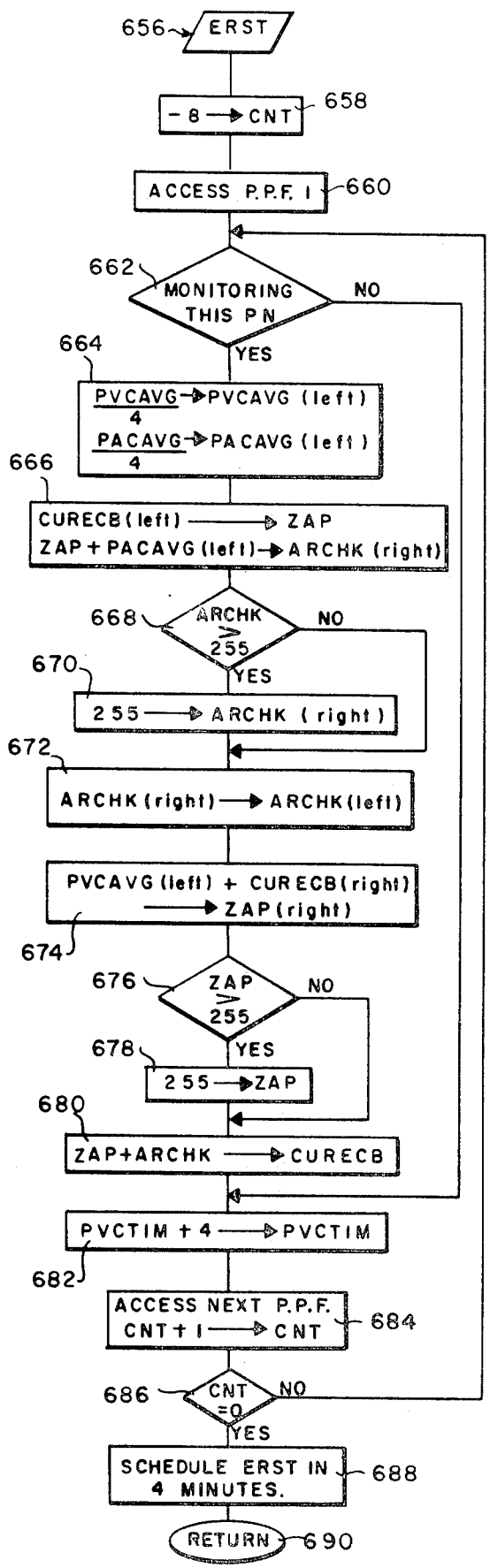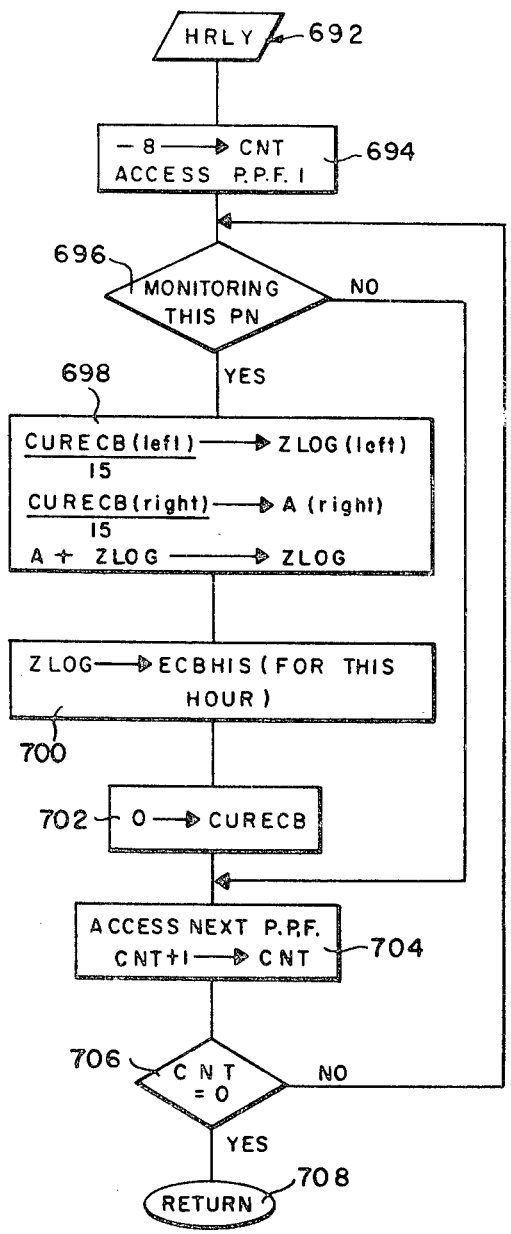
FIG. 14.
FIG. 15.

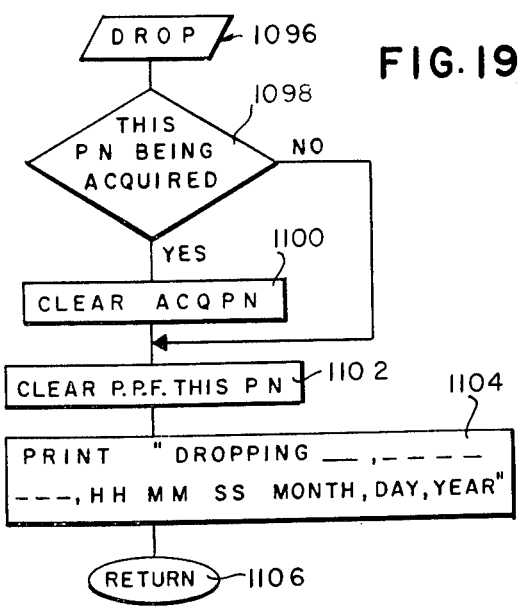
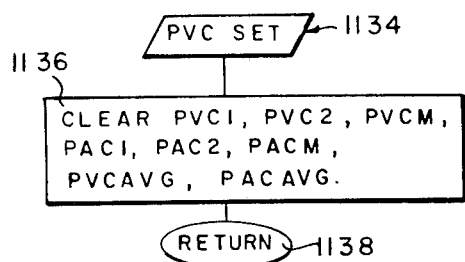
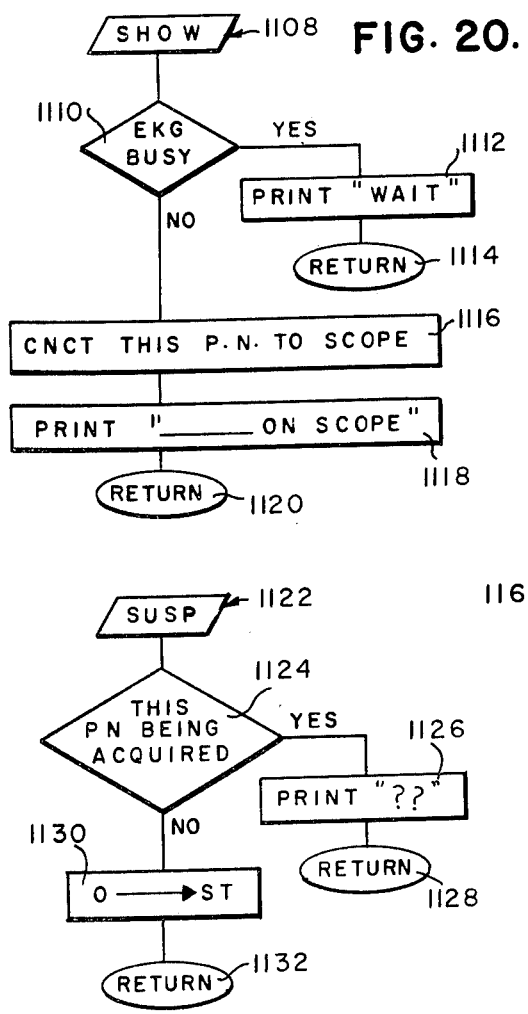
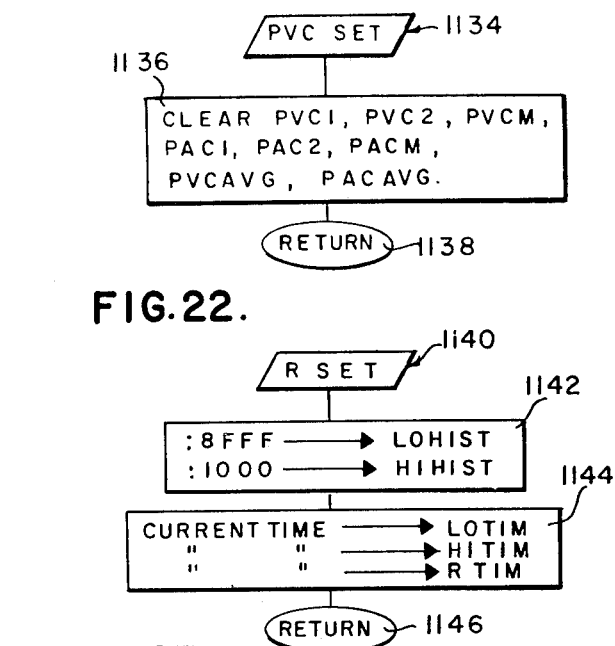
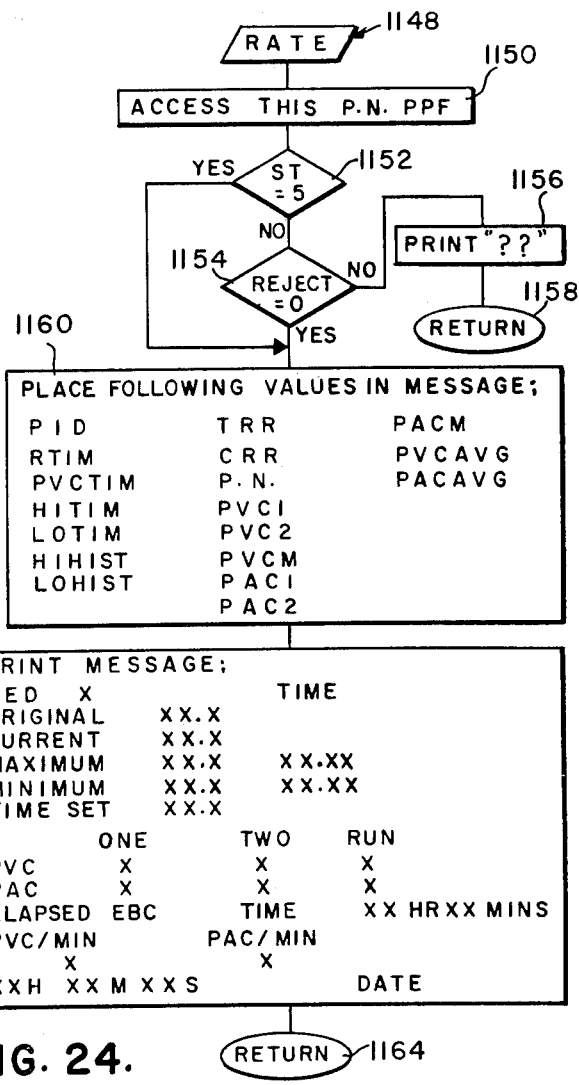

APPARATUS AND METHOD FOR REPORTING DETECTED ERROR IN A CARDIAC SIGNAL

This is a continuation of application Ser. No. 515,106 filed on Oct. 15, 1974, and now abandoned.

This invention relates to a system and method for monitoring an electric signal, and more particularly, to a system and method utilizing a digital computer that is programed to acquire a master image of one beat of a particular patient's electrocardiac signal and then to compare subsequent beats against that master image, and to provide an error message whenever specific events or changes occur in the electrocardiac signal.

After a person has suffered a heart attack or has encountered other cardiac problems, he remains very susceptible to subsequent heart problems. These problems do not occur instantaneously or over just a few heartbeats; rather there is a continuous occurring degeneration of the heart which is indicated by a changing heartbeat pattern, as manifested by an electrocardiac signal. If one could monitor the electrocardiac signal, it would be possible to provide a warning message whenever the shape of the electrocardiac signal changed by more than preset limits. It also is desirable to detect the occurrence of ectopic beats, such as premature ventricular contractions (PVC) and premature atrial contractions (PAC) and provide warning messages concerning these events in certain situations. Further, it is desirable to detect and report the occurrence of any cessation of the electrocardiac signal. In any of these situations, a physician can take corrective action to prevent death or an actual heart attack or other heart problem.

The electrocardiac signal from any particular patient is unique to the patient. Although medical textbooks show an ideal electrocardiac signal, most people, and especially people in need of cardiac monitoring, do not have the ideal signal; rather, they have a signal unique to themselves. Normally, as long as this signal maintains a constant repetitious shape, no impending problems are likely to occur. However, when this signal changes shape, an indication of a problem may be manifested. Thus, it is desirable to compare a presently occurring patient's electrocardiac signal against an established standard previously taken from that same patient to determine any change of shape.

Prior art methods of doing this have utilized sample and hold circuits where a voltage is held in a capacitor and continually updated. The problem with these methods is that they merely monitor changes in the area beneath a small portion of each beat, known as the QRS complex. This provides insufficient information because (1) the area may remain constant while the shape changes and (2) changes outside the QRS complex are not discovered. Other methods have utilized either analog or digital techniques to merely measure the rate of a person's heartbeat or area beneath the electrocardiac signal. Still other methods compare each signal to previously established norms rather than against the patient's own stored signal. Although these methods all provide useful information, they do not indicate that the shape of the signal has changed relative to the patient's own previously occurring signal.

In accordance with a preferred embodiment of this invention, there is provided a method in a cardiac monitoring system having processing means for receiving sample values from a cyclic electrocardiac signal and processing those sampled values to store a morphological image of a determined interval duration surrounding determinable one of the sampled values. The image is derived from initial cycles of the signal. The processing means then compares determined intervals subsequent cycles of the signal with the stored image indicates whether a morphological change on the stored image has occurred in any of a plurality of portion on each subsequent cycle. Further, the processing means stores an average cycle time relating to the average time between determinable sample values during a given number of lastly occurring determined intervals. The method of operating the processing means to detect an ectopic beat during a recently occurring determined interval includes the steps of determining whether the time between determinable sample values and the recently occurring determined interval and a determined interval immediately preceding the recently occurring determined interval is less than a certain percentage of the stored average cycle time and determining whether a morphological change has occurred in more than one of the plurality of portion of the recently occurring determined interval.

A detailed description of this invention is hereinafter given with reference being made to the following drawings, in which:

FIG. 14 is a flow diagram of the ERST program performed every four minutes to accumulate ectopic beat history data for each patient being monitored;

FIG. 15 is a flow diagram of the HRLY program performed on the hour to store ectopic beat history data for each patient being monitored;

FIG. 19 is a flow diagram of the DROP program performed in response to a depression of the DROP key on the keyboard shown in FIG. 1;

FIG. 20 is a flow diagram of the SHOW program used to connect a patient's electrocardiac signal to the cardioscope shown in FIG. 1 in response to the depression of the SHOW key on the keyboard shown FIG. 1;

FIG. 21 is a flow diagram of the SUSP program which is performed in response to the depression of the SUSP key on the keyboard shown in FIG. 1;

FIG. 22 is a flow diagram of the PVCSET program used to clear the ectopic beat history stored in the memory of the computer and performed in response to the depression of a ECT RSET key on the keyboard shown in FIG. 1;

Figure 1:
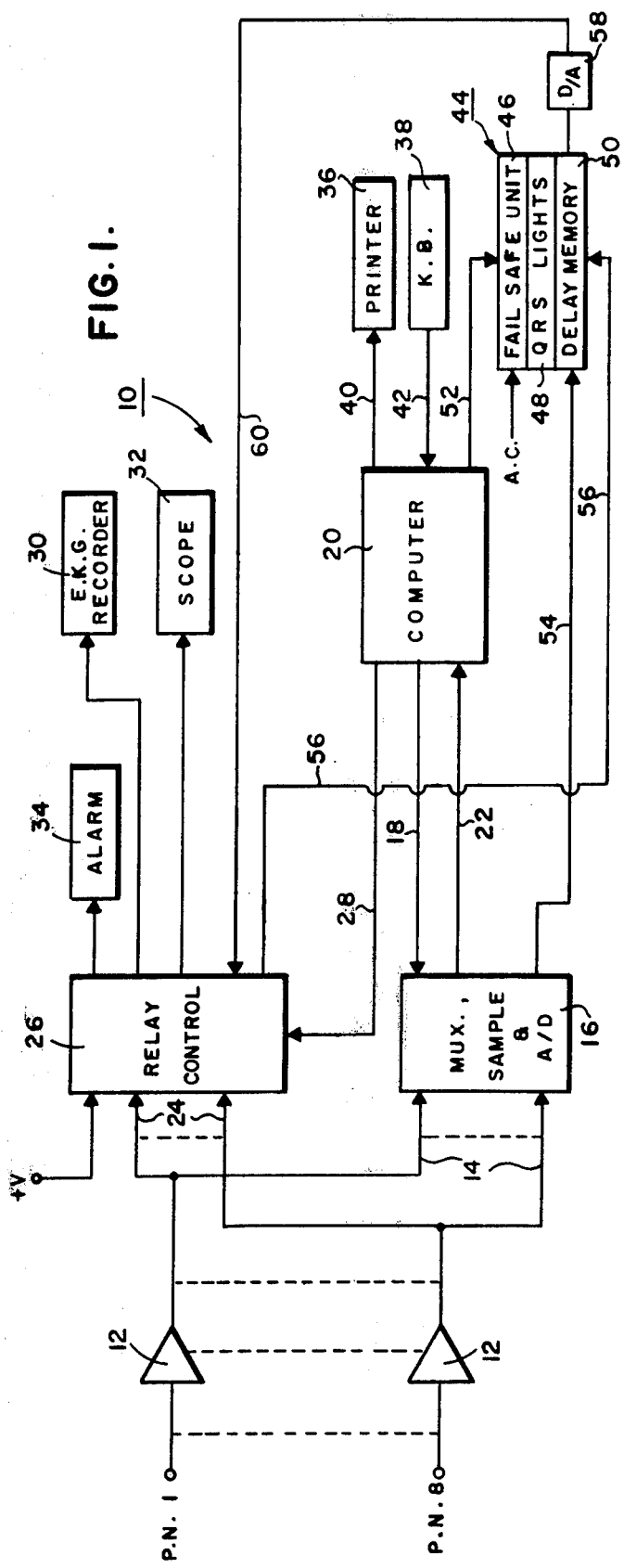
FIG. 1 is a block diagram of the apparatus of this invention.

FIG. 23 is a flow diagram of the RSET program which clears the rate history information stored in the memory of the computer and is performed in response to a depression of a RHST RSET key on the keyboard shown in FIG. 1; and FIG. 24 is a flow diagram of a computer program RATE which prints information concerning the rate history and ectopic beat history of a particular patient in response to the depression of a RATE HIST key on the keyboard shown in FIG. 1.

Referring now to FIG. 1, a block diagram of the cardiac monitoring system 10 of this invention is shown. System 10 is arranged to monitor up to eight different patients electrocardiac signals respectively designated as PN1 through PN8. Each of the patients to be monitored is connected with three electrodes in the conventional manner to provide an electrocardiac signal to a different one of the eight cardiac amplifiers 12. The output from each of cardiac amplifiers 12 is a signal similar to the signal shown in FIG. 2, which signal will be described in more detail hereafter. The outputs from each of eight amplifiers 12 is provided over lines 14 to a multiplexer, sampler, and analog-to-digital converter circuit 16. Circuit 16 samples the analog value of each of the signals from the eight amplifiers 12, one at a time, 120 times a second and converts each sampled value to an eight bit digital value. Circuit 16 stores each sampled value until such time as a signal on line 18 from computer 20 is applied thereto, at which time, circuit 16 provides one of the sampled values over lines 22 to computer 20. Line 22, in practice, is eight separate lines to allow the eight bits of each sample value to be applied to computer 20 in parallel. Computer 20 controls circuit 16 so that eight sample values, one of from each of the eight amplifier 12 signals, are provided to computer 20 once each 1/20th of a second. Computer 20 may be Alpha 16 computer, manufactured and sold commercially by Computer Automation, Inc. of Newport Beach, Calif. A block diagram of the Alpha 16 computer is shown in FIG. 3, which block diagram and the programing thereof is described in the book entitled *Alpha 16 and Naked Mini 16 Computer Reference Manual*, January, 1972, published by Computer Automation, Inc.

The output from each of amplifiers 12 is also applied over lines 24 to relay control circuit 26, which may be a set of relays that are opened or closed by signals on line 28 applied to circuit 26 from computer 20. The relays of circuit 26 are arranged to transmit the same or a different selected one of the signals from amplifiers 12 to the electrocardiograph (EKG) strip chart recorder 30 or the electrocardioscope 32, which respectively provide a permanent graphic representation of the selected patient's electrocardiac signal (stip record) and a display of the patient's electrocardiac signal on a cathode ray tube. The signals applied to circuit 26 from computer 20 are applied through line 28 and circuit 26 to alarm 34. Alarm 34 may be any known transducer device, which in response to a D.C. signal, sounds audible alarm.

A printer 36 and a keyboard 38 are also connected to computer 20. Printer 36 responds to ASCII coded signals applied to line 40 from computer 20 to print desired alpha-numeric messages. Keyboard 38 may be any standard keyboard inputting device which transmits digital data to a computer in response to an operator initiated depression of a key. The keyboard may have key locations similar to those found on a standard typewriter; however each key which normally defines a letter, will instead define a particular function to be performed. In addition, there will also be provided keys corresponding to the number 0 through 9, as well as keys for a comma, a period and a backward slash and a key entitled ENTER. Printer 36 and keyboard 38 may be a single unit available in commerce, such as the Silent 700 Printer manufactured by Texas Instruments, Inc. The various function keys on keyboard 38 and the manner of using them are set out below:

1. ACQ — A depression of this key followed by the depression of a number key 1 through 8 and then a depression of the ENTER key, causes a patient to be acquired if previously disconnected, reacquired if previously acquired or reconnected if previously suspended.

2. DROP: A depression of this key followed by a depression of a number key 1 through 8 and the ENTER key causes the patient defined by the depressed number key previously acquired to be disconnected from the system.

3. RATE HIST: A depression of this key, followed by the depression of a number key 1 through 8 and the ENTER key causes printer 36 to print the rate history and ectopic beat history of a particular patient having the number key depressed.

4. STRIP: A depression of this key followed by a depression of a number key 1 through 8 and the ENTER key causes EKG recorder 30 to provide a continuous strip record of the electrocardiac signal of the particular patient defined by the depressed number key to be provided by EKG recorder 30. If EKG recorder 30 is already providing a strip record of a particular patient, it is merely necessary to depress the STRIP key, followed by the ENTER key and EKG recorder 30 will continue providing the strip record beyond the normal 8.3 second time.

5. EKG OFF: A depression of this key followed by ENTER causes a EKG recorder 30 to stop providing a strip record.

6. SHOW: A depression of this key, followed by the depression of a number key 1 through 8 and the ENTER key connects the electrocardiac signal of the particular patient defined by the depressed number key to cardioscope 32. Printer 36 will respond to the depression of this key by printing "_____ON SCOPE" when the blank is the particular patient's number.

7. RSHT RSET: A depression of this key, followed by the depression of a number key 1 through 8 and the ENTER key causes the rate history information stored by computer 20 for the particular patient defined by the depressed number key to be erased from the memory thereof. Thereafter, computer 20 will store new rate history information for that patient.

8. SUSP: A depression of this key, followed by a depression of a number key 1 through 8 and the ENTER key causes the previously acquired patient defined by the depressed number key to be suspended from monitoring without the erasure from memory of any of the acquired or stored information. A depression of the ACQ key followed by the number key and the ENTER key after the suspension period has passed will cause the monitoring to resume from the point previously left off.

9. STAT: A depression of this key followed by the ENTER key will cause printer 36 to print a message showing the status of each of the patient numbers. The status may be either monitoring, acquiring, suspended, alarm occurring, or disconnected. The message also shows which patient number signal is on cardioscope 32.

10. MEM STRP: A depression of this key followed by the depression on a number key 1 through 8 and the ENTER key causes EKG recorder 30 to provide an 8.3 second strip record showing the previous 8.3 second of electrocardiac signal activity for the patient defined by the depressed number key.

11. TONE OFF: A depression of this key followed by a depression of a number key 1 through 8 and the ENTER key causes the audible alarm from alarm 34 to be turned off.

12. DATE SET: A depression of this key followed by a depression of the number keys and the comma key formated as MM,DD,YY, where M,D and Y respectively indicate the month, day and year, followed by the depression of the ENTER key will enter the date into the memory of the computer 20.

13. ALRM HIST: A depression of this key, followed by a depression of a key 1 through 8 and the ENTER key will cause printer 36 to print "ALARM HISTORY" followed by the last alarm message which was printed for the patient defined by the depressed number key.

14. EVNT HIST: A depression of this key, followed by the depression of a number key 1 through 8 and the ENTER key causes printer 36 to print a message defining in which beats morphological errors occurred during the last 16 beats for the patient defined by the depressed number key.

15. ALRM LIMTS: A depression of this key followed by a number key 1 through 8 and the ENTER key causes printer 36 to print a message indicating at what value the alarm limits are set for the patient defined by the depressed number key.

16. PR SET: A depression of this key followed by the depression of a numbered key 1 through 8, the comma key and two other number keys 0 through 9 and finally the ENTER key sets the alarm limits of the PR region for the patient defined by the first depressed number key.

17. QRS SET: A depression of this key followed by a depression of a number key 1 through 8, comma key, and two other number keys 0 through 9, followed by the ENTER key sets the alarm limits of the QRS region for the patient defined by the first depressed number key.

18. ST SET: A depression of this key, followed by a depression of a key 1 through 8, the comma key and two other number keys 0 through 9 followed by the ENTER key sets the alarm limits of the ST region for the patient defined by the first depressed number key.

19. T SET: A depression of this key, followed by a depression of a number key 1 through 8, the comma key, and two other number keys 0 through 9 followed by the ENTER key sets the alarm limits of the T region for the patient defined by the first depressed number key.

20. RT SET: A depression of this key, followed by a depression of a number key 1 through 8, the comma key, and two other number keys 0 through 9 and the ENTER key sets the alarm limits for the rate for the patient defined by the first depressed number key.

21. ECT RSET: A depression of this key, followed by the depression of a number key 1 through 8 and the ENTER key causes the computer to erase the ectopic beat history recorded therein for the patient defined by the depressed number key and to restart accumulating the information.

22. ECT TRND: The depression of this key, followed by a depression of a number key and the ENTER key causes printer 20 to print a sliding scale histogram, giving the most recent 24 hours of the ectopic beat trend history for the patient defined by the depressed number key.

23. CLOK SET: A depression of this key followed by the depression of four number keys 0 through 9 and the ENTER key sets the time in computer 20 to the time defined by the number keys HH MM where H and M refer to hours and minutes respectively.

24. TIME: A depression of this key causes printer 36 to print the time stored in computer 20.

Also connected to computer 20 is a unit 44, which includes failsafe unit 46, QRS lights unit 48 and delay memory 50. Failsafe unit 46 may be a monostable multivibrator which is normally set and which must be reset at a periodic rate of, for instance, every 5 seconds, to maintain it reset. If failsafe unit 46 is not reset within the 5 seconds limit, a signal will be applied to an alarm (not shown) included therein causing an audible alarm to sound. Failsafe unit 46 is reset each time computer 20 is triggered to a supply a reset signal from a register therein which reset signal is applied on line 52 to unit 44.

QRS lights unit 48 is a series of eight lights, each of which is assigned to one of the eight patients capable of being monitored. Each time complexism of QRS is computed for a particular one of the patients being monitored is detected by computer 20, the light in QRS light unit 48 associated with that one patient is turned on. Each light in QRS lights unit 48 is turned on in response to a signal on line 52 unique to that particular light.

Delay memory 50 is a series of eight, 1,024 word by six bit, shift registers, each of which is responsive to the six most significant bits of the eight bit digit sample values from a respective one of the eight electrocardiac signals PN1 through PN8, which values are provided over line 54 from circuit 16. In actual practice line 54 may be 48 individual lines, each of which carries one of the six bits of each of the eight sample values. Delay memory 50 is responsive to an internal clock so that each 1/120th of a second, the six bits of the word previously applied thereto are shifted one position and a new word is then inserted in the shift registers. When the six bits representing a sample value are then shifted, six previous most significant bits are lost. Since each shift register is 1024 words by six bits each sample value is stored for 8.3 seconds after the six bits representing that value are first applied to the input of delay memory 50.

Delay memory 50 is responsive to control signal from computer 20 applied to unit 44 over line 52. Delay memory 50 is further responsive to a signal appearing on line 56 from relay control circuit 26. The signal on line 56 is unigue to one of the eight shift registers in delay memory 50 and is caused by a signal from computer 20 over line 28 through relay control circuit 26 to line 56. Upon proper command of the signal on line 56, the output of one of the eight shift registers included in delay memory 50 may be coupled through a digital-to-analog converter circuit 58 and an analog signal from there is applied over line 60 to relay control. The signal on line 60, in turn, will be coupled through a proper relay in relay control circuit 26 to EKG recorder 30, so that EKG recorder 30 provides a strip record of the electrocardiac signal during the preceding 8.3 seconds. This is necessary because under normal usage, a strip record will be provided each time an error is detected, and it is preferable to record the event preceding the error detection rather than the event succeeding the error detection.

Figure 2:
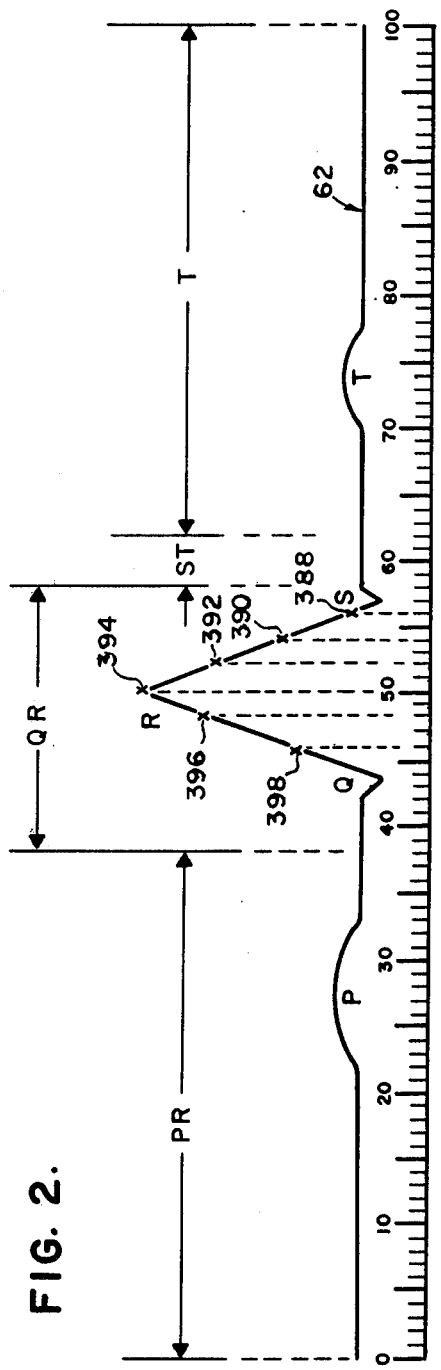
FIG. 2 is a graphical representation of an electrocardiac signal showing the points at which the signal is sampled by the apparatus of FIG. 1.
Figure 3:
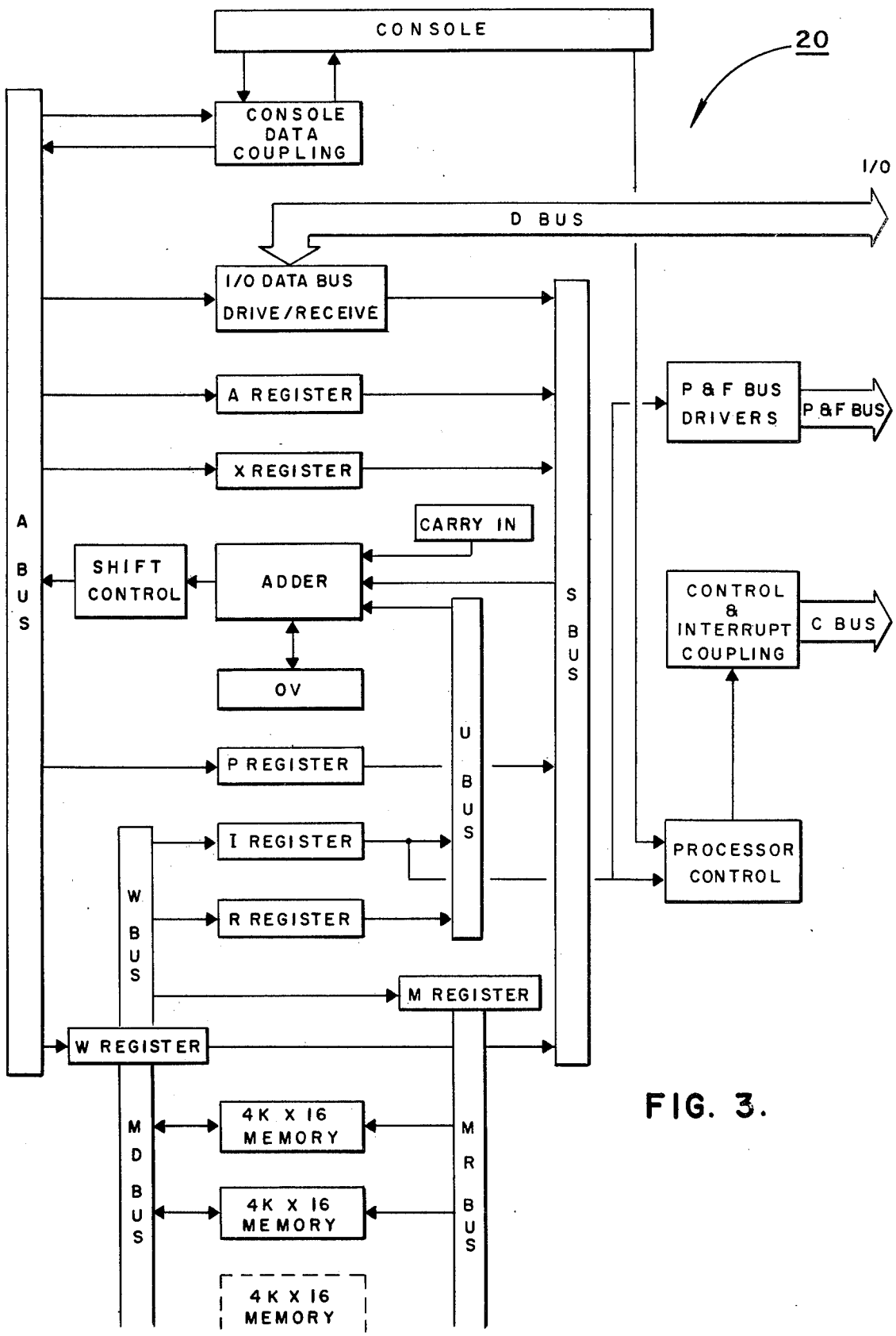
FIG. 3 is a block diagram of a computer usable in the apparatus shown by FIG. 1.

Referring now to FIG. 2, one heartbeat cycle of a substantially normal electrocardiac wave 62 is shown. Electrocardiac wave 62 includes five individual waves respectively labeled P,Q,R,S and T. For purposes of illustration in this description, wave 62 is assumed to constitute one complete cycle of patient's heartbeat, and has a duration of 5/6 of a second, which corresponds to a heartbeat rate of 72 beats per minute. In practice, the duration of one cycle may vary greatly over this assumed time, although for a normal person, the shape of the electrocardiac waveform will be similar to that shown by wave 62. The amplitude of wave 62 is adjusted by amplifiers 12 to be within certain limits and then sampled by circuit 16 at a rate of 120 times per second. Directly beneath wave 62 are 100 vertical lines, with every tenth line being numbered. Each of these lines indicates a point at which wave 62 is sampled by circuit 16, and is hereinafter called a sample time. After sampling, the analog value sampled is converted to a digital sample value and stored until it is requested to be sent to computer 20, When comparing wave 62 with a previously established wave from the patient in order to note changes in the shape of wave 62, it is desirable to know in which area of the wave the change occurred. For this reason, wave 62 is divided into four sub-intervals which are respectively labeled the PR, QR, ST and T contour intervals. The QR interval will always be 1/6th of a second, or twenty sample times, in duration and the ST interval will always be 1/30th of a second, or four sample times, in duration. The QR and ST intervals constitute the QRS complex, which is the area between the Q and S waves of wave 62. The PR and T intervals will each be equal and will constitute the remaining portion of wave 62. In the example of FIG. 2, the duration of each of the PR and T waves is 38 sample times or 19/60th of a second. However, as the duration of each of individual cycle increases or decreases, over that shown in FIG. 2, each of the corresponding PR and T subintervals will increase or decrease by one half the amount of the total increase or decrease.

Before referring to the flow diagrams in FIGS. 4–24 the organization of the working memory and patient parameter file (P.P.F.) portion of the memory of computer 20 should be understood. The memory organization of computer 20 is divided into areas containing an executive program, a plurality of applications programs, and the working memory and P.P.F.s. The executive and applications program include computer instructions and may include certain areas for temporary storage used in executing those programs. Following the executive and application programs, there is a working memory and eight P.P.F.s, one for each patient capable of being monitored. Block diagrams of the major application programs are shown in FIGS. 4 through 24 and the organization of the working memory and P.P.F.s are shown in TABLE I. As used with regard to the memory organization, the term "word" means a location in the memory of computer 20 capable of storing a given number of bits of information, for example, sixteen, and the byte means a portion of a word, for example eight bits. A bit is a binary digit which may be either 0 or 1.

TABLE I

| NAME | WORKING MEMORY DESCRIPTION | #WORDS |
|---|---|---|
| WBA | WORK BUFFER | 120 |
| CMBA | CUMULATION BUFFER | 120 |

| | PATIENT PARAMETER FILE ONE (P.P.F.1) | |
|---|---|---|
| DB | New Data Buffer (In Bytes) | 72 |
| MI | Master Image Buffer (In Bytes) | 60 |
| F1–F6 | Autocorrelation Mask | 6 |
| D0–D10 | Last 11 Values | 11 |
| ST | Status | 1 |
| PACF | Previous Autocorrelation Value | 1 |
| THR | Threshold Autocorrelation Value | 1 |
| PRP | Absolute Time Last QRS Detected (In ACQ Counts) | 1 |
| CRR | Time (In ACQ Counts) of Last R-R Interval | 1 |
| TRR | Average R-R Interval (In ACQ Counts) During Acquisition | 1 |
| CPYFLG | Countdown Timer | 1 |
| NUL | Countdown Timer | 1 |
| RPTR | Pointer to Next 18 Locations Where Last 18 R-R Times (In ACQ Counts) Are Stored | 19 |
| RHYTHM | Rhythm of Heartbeat | 1 |
| PQ | | 1 |
| QQ | | 1 |
| SQ | Error Status Words - Contain Error History For Each Contour | 1 |
| TQ | Interval Rate and Rhythm During the Last 16 Beats | 1 |
| RQ | | 1 |
| RTHQ | | 1 |
| EVC | Event Counter | 1 |
| PLIM | | 1 |
| QLIM | Limit Table | 1 |
| SLIM | 1 | |
| TLIM | | 1 |

-continued

| PATIENT PARAMETER FILE ONE (P.P.F.1) | | |
|---|---|---|
| HIHIST | Maximum R R Value Since Acquisition or RHST RSET | 1 |
| LOHIST | Minimum R R Value Since Acquisition or RHST RSET | 1 |
| RTM | Time Rate Last Set (During ACQ or RHST RSET | 1 |
| LOTIM | Time of Lowest Rate | 1 |
| HITIM | Time of Highest Rate | 1 |
| ATIM | Time of Last Alarm | 1 |
| PID | Patient ID Number | 1 |
| ARAT | Rate of Last Alarm Time | 1 |
| REJECT | Set To: −1 When Clearing PPF; 0 When ACQ Key is Depressed | 1 |
| PVC1 | Single PVC | 1 |
| PVC2 | Double PVC | 1 |
| PVCM | Run of PVC — Bit 15: Indicator of Current Status | 1 |
| PAC1 | Single PAC — Bits 0-14: Cumulative Count Since CNCT or | 1 |
| PAC2 | Double PAC — ECT RSET | 1 |
| PACM | Run of PAC | 1 |
| PVCAVG | Right Half: #PVC During Last 4 Minutes Left Half: #PVC/MIN During Last 4 Minutes | 1 |
| PACAVG | Right Half: #PAC During Last 4 Minutes Left Half: #PAC/MIN During Last 4 Minutes | 1 |
| EXTRA | When Set to 1, Inhibits Error From Being Called by ARCHK for 60 Sec. | 1 |
| PVCTIM | Time Counting PVC (In Minutes) | 1 |
| PRR | Previous R-R Interval (In ACQ Counts) | 1 |
| PQS | PQ Saved | 1 |
| QQS | QQ Saved | 1 |
| SQS | SQ Saved — Snapshot When Execute Error | 1 |
| TQS | TQ Saved | 1 |
| RQS | RQ Saved | 1 |
| RTHQS | RTHQ Saved | |
| PLM | P Region Error Limit Value | 1 |
| QLM | QRS Region Error Limit Value | 1 |
| SLM | ST Region Error Limit Value | 1 |
| TLM | T Region Error Limit Value | 1 |
| RLM | Rate Error Limit Value | 1 |
| RTHLM | Rhythm Error Limit Value | 1 |
| ALMIN | Alarm Inhibit Flag | 1 |
| ALARM | Parameter Error Word | 1 |
| ECBHIS | Ectopic Beat History Table For the Last 24 Hours | 24 |
| CUREGB | Right Half: PVC This Hour Left Half: PAC This Hour | 1 |
| EOB | End of P.P.F.1 | 1 |

The working memory which in Table I includes a single work buffer portion (WB) consisting of 120 words and a single cumulation buffer portion (CB) consisting of 120 words. As will be explained in more detail hereafter, these buffers are used in acquiring the master image of each patient's cardiac signal, and since this occurs for only one patient at a time, the work buffer and cumulation buffer may be shared by all patients. In addition to the work and cumulation buffers, there is a patient parameter file (P.P.F.) for each of the eight patients capable of being monitored.

Each P.P.F. is assigned to a patient and used to store data relating to only that patient. Each P.P.F. includes: a data buffer (DB) in which the most recent 144 sample values, in byte form, are stored; a master image store (MI) of 60 words in which a master image derived during acquisition, is stored, which master image may include up to 120 bytes of information; a six for F file in which the autocorrelation mask derived during acquisition is stored; and an updatable eleven word file in which the most recent 11 sample values are stored with the most recent sample value being in word D0 and the eleventh most recent sample value being word D10.

Further, there is included single word character for: status (ST) in which a number from 0 through 5, inclusive, may be stored indicating whether a particular patient signal is disconnected, in various phases of being acquired or being monitored; a previous autocorrelation value (PACF); a threshold autocorrelation value (THR); the real time the last QRS complex was detected (PRP) as a number related to cumulative ACQ programed performances or ACQ counts; the time in ACQ counts of the interval between successive detected R waves R-R interval for the most reagent R-R interval (CRR); and the average time of an R-R interval in ACQ count during acquisition (PRR). In addition, a part of countdown timers (PYFLG and NVL) are provided as single word location.

There is also provided a signal pointer followed by an 18 word rotating file in which the pointer points to a particular location in the file and the file contains the time, in ACQ counts, of the last 18 R-R intervals. In addition, there is provided a location for storing a valve related to the rhythm of the heartbeat (RHYTHM), and six error status words (PQ, QQ, SQ, TQ, RQ and RTHQ), each of which contains the error history during the last 16 beats for the four contour intervals, the rate and the rhythm.

There is also provided an event counter (EVC) location which is incremented each time a QRS complex is detected and which is reset to 0 at a periodic rate of, for example, every 3 seconds. This word is used to determine whether a lost EKG situation has occurred. In addition, there is provided a limit table of four words (PLIM, QLIM, SLIM and TLIM) in which tolerance limits derived during acquisition for a particular waveform are stored and against which later cumulative differences for each of the four contour intervals are compared against. Further, there are provided a pair of words (HIHIST and LOHIST) for storing the maximum and minimum R-R values in ACQ counts. These words are reset each time an acquisition occurs or whenever the RHST RSET key on keyboard 38 is depressed. There is also provided a word (RTIM) for storing the time at which the rate history stored in the HIHIST and LOHIST words was last reset, two words (LOTIM and HITIM) which respectively have stored therein the time at which the lowest rate and the highest rate occurred and a word (ATIM) for storing the time of the last alarm. Additionally, an identification number word of (PID) is used to store the patient ID number in binary format and a word (ARAT) is used to store the rate at the last alarm time. Further, a word (REJECT) is used as a flag for telling whether the P.P.F. for that patient has been cleared. Specifically, it is set to a minus value when the P.P.F. is cleared and is set to 0 when the ACQ key on keyboard 38 is depressed.

There is also provided three PVC cumulative counters and indicators PVC1, PVC2 and PVCM and three PAC cumulative counters and indictors PAC1, PAC2 and PACM each respectively counting the cumulative number of single, double and runs of PVCs and PACs and indicating the status of PVCs and PACs during the second most recent heartbeat. In each of these counters and indicators bit 15 indicates the status and bits from 0 to 14 constitutes the cumulative count since the time the ACQ key or the ECT RSET key of keyboard 38 has been depressed. In addition, two words (PVCAVG and PACAVG) are provided and in the right half of each, the respective number of PVCs or PACs occurring during the last 4 minutes are stored and in the left half of each, the respective number of PVCs per minute or PACs per minute during the last 4 minutes is stored.

Another word (EXTRA) is settable to provide an indication of the time from which an alarm is to be inhibited. A word (PVCTIM) is used to store the time in minutes that PVCs have been counted and a word (PRR) is used to store the time of the R-R interval in ACQ counts for the second most recent beat. Six words (PQS, QQS, SQS, TQS, RQS and RTHQS) are used to store the error status values shown by respective words PQ, QQ, SQ, TQ, RQ and RTHQ, at the time in alarm condition occurs. Five other words (PLM, QLM, SLM, TLM and RLM) are used to store the limit value which can be set by depressing the proper one of the PR SET, QRS SET, ST SET, TSET and RTSET keys on keyboard 38 and a sixth limit value word is for storing the error limits for rhythm.

A word ALMIN is used as an alarm inhibit flag and, whenever it is set, the alarm will be inhibited from being turned on under certain circumstances. Another word ALARM is used as a parameter error word in which the first five bits thereof will be set if a particular one of the four contour interval or the rate has caused an error condition to occur.

There is also provided a 24 word ectopic beat history table (ECBHIS), with each word thereof being associated with a particular hour during the past 24 hours. In each word of the ECBHIS table, the right half of the word stores the number of PVCs during the particular hour and the left half of the word stores a number of PACs during the hour. In addition, a word (CURCEB) is provided for storing the number of PVCs during this hour in the right half and the number of PACs during this hour in the left half. Finally, the P.P.F. has a word (EOB) which indicates the address of the end of that P.P.F.

Referring now to FIGS. 4 through 24, flow diagram of pertinent ones of the application programs for operating computer 20 in conjunction with the other apparatus of monitoring system 10 now be described. The execution sequence of these application programs are under the control of the executive program, which may be any known type executive that schedules various application programs to be performed either on (1) a priority interrupt basis (2) next in turn or (3) after a certain delay time. For instance, the executive will schedule without being requested, the application program which causes circuit 16 to sample each of the patient signals RN1 through PN8 once every 1/120th of a second by scheduling that program to be executed every 1/120th of a second on a priority basis. This program will be executed even if it is necessary to interrupt and later return to another program when being executed. Further, within a given applications program, a request may be made to the executive to schedule another applications program for execution in its proper turn after previously requested and scheduled applications programs have been executed. In addition, the executive can be requested to schedule an application program at a given time in the future, such as, in three seconds. The executive program is also responsive to interrupt signals from, for instance, the keyboard, which will cause certain application programs to be scheduled for execution. For instance, when the ACQ key on keyboard 38 is depressed, the executive program in computer 20 schedules the CNCT application program to be executed. If previous application programs had been scheduled, the CNCT program will not be performed until these previous programs have been performed. It should also be noted that it is also possible to transfer or branch, from one program to another program and return to the original program, and this is indicated when a block has therein the symbols "JST_____", where the blank is the name of the program to be branched to. As used in FIGS. 4 through 21, whenever a block in a given program has the word "RETURN" written therein, a return occurs to the program which caused given program to be executed, which may be either the executive program or another application program. If the return is to the executive program, the next scheduled applications program is executed, and if the return is to another applications program, the execution of that other program is continued.

Before describing the flow diagram shown in FIGS. 4 through 24 in detail, a brief description of the organization of the programs in computer 20 will be given. As previously mentioned, computer 20 is capable of simultaneously comparing and then occurring electrocardiac waves from each of the patient's signals PN1 through PN8 against a previously established master image for that particular patient. This is called the monitoring phase of operation. However, computer 20 can only establish the master image for one bed at a time and this is called the acquisition phase of operation. There are five basic programs concerned with the acquisition phase of operation and these are ACQ shown in FIGS. A and B, ATTACH shown in FIG. 8, PHASE1 shown in FIG. 9, PHASE2 shown in FIG. 10, and COPY shown in FIGS. 11A and 11B. In the case of the ACQ and COPY programs, only portions thereof are used in the acquisition phase with the remaining portions being used in the monitoring phase of operation. Also included in the monitoring phase is the ECTO program shown in FIG. 13 and the ARCHK program shown in FIG. 5. Other phases of operation are power up which utilizes GO program shown in FIG. 4; the keyboard response programs CNCT (FIG. 6), DROP (FIG. 19), SHOW (FIG. 20), SUSP (FIG. 21), PVCSET (FIG. 22), RSET (FIG. 23), and RATE (FIG. 24). In addition, there is a reporting phase of operation, using programs ERROR (FIGS. 17A-17C), EKG (FIG. 18), and REPORT (FIGS. 16A-16C) and a data handling phase of operation using programs ERST (FIG. 14) and HRLY (FIG. 15).

It should be noted that the various possible sequences of the ACQ and COPY programs are determined by the then existing value in the status code (ST), which may vary between 0 and 5, as will be explained hereafter in more detail. It should further be noted that the ACQ program is executed on a priority basis every 1/120th of a second and the remaining programs are executed between executions of the ACQ program. In the event one of the remaining programs is being executed when the time for execution of the ACQ program has arrived, the program being executed will be interrupted with the point of execution therein being saved along with the values and the A and X registers shown in FIG. 3. After the ACQ program execution has been completed, a return will be made to the interrupted point in the program which was previously being executed, and its execution will continue from there.

Figure 4:
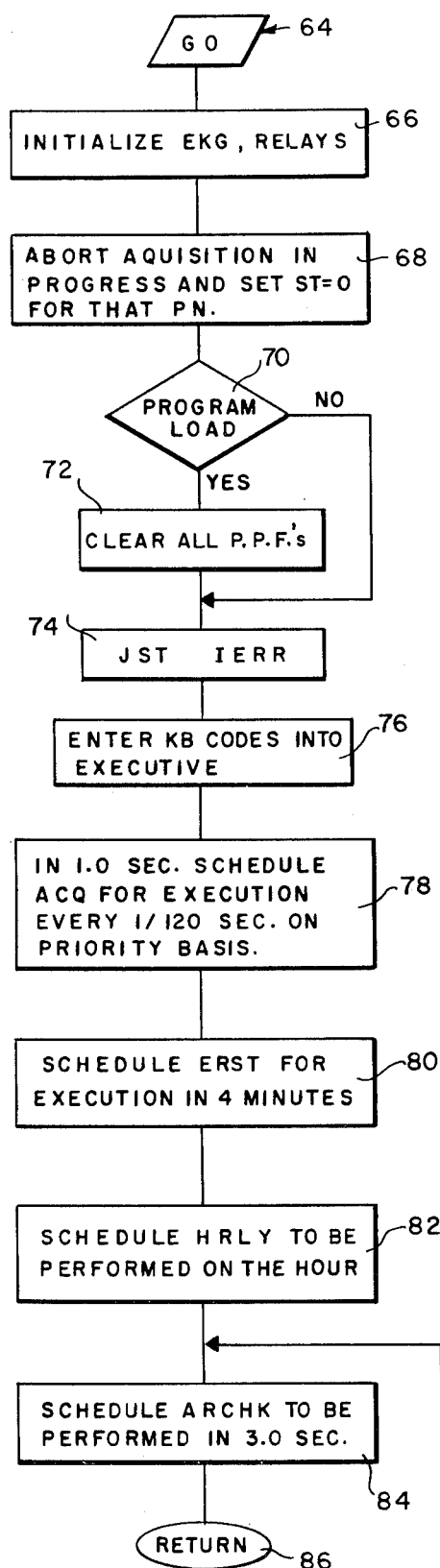
FIG. 4 is a flow diagram of the GO program for the computer of FIG. 1, which GO program is executed immediately upon an application of power to the computer.

Referring now to FIG. 4, GO program 64 is automatically scheduled by the executive program for execution each time power is applied to computer 20. This may be, for instance, at the time of initial startup or after a power failure. GO program 64 includes blocks 66 through 86 (even numbers). The first event which occurs according to block 66, is that EKG Recorder 30 and Relay Control Recorder Circuit 26 are initialized. In the case of EKG 30, the recording of any patient electrocardiac signal previously being recorded when power went down is terminated and all signals in the EKG queue are cleared. In the case of the Relay Control Circuit 26, all relays therein are opened, with the exception that the signal last applied to scope 32 will continue to be applied thereto.

Next, according to block 68, any acquisition previously in progress is cancelled and must be restarted and the status indicator ST is set equal to 0 for the patient that was being acquired at power down time. It should be noted that when ST equals 0 either a suspended or disconnected condition exists for that patient.

Then, according to block 70, a determination is made of whether a program is then being loaded into computer 20. If it is determined that the program is then being loaded into computer 20, the eight P.P.F.s are all cleared according to block 72; otherwise block 72 is skipped and the P.P.F.s are allowed to remain in their previous state.

According to block 74, a jump and store return to the IERR program shown in FIG. 17C, occurs, which, as will be explained in more detail hereafter, causes any errors which had been previously detected before a power failure to be printed by printer 36. Thus, no error information is lost in the event of a short term power fail.

Figure 7A:
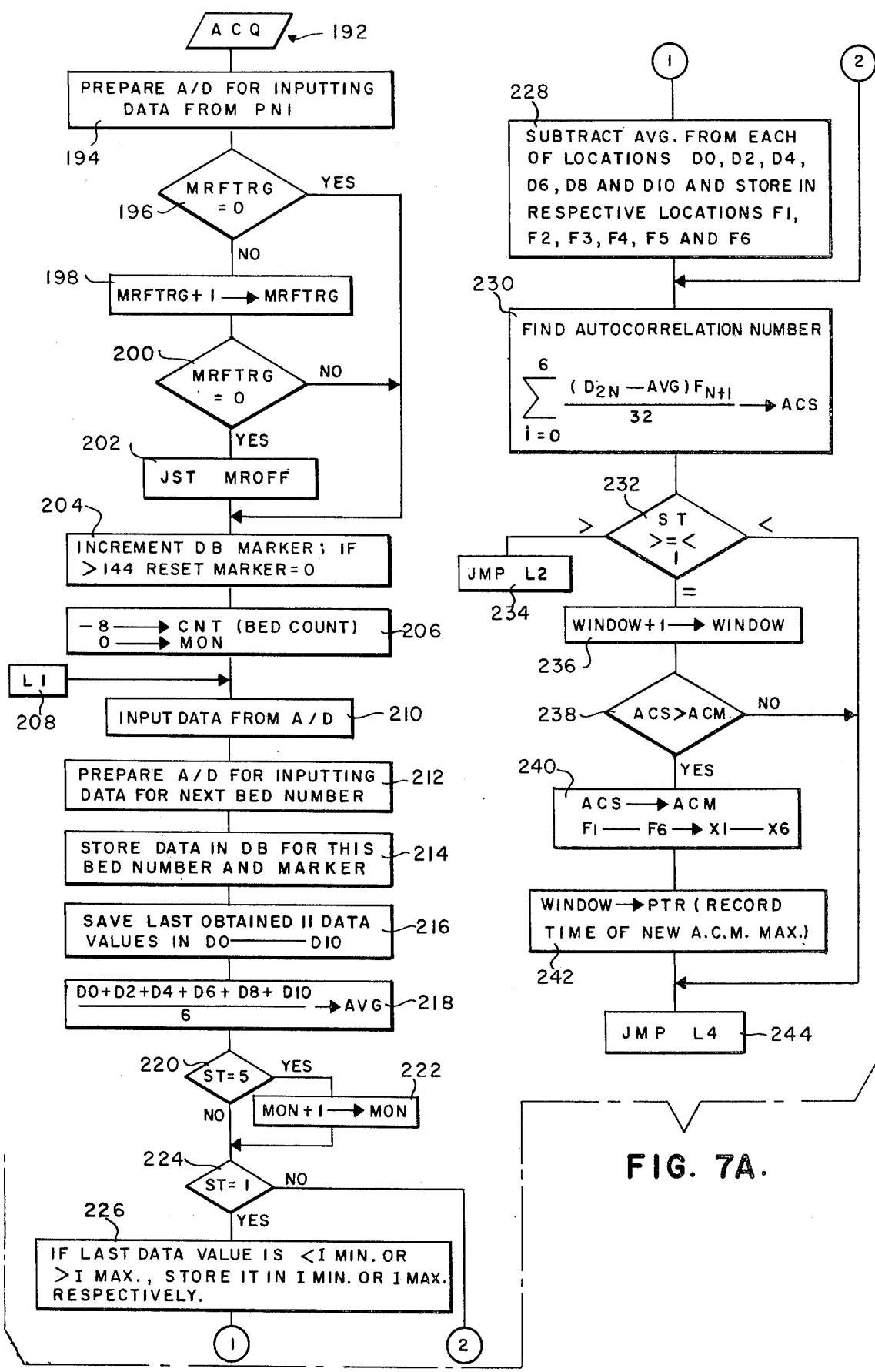
FIGS. 7A and 7B show a flow diagram of the ACQ program used to process each of the sample values provided to the computer.
Figure 7B:
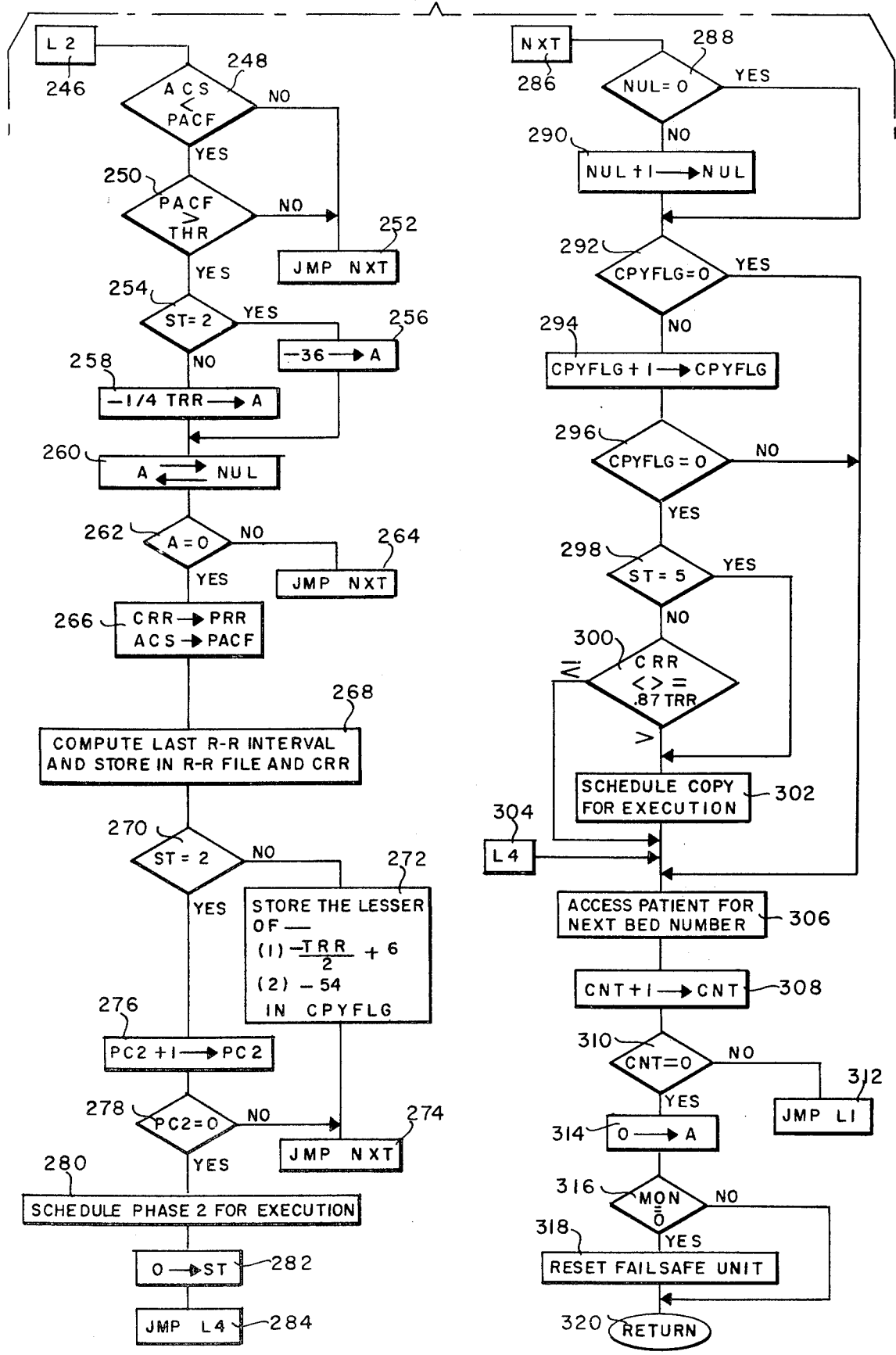

Next, according to block 76, the key codes from keyboard 38 are entered into the executive program to cause a scheduling of a specific application program when a corresponding key is depressed. Further, according to block 78, the ACQ program shown in FIGS. 7A, 7B and 7C, is scheduled for priority execution every 1/120th beginning one second thereafter. As indicated by block 80, the executive program is then directed to schedule the ERST program (FIG. 15) to be executed in 4 minutes and then, as indicated by block 82, the executive program is directed to schedule the HRLY program (FIG. 14) to be executed every hour on the hour. Finally, block 84 indicates that the executive program is directed to schedule the ARCHK program (FIG. 5) for execution in 3 seconds. Thereafter, as seen from block 86, a return to the executive program is indicated.

Figure 5:
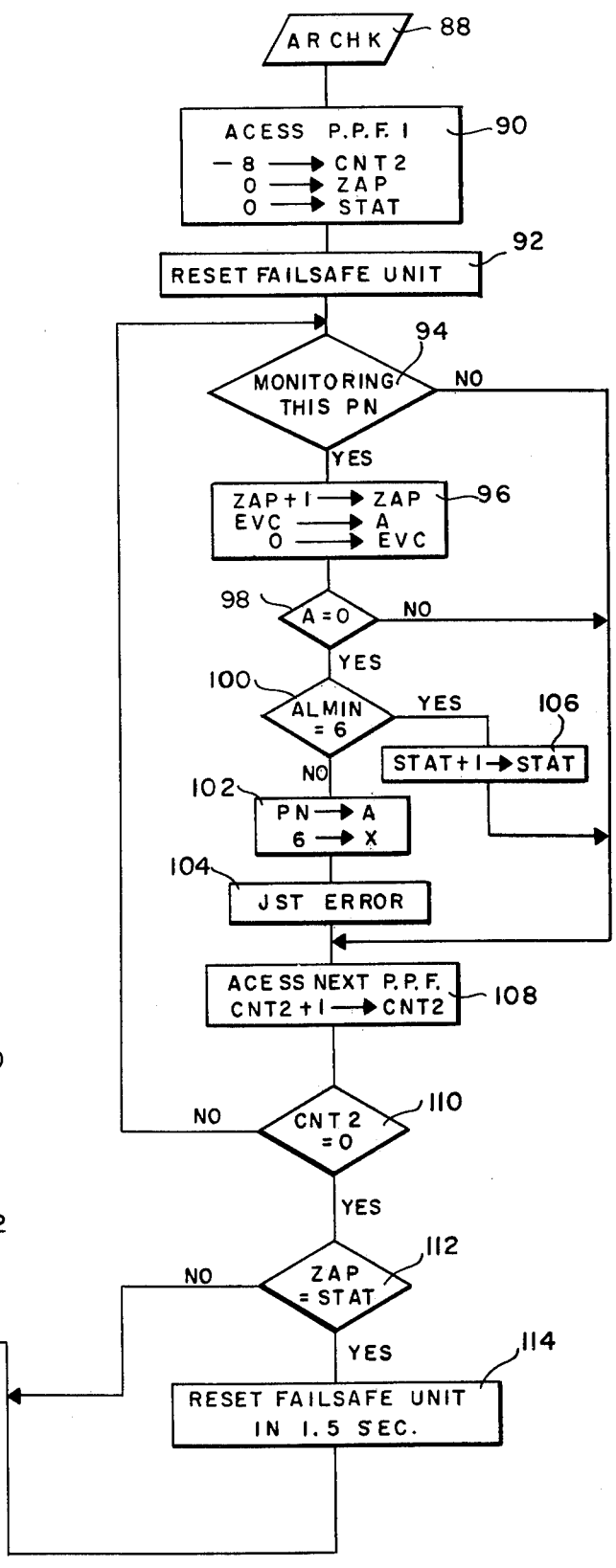
FIG. 5 is a flow diagram of the ARCHK program which is used to determine whether a signal for any particular patient connected to the system has been lost.

Referring now to FIG. 5, ARCHK program 88 will be described, which program is executed 3 seconds after its scheduling at block 82 in FIG. 4. This program checks the event counter in each P.P.F. having ST equal to 5. When ST equals 5, thereby indicating that monitoring is underway, each time a heartbeat is detected for a particular patient, that is, the QRS complex is found, the event counter word (EVC) in that patient's P.P.F. is incremented. Thus, if after 3 seconds, the event counter count for any particular patient is 0, thereby indicating no QRS complexes have been found during the previous three second interval for that patient, then, the P.N. signal for that patient has fallen below limits, thereby indicating either a cardiac arrest, or heart stoppage, has occurred, or the electrical apparatus has become disconnected. In this situation, the ARCHK program 88 causes printer 36 to print "LOST EKG BED ." and the alarm inhibit word for that patient is set to inhibit alarms for 60 seconds to give the operator of system 10 60 seconds to determine if the lost EKG situation is due to an electrical malfunction, such as an electrode falling off the patient. If event counter EVC has a non-zero count, at least one heartbeat during the last 3 seconds occurred, and event counter EVC is reset to a 0 count during the execution of ARCHK program 88.

Referring now specifically to ARCHK program 88, which consists of block 90 through 114 (even numbers only), and blocks 84 and 86 in FIG. 4. Block 90 indicates first that the computer accesses the P.P.F. for patient one (P.P.F.1), sets the CNT2 word in ARCHK program 88 to −8 and sets the ZAP and STAT words in ARCHK routine 88 to 0. Then, according to block 92, a reset signal is applied over line 52 to failsafe unit 44. Next according to block 94, a determination is made whether the patient for which the P.P.F. is then accessed (in this case P.P.F.1) is being monitored. This may be determined by merely determining whether the ST word in the accessed P.P.F. is set equal to a count of 5.

Assuming the determination in block 94 is the particular patient is being monitored then according to block 96, the ZAP word is incremented and the word in the event counter EVC is transferred to the A register of computer 20 and the event counter EVC is cleared to have zero count therein. Then, according to block 98, a determination is made whether or not the value in the A register is equal to 0. If this value is equal to 0, it indicates that the event counter during the preceding 3 second intervals has not been incremented and therefore no QRS complexes of the patient's EKG signal had been detected. This in turn, indicates that a lost EKG situation has occurred. Then, according to block 100, a determination is made whether the value stored in the alarm inhibit word ALMIN in the accessed P.P.F. is equal to six. If the ALMIN word is not equal to six then that particular patient's number is stored in the A register of computer 20 and the number six is stored in the X register of computer 20, as indicated by block 102, and a jump and store return to the ERROR program shown in FIG. 17A, occurs, as indicated by block 104. If the value in the ALMIN word has been equal to six, then the STAT word is incremented by one, as indicated by block 106, and blocks 102 and 104 are skipped.

Referring again to block 94, if it had been determined that this particular patient was not being monitored, then blocks 96, 98, 100, 102, 104 and 106 are skipped and a jump to block 108 occurs; similarly if at block 98 a determination has been that A was not equal 0, blocks 100, 102, 104 and 106 are skipped and a jump to block 108 occurs. Block 108 indicates that, at this point, the next P.P.F. is accessed and the value in the word CNT2 is incremented by one. It should recalled that initially this value was set to minus eight. In block 110, a determination is made of whether the value in the CNT2 word is equal to 0. If it is not, a return to block 94 is indicated. Since the CNT2 word was initially set to −8 the routine including blocks 94 to 108 (even numbers) is performed eight times, that is, once for each patient capable of being monitored by system 10. When the determination in block 110 is that the value in the CNT2 word is equal to 0, then according to block 112 another determination is made of whether the ZAP word has a count therein equal to the count of the STAT word. If these two counts are not equal, a jump to block 84 in FIG. 4 is indicated. However, if it is determined that the ZAP word count is equal to the STAT word count, then block 114 indicates that the executive program is directed to reset the failsafe unit in 1.5 seconds and a branch to block 84 in FIG. 4 occurs. The reason for the inclusion of incrementing the ZAP and STAT words and making the determination of whether they are equal is to insure that the failsafe unit 46, is reset whenever all of the patients being monitored have a lost EKG situation. This procedure is necessary because, for instance, if only one patient is being monitored, and he loses his EKG signal, the failsafe unit 46 would not be reset by the normal manner, which is hereafter described with respect to the COPY program in FIG. 11A, and would thus produce a false alarm.

As previously explained, after a branch is made to block 84, the ARCHK program 88 is scheduled to be executed in another 3 seconds. Thus, ARCHK program 88 is executed once every 3 seconds as long as power is applied to system 10.

Figure 6:
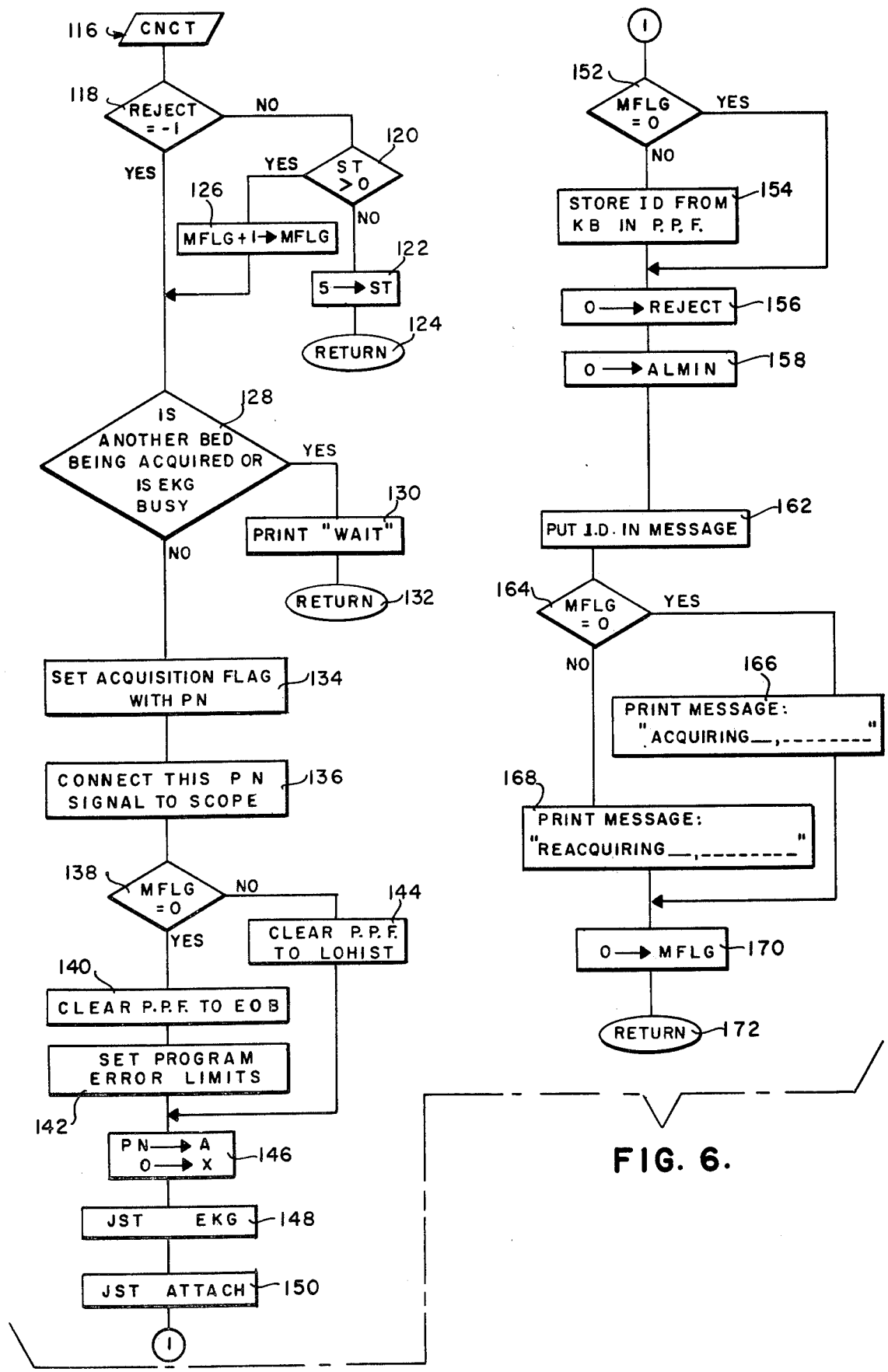
FIG. 6 is a flow diagram of the CNCT program used to connect a patient to the system after a command to do so is entered into the keyboard shown in FIG. 1.

Referring now to FIG. 6, when it is desired to connect a patient to the system 10, the operator depresses the ACQ key on keyboard 38, followed by a number corresponding to that patient and of the ENTER key. This directs the executive program to schedule CNCT program 116 to be executed as soon as all previously scheduled programs are executed. CNCT program 116 includes block 118 through 172 (even numbers only). As previously explained the depression of the ACQ key followed by a depression of a number corresponding to a patient and the ENTER key can have one of three meanings, this is (1) to initially acquire certain acquisition data and thereafter monitor a patient using that data; (2) to acquire new acquisition data and thereafter continue monitoring a patient who had previously been acquired and was being monitored or (3) to reconnect a patient who previously had been suspended and thereafter continue monitoring the patient using the initial acquisition data. Before a patient can be initially acquired, it is necessary that the previously monitored patient be dropped. The dropping of a patient, as will be explained hereafter, causes the P.P.F. for that patient to be totally cleared; thus, if the P.P.F. is clear, the meaning of a depression of the ACQ key on keyboard 38 means an initial acquisition of that patient. However, if the P.P.F. is not clear, the depression of the ACQ key on keyboard 38 indicates that a reacquisition or a reconnection after a suspension is to occur. As will be explained hereafter, in the case of a suspension, the value in status word ST in the suspended patient's P.P.F. is set equal to zero with no other changes to the P.P.F. Thus, if a reconnection is to occur, the P.P.F. is not clear and ST equals to zero whereas if a reacquisition if to occur the P.P.F. is not clear and ST does not equal zero.

Referring now to blocks 118 through 124 (even numbers only) of CNCT program 116, the determination of the meaning of the depression of the ACQ key is made. In block 118, the determination is first made, for the patient corresponding to the number key depressed, whether that patient's P.P.F. has the REJECT word set equal to a −1.

The REJECT word is set equal to −1 whenever the P.P.F. is cleared such as, after a previous patient has been dropped. If that P.P.F. is not clear, that is REJECT does not equal minus one, then according to block 120, a determination is made whether ST is equal to 0. If ST equals 0, then a disconnected situation is detected, and according to block 122 ST is set equal to 5 and return to the executive program occurs, as indicated by block 124. If the determination at block 120 was that ST was greater than 0, thereby indicating a reacquire situation, then according to block 126 the word MFLG is incremented to a count of one and a continuation with block 128 occurs. Referring again to block 118, if it was determined that the particular P.P.F. was clear, that is; REJECT equalled −1, then a continuation with block 128 occurs.

According to block 128, it is next determined whether another bed is being acquired at time, or whether EKG recorder 30 is then busy. If either of these events is true, then, according to block 130, printer 36 is caused to print "WAIT" and return to the executive program occurs, as indicated by block 132. At this point the operator should wait approximately 1 minute and again depress the ACQ key, followed by the patient number and ENTER keys on keyboard 38. However, assuming the determination at block 128 indicated that no other bed was being acquired and that recorder 30 was not busy, then block 134 indicates that the acquisition flag is set with the particular patient number, which had been typed into keyboard 38 following the depression of the ACQ key. It should be noted that in block 128, the determination of whether another bed is being acquired may be made by checking the acquisition flag and to see whether or not it is set equal to 0. Its not being 0 indicates that another bed is being acquired. Thus, by the action of block 134, the setting of the acquisition flag with the patient number serves to inhibit a further patient from being acquired by the action in block 128 until the acquisition of the current patient is completed. Next, according to block 136 the electrocardiac signal of the patient being acquired is coupled to cardioscope 32. This may be done by computer 20 transmitting a signal over line 28 to relay control circuit 26 which closes a particular relay, thereby causing this patient's EKG signal to be applied to cardioscope 32.

Next, according to block 138 a determination is made of whether the value in the MFLG word is equal to 0. It should be recalled from block 126 that the value in the MFLG word was incremented to a value of one in the event of a depression of the ACQ key indicated a reacquisition was to occur. If, at block 138, the MFLG value is determined to be equal to 0, block 140 indicates that the entire P.P.F. for this patient is cleared and block 142 indicates that the program error limits are stored in the P.P.F. for this patient. As previously explained, these limits may be subsequently changed by the depression of certain keys on keyboard 38. If at block 138, it was determined that the MFLG value was not equal to 0, then block 144 indicates that the P.P.F. is only cleared through the LOHIST words, that is that portion of the P.P.F. relating to acquisition data; however, the patient history data, in a case of reacquisition, is maintained intact in the memory.

Figure 18:
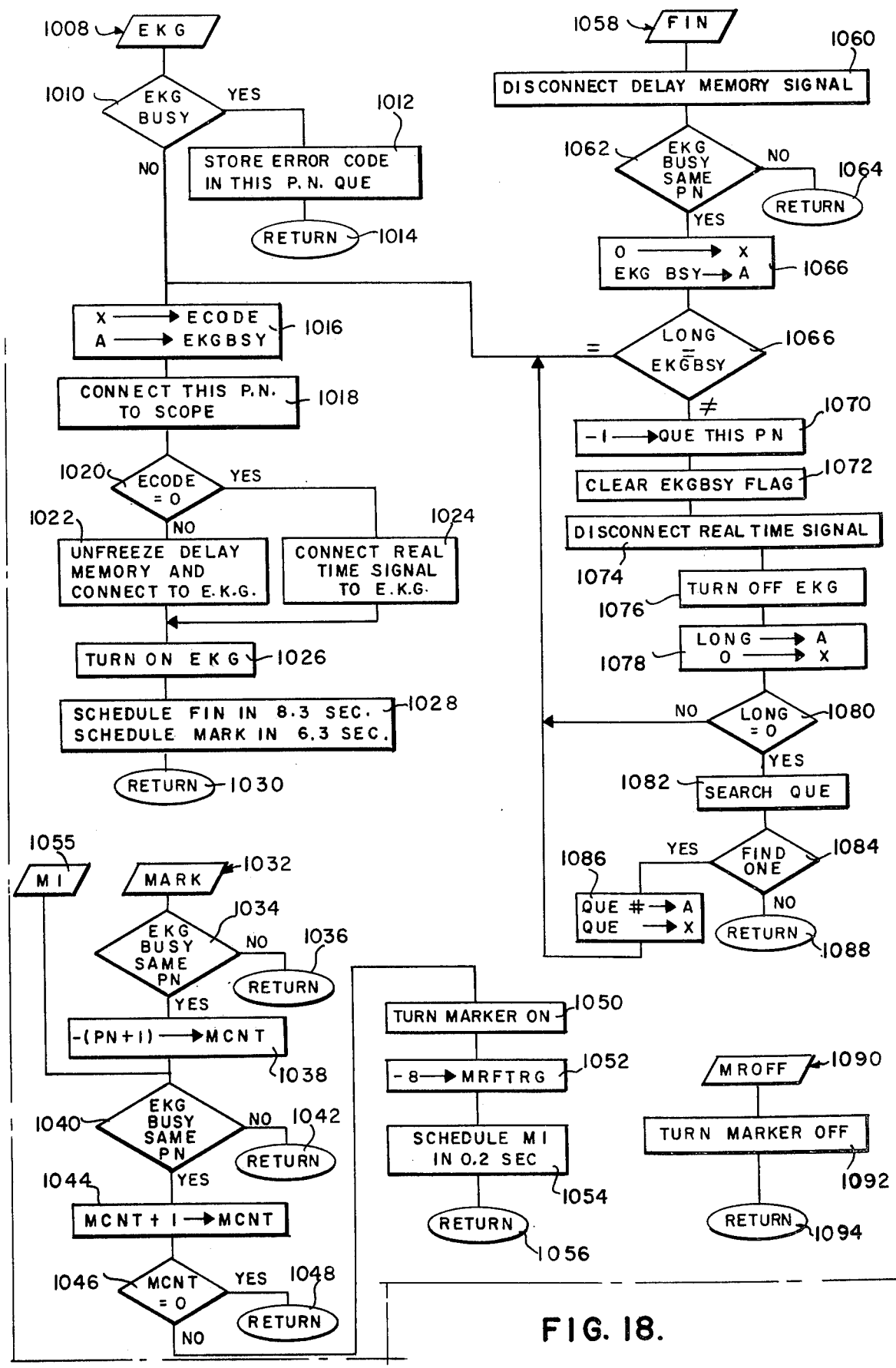
FIG. 18 is a flow diagram of the EKG, MARK, FIN and MROFF programs used to control the EKG strip chart recorder shown in FIG. 1.

After the performance of the function in blocks 142 or 144 the next occurrence, as indicated by block 146, is that the patient number is transferred to the A register of computer 20 and to X register of computer 20 is cleared and then, according to block 148, a jump and store return to the EKG program shown in FIG. 18 occurs. The conditioning of the A and X registers at block 146 causes EKG recorder 30 to provide a real time strip record for this patient, as will be explained in more detail with respect to EKG program in FIG. 18.

Figure 8:
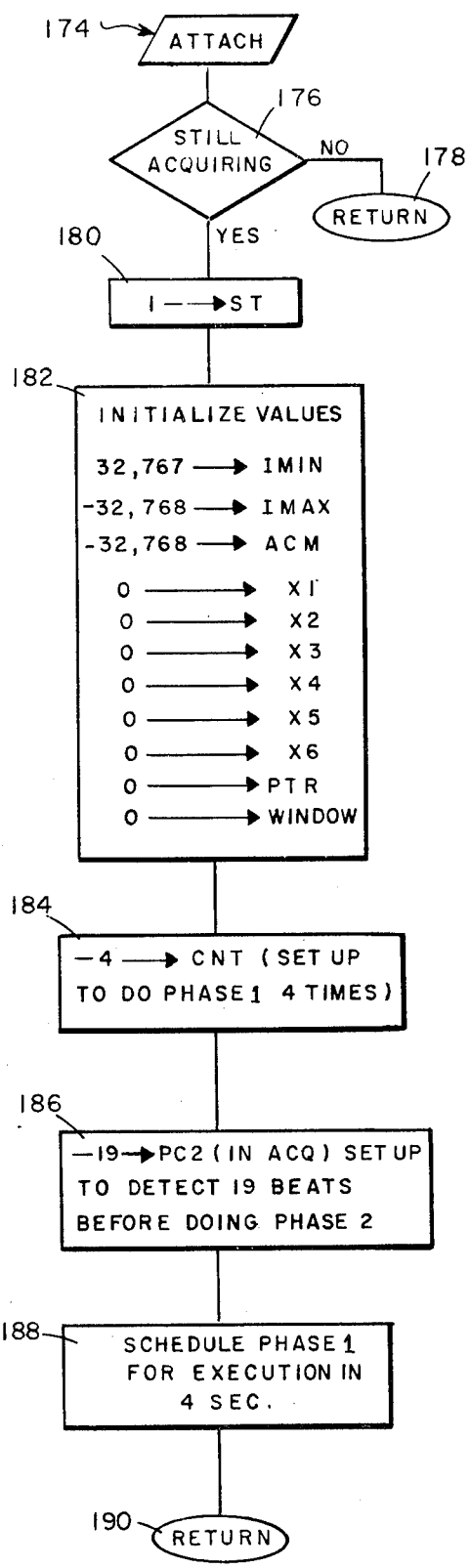
FIG. 8 shows a flow diagram of the ATTACH program used to prepare the computer for acquiring the master image of a patients electrocardiac signal.

Thereafter, as indicated by block 150, a jump and store return in the ATTACH program 174 shown in FIG. 8, occurs.

Figure 9:
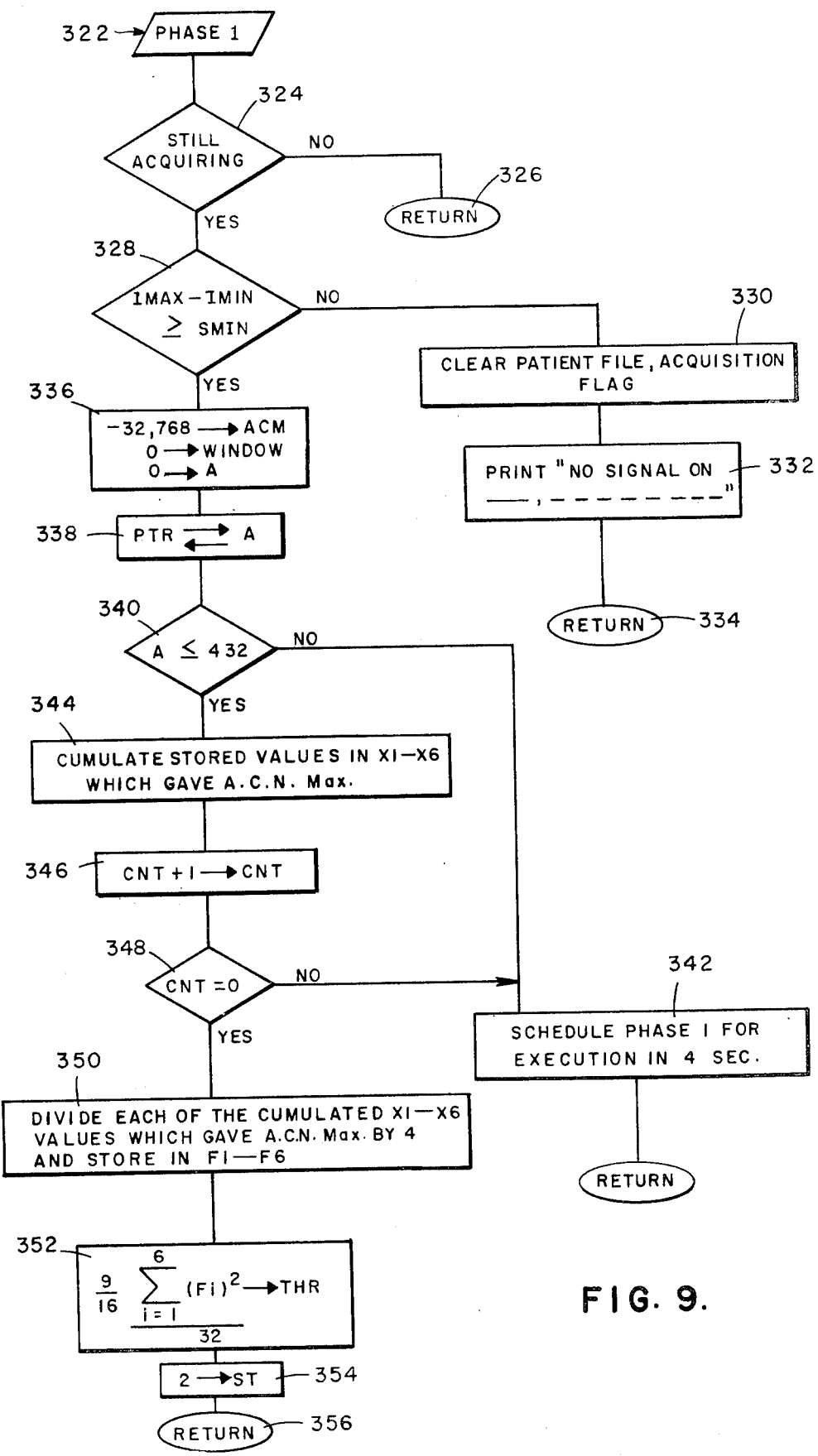
FIG. 9 shows a flow diagram of the PHASE 1 program used to determine the autocorrelation mask for the electrocardiac signal being acquired.

Referring to FIG. 8, ATTACH program 174 initiates certain values and directs the executive program to schedule the PHASE1 program, shown in FIG. 9, as the first phase of acquiring a patient's signal. ATTACH program 174 includes blocks 176 through 190 (even numbers only). The first step in ATTACH program 174 is to test whether the acquisition flag is still set, as indicated by block 176. If the acquisition flag for some reason had become reset to 0, a return to CNCT program 116 occurs, as indicated by block 178. However, assuming that the patient is still under acquisition, block 180 indicates that the status word ST is set equal to 1. Thereafter, according to block 182, certain values are initialized and specifically, the IMIN value is set to 32,767 or the maximum allowed value and the IMAC value is set to −32,768 or the minimum allowed value. Further, the value in location ACM, which is the maximum autocorrelation value, is set to −32,768. Finally, the X1 through X6 values, the PTR value and WINDOW value are all set equal to 0. IMIN, IMAX, ACM, and X1 through X6 values are a part of the application programs and when the pertinent programs are described in detail, their importance will then become apparent.

Figure 10:
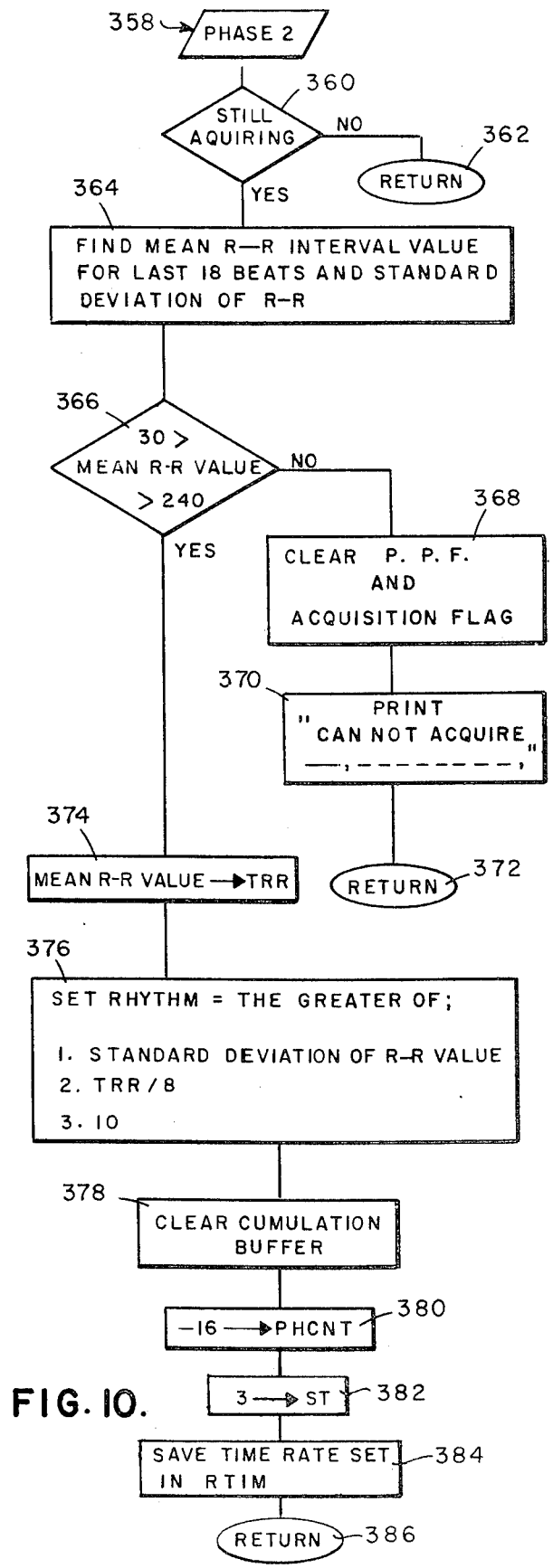
FIG. 10 shows a flow diagram of the PHASE 2 program used to determine the rate of the electrocardiac signal being acquired.

ATTACH program 174 continues with block 184, which indicates the CNT location in PHASE1 program (FIG. 9) is set to a value of −4 so the PHASE1 program will be performed four times. Next, according to block 186, the PC2 location in ACQ program (FIG. 7B) is set to a value of −19 and this results in 19 QRS complexes being detected prior to doing the PHASE2 program (FIG. 10). Next, according to block 188, the executive program is directed to schedule the PHASE1 program (FIG. 9) for execution in 4 seconds. Finally, according to block 190, a return to block 152 of CNCT program 116 is indicated.

Referring again to FIG. 6, according to block 152, a determination is again made of whether the value in the MFLG word is equal to 0, thereby indicating an initial acquisition, or whether MFLG value is equal to 1, thereby indicating a reacquisition. If at block 152 it is determined an acquisition is in progress, then block 154 indicates that the patient's ID number is obtained from keyboard input and stored in the PID location of the P.P.F. If at block 152 it was determined that a reacquisition was in progress, then block 154 is skipped.

Next, according to block 156, the REJECT location is set equal to 0 and, according to block 158, the alarm inhibit location ALMIN is set equal to 0. It should be noted that both the REJECT and the ALMIN locations are in this patient's P.P.F.

Next, according to block 162, the ID data stored in the PID location of the P.P.F. is transferred to the message to be printed. Then, according to block 164, a determination of whether the value in the MFLG word is equal to 0 is again made. If the MFLG value is determined to be equal to 0, then according to block 166, the message

"ACQUIRING ___,___ ___ ___ ___ ___ ___ ___"

is printed. If at block 164 it is determined that the MFLG value is not equal to 0, then according to block 168, the message

"REACQUIRING ___,___ ___ ___ ___ ___ ___ ___"

is printed. In either of these messages, as well as subsequent discussed messages having a similar format, the first blank preceding the comma, indicates the patient number and the eight blanks following the comma indicate the patient ID number. It should be noted that although eight blanks are allowed for an ID number, nothing prevents an ID number from being less than eight characters in length and filling the remaining blanks with blank characters. After the message of blocks 166 or 168 is printed, the next occurrence, as indicated by block 170, is that a 0 is stored in the MFLG word and, according to block 172, a return to the executive program then occurs.

Referring now to FIGS. 7A and 7B, ACQ program 192 is shown. It should be recalled from block 78 in GO program 64 (FIG. 4) that ACQ program 192 is executed, on a priority basis, every 1/120th of a second. The various manners by which ACQ program 192 can process a sample value will be described with respect to the particular phase of operation with which the acquisition process is then involved. This, in turn, is determined by the then existing value stored in the ST word in that patient's P.P.F. ACQ program 192 includes blocks 194 through 320 (even numbers only) and is divided into four basic portions which are respectively the common portion of ACQ program 192 shown in FIG. 7A and L2 routine 246, the NXT routine, 286 and the L4 routine 304, all shown in FIG. 7B.

Every 120th of a second, when the ACQ program 192 is scheduled, each of the eight electrocardiac signals is sampled and the analog sample value is converted to a corresponding digital value. Then, the digital values manifesting the analog sample values are stored in a buffer included in circuit 16 and upon command, these stored values are provided to computer 20 in sequential order. For each of the eight sample values so provided, certain processing occurs, and depending upon the value of ST for the signal from which the sample was taken, certain other processing occurs.

When execution of ACQ program 192 begins, block 194 indicates that the analog-to-digital converter in circuit 16 is prepared to input data, upon command, for the first patient's signal.

Blocks 196, 198, 200 and 202 provide processes to turn off the EKG marker which operates by placing a number of marks on each EKG strip provided by EKG recorder 30. The number of marks is equal to the patient number to which the strip relates and will be explained in more detail in the EKG program (FIG. 18). The marker is turned on at specific times by the EKG program and at the same time, a location MRFTRG in ACQ program 192 is set to a count of −8. According to block 196 a determination is made whether the value in location MRFTRG is equal to 0. If it is not equal to 0, thereby indicating the marker is on, block 198 increments the count in MRFTRG location by 1. Thereafter, according to block 200 another determination is made whether location MRFTRG has a count of 0 therein. If at this point the cont in location MRFTRG is equal to 0, block 202 indicates that a jump and store return to MROFF program, shown in FIG. 18, occurs. MROFF program as will be explained hereafter, turns off the marker in EKG recorder 30. If the determination at block 196 had been that MRFTRG location had a zero count therein, or if the determination at block 200 was that MRFTRG location had a nonzero count therein, then a jump to block 204 is indicated. In this manner, the marker is maintained on for 0.067 seconds, or for the time required to perform the ACQ program eight times.

Block 204 indicates that the data buffer marker is then incremented by one, unless it previously had been at a count of 144, in which case it is reset to a count of 0. The reason for this is that the data buffer in each of the P.P.F.s is 72 words in size with each word storing two eight bit sample values (bytes); thus, there are 144 values so stored. The value in the data buffer marks will address either the left or right side of a particular data buffer word. For instance, when the marker is set to 0, it will address the lower eight bits of the first location of the data buffer; when it is set to 1, it will address the upper eight bits of the first location of data buffer; when it is set to 2, it will address the lower eight bits of the second location; and so forth until when it is set to 143 it will address the upper eight bits of the 70-second location. In this manner, the last 144 data values sampled from each of the electrocardiac signals are stored in the respective data buffers of the P.P.F.S for those signals, or, in other words, the last 1.2 second of each electrocardiac signal is stored in the data buffer for that signal.

Next, according to block 206, a value of minus eight is stored in the CNT location in the ACQ program 192. It should be noted that this CNT location is different than the previously discussed CNT location in AT-TACH program 174, shown in FIG. 8, because it is in a different program. The reason for setting the CNT location in the ACQ program 192 to −8 is because ACQ program 192 is to be repeated for each of eight patients capable of being monitored.

ACQ program 192 continues with block 210, which indicates that circuit 16 is commanded to input data for the patient for which it previously had been prepared, or in this case, the first patient for which it was prepared by the action at block 194, as previously discussed. Block 208, labeled L1, which is to the left of block 210 is merely a lable for a return point after the date applied from the one patient has been processed in the desired manner and the date from the next subsequent patient is desired to be inputted to computer 20.

After the data from circuit 16 is applied to the computer 20, block 212 indicates that circuit 16 is prepared to input the data, on command, for the next patient, in this case the second patient. Thus, after the return to L1 block 208, block 210 will command circuit 16 to transfer the digitized sample value from the second patient to computer 20.

Continuing now with the process of acquiring the data for the first patient block 214 indicates that the data inputted to computer 20 is then stored in the data buffer in that patient's P.P.F. at the location designated by the value of the data buffer marker from block 204, discussed above. As previously mentioned, this data will be stored for 1.2 seconds, at which time it will be replaced by the occurring data and lost.

In addition to saving 1.2 seconds of data in the data buffer, block 216 indicates the last eleven data values are saved in the D0 through D10 locations for each patient in that patient's P.P.F., with the D0 location always containing the most recent sampled data and the D10 location containing the data sampled 11 samples ago. It should be noted that after each sample value is applied to computer 20, the data in the D0 through D9 locations is moved to the next higher D1 through D10 location and the data in the D10 location is lost. According to block 218, the average value of the data in locations D0, D2, D4, D6, D8 and D10 is then found by adding the values stored in each of these locations and dividing by 6, and this average value is stored in the AVG location in ACQ program 192.

Next, according to block 200 the value of ST is determined. If ST is equal to 5, then block 222 indicates that the location MON in ACQ program 192 is incremented by 1. The significance of this incrementation of the MON location will be discussed hereafter with respect to block 316 in FIG. 7B.

According to block 224, a determination is then made whether ST equals one. If ST is not equal to one then blocks 226 and 228 are skipped; thus, it is only during the time that ST equals one that operations defined by blocks 226 and 228 are performed. According to block 226, the most recent received sample value is checked to determine whether it is less than a stored minimum sample value previously received, which minimum value is stored in the IMIN location. A determination is also made whether the most recent sample value is greater than a stored maximum sample value previously received which previous maximum value is stored in the IMAX location. If either event is true, the proper one of the IMIN or IMAX location is updated to indicate the new minimum or maximum sampled value. Since the IMIN or IMAX values are only used during the acquisition protion of the program, they are storage locations defined in ACQ program 192, and not a part of the P.P.F. since only one patient can be acquired at one time.

According to block 228, the average value stored in location AVG, calculated in block 106, is then subtracted from each of the values stored in locations D0, D2, D4, D6, D8 and D10 of the P.P.F. for this patient and the results from each of these subtractions is respectively stored at locations F1, F2, F3, F4, F5 and F6 in the particular P.P.F. Thus, the values in locations F1 through F6 are the values in locations D0, D2, D4, D6, D8 and D10, all reduced to a 0 mean. As used herein, the term "reduced to a 0 mean" means that the average value of the numbers involved in the operation is subtracted from each number so involved. Thus, the sum of the numbers reduced to a 0 mean is approximately 0, with any deviation from 0 being due to rounding errors.

According to block 230, the autocorrelation number for six alternate ones of the last 11 sampled data values is then calculated as follows: (D0-AVG)F1 + (D2-AVG)F2 + (D4-AVG)F3 + (D6-AVG)F4 + (D8-AVG)F5 + (D10-AVG)F6. This number is then scaled, that is divided by 32, to reduce it to a more manageable value, which is herein called the autocorrelation number and stored in the ACS location in ACQ program 192. The reason for this calculation is to find the maximum point for each heartbeat of the electrocardiac signal, that is, the R wave, so that a common point of reference for each beat may be established.

Referring again to FIG. 2, it should be appreciated that after the value from sample time 55 is stored in the D0 location, a maximum autocorrelation number is obtained, by summing the squares of sample values at times 45, 47, 49, 51, 53 and 55, reduced to a 0 mean. This maximum autocorrelation number is in the QRS complex of wave 62. By continually performing the autocorrelation calculation, the same point on the electrocardiac signal for each heartbeat can be found. It should be noted that the autocorrelation calculation is performed each time a sample value is applied to computer 20.

It should also be noted that when the ST value equals one, the autocorrelation calculation performed in block 230 will actually be a determination of the sum of the squares of the most recent sampled values; however, when the ST value equals two or more, a permanent value will be stored in each of the locations F0 through F6, as will be explained in more detail with respect to the PHASE1 program shown in FIG. 9, and in that event the calculation at block 230 will not be merely a sum of the squares calculation but rather a true autocorrelation calculation.

Continuing again in FIG. 7A with block 232, a determination of the value in the ST location is again made. In the event that ST is less than one, a jump to L2 routine 246 in FIG. 7B is indicated by block 234. However, continuing at this point with ST equal to 1, block 236 indicates the value in location WINDOW is incremented by one. Then, block 238 indicates that a test is made to determine whether the autocorrelation number just calculated and stored at the ACQ location is greater than the value in stored location ACM (autocorrelation maximum). If it is not, a continuation at block 244 occurs, which indicates a jump to L4 routine 304 in FIG. 7B. However, if the last calculated autocorrelation number is a new maximum value, block 240 indicates that the new autocorrelation value is stored in the ACM location and that each of the F1 through F6 values, which were used to determine the autocorrelation numbers, are stored in temporary storage location X1 through X6 for later use in the PHASE1 program shown in FIG. 9. When a new maximum autocorrelation value is found, the value in the WINDOW location is stored in the PTR location to record the time at which the new maximum autocorrelation number is determined, as indicated by block 242. At this point, block 244 indicates that a jump to L4 routine 304 occurs.

Referring now to L4 routine 304 in FIG. 7B, block 306 indicates that the P.P.F. for the next patient is then accessed and block 308 indicates that the value in CNT location, initially set at −8, is incremented. Then continuing with block 310, a determination is made of whether or not the value in CNT location equals 0. If the CNT value is not equal to 0, a return to block L1 208 in FIG. 7A is indicated by block 312 and ACQ program 192 is repeated for the next patient capable of being monitored in this case the second patient. After the sampled values from all eight beds have been processed by ACQ program 192, the CNT value will equal 0 and in that event, block 314 indicates that the value of 0 is placed in the A register of computer 20 and block 316 indicates that a determination is made whether the count in MON location is equal to 0. If the MON count is equal to 0, then block 318 indicates that a reset signal is applied over line 52 from computer 20 to failsafe unit 44 to reset failsafe unit 44. Thereafter, or if the determination at block 316 is that the value in MON location was not equal to 0, block 320 indicates that a return to the executive program occurs and the next scheduled program will be executed. The effect of blocks 316 and 318 is to reset failsafe unit 44 if no patients are being monitored, in which event no QRS complexes are being detected so COPY program shown in FIG. 11 will not be called and the normal manner or resetting the failsafe unit 44 will not occur. Thus, for the situation in which no patient is being monitored, failsafe unit 44 is reset each time ACQ program 192 is performed, as indicated by the operation of blocks 316 and 318 rather than by the normal procedure in the COPY program, which is hereafter described in more detail.

ACQ program 192 is executed again 120th of a second later as a result of the executive program scheduling it for execution a priority basis and the identical procedure just described is repeated and this occurs each 120th of a second for the next 4 seconds. As discussed previously with respect to block 188 in ATTACH program 174 in FIG. 8, 4 seconds after ATTACH program 174 is executed, PHASE1 program 194, shown in FIG. 9, is scheduled for execution. Just prior to PHASE1 program 322 being executed, the ACM location in ACQ program 192 will contain a value equal to the largest autocorrelation number calculated during the previous 4 seconds and the X1 and X6 locations will contain the alternate ones of the last sample values, reduced to 0 means, which gave that largest autocorrelation number. Further, the PTR location will contain a value related to the time at which that largest autocorrelation number was calculated, and the IMIN and IMAX location will contain the values of the largest and smallest sample values captured during that previous 4 seconds.

Referring now to FIG. 9, PHASE1 program 322 includes blocks 234 through 356 (even numbers only). The first function performed by PHASE1 program 322 is to determine whether the acquisition flag is still set, as indicated by block 324. If some reason it had become reset prior to the scheduling of PHASE1 program 322, such as by a depression of the DROP key on keyboard 38, then block 326 indicates that a return to the executive progam occurs. However, assuming that the acquisition is still underway, then according to block 328 a determination is made whether a proper magnitude signal is being applied from the amplifier 12 associated with the patient being acquired, in this case, the first patient. This may be accomplished by finding the difference between the values stored in the storage locations IMAX and IMIN and determining if this difference is greater than a preset value stored in location SMIN. If this difference is not greater than the SMIN value, then block 330 indicates that the P.P.F. for the patient being acquired is cleared and the acquistion flag is cleared. Block 332 then indicates that printer 36 is to print the message

"NO SIGNAL ON ___,___ ___ ___ ___ ___ ___ ___".

Thereafter, block 334 indicates that a return to the executive program occurs and the next scheduled program is executed.

Referring again to block 328 and assuming that the difference between the IMAX and IMIN values is greater than the SMIN value, then block 336 indicates that the ACM value is reset to −32,768, and the values in WINDOW location is reset to zero and the A register in computer 20 is also reset to zero. PHASE1 program 322 continues with block 338 which indicates that the value in the PTR location is stored in the A register and the 0 value stored in the A register at block 336 is stored in the PTR location. It should be recalled from block 242 in ACQ program 192 that the value that was stored in the PTR location is the value of the WINDOW count at the time that the last maximum autocorrelation number was detected. Block 340 indicates that a test is made to determine whether the PTR value transferred to the A register is less than or equal to 432, or in other words, whether the last maximum autocorrelation number was detected during the first 3.6 seconds of the 4 second interval between the requesting and the execution of PHASE1 program 322. It is desired that the last autocorrelation number maximum not have been detected during the last 0.4 second of that 4 second interval because of possible contamination of the signal. Thus, if in block 340, the value in the A register is determined to be greater than 432, a jump to block 342 is indicated and PHASE1 program 322 is rescheduled for execution in another 4 seconds. Then, the steps up to this point are repeated until such time as the last maximum occurring autocorrelation number did not occur during the last 0.4 second of the 4 second interval between the scheduling and the execution of PHASE1 program 322.

Assuming that the last detected maximum autocorrelation number was within the first 3.6 seconds of the 4 second interval between the scheduling and the execution of PHASE1 program 322, then FIG. 7 contines with block 344, which indicates that the sample values giving the maximum autocorrelation value stored in locations F1 through F6, are added, point by point to the values stored in locations X1 through X6, as indicated by block 240 in FIG. 7A. Then, according to block 346, the value of the CNT location initially set at minus four at block 184 in ATTACH program 174 is incremented and according to block 348, a determination is made of whether the CNT value is equal to 0. If the CNT value is not equal to zero, a branch or block 342 occurs and PHASE1 program 322 is rescheduled for execution in another 4 seconds and the above discussed steps with respect thereto are repeated.

After PHASE1 program 322 has been executed four times with a 4 second interval preceding each execution, the CNT value will equal 0 and a continuation with block 350 will occur. At this point it should be noted that the values in locations X1 through X6 will equal the point-by-point sum of the values stored in locations F1 through F6 which gave the 4 maximum autocorrelation numbers during each of the 4 second intervals preceding the execution of PHASE1 program 322. Block 350 indicates that each of these cumulative values are then divided by 4 and stored in the F1 through F6 locations in that patient's P.P.F. Continuing with block 352, 9/16th of the sum of the squares of the F1 through F6 values divided by 32, is then stored in the THR location in that patient's P.P.F. as an autocorrelation threshold value for subsequent comparison against in a manner hereinafter explained. Thereafter, block 354 indicates that the ST value is set equal 2 and block 356 indicates a return to the executive program then occurs.

At this point when the executive program again schedules ACQ program 192 for execution, ACQ program 192 will be performed in the manner previously described up to and including block 222. However, at block 224 the determination of whether the ST value equals one will be negative, since ST was set equal to 2 at the end of PHASE1 program 322. Thus, blocks 226 and 228 are skipped. This is appropriate because it is only determined whether the signal amplitude is proper during PHASE1 program 322 and thus it is no longer necessary to set the IMIN and IMAX values according to block 226. Further, after PHASE1 program 322 is executed, permanent autocorrelation mask values are stored in the F1 through F6 locations, so it is not necessary to provide a manner of obtaining these values, as indicated at block 228.

Continuing with block 230, the autocorrelation number is then calculated by determining the sum of the point-by-point products of alternate ones of the last eleven sampled values scan in locations D0, D2, D4, D6, D8 and D10 reduced to a 0 mean times corresponding ones of the autocorrelation mask values stored in locations F1 through F6. It should be noted that at this point rather than using the square of the values themselves to find the maximum autocorrelation value for a particular wave, the product of the previously determined F1 through F6 values is used. This mitigates against detecting any extraneous pulses caused by, for instance, noise or artifact, as being detected as the QRS complex. It could be thought that in block 230, at this point, the cross-correlation value is being calculated rather than the autocorrelation value. However, because both the then sampled values in the D0 through D10 location and the values stored in the F1 through F6 locations are taken from the same sample, that is, the same patient's electrocardiac signal, only one population is involved, and hence, the value calculated according to block 230 is referred to as the autocorrelation number regardless of the fact that the F1 through F6 values remain constant, as previously derived, while the D0 through D10 values are allowed to vary with the current sample. With ST now set equal to 2, the determination at block 232 is that ST is greater than 1, so block 234 indicates a jump to L2 routine 246 in FIG. 7B occurs.

Referring now to FIG. 7B and particularly to the L2 routine 246, block 248 indicates that a determination is made whether the autocorrelation number just calculated at block 230 is less than the value in location PACF, which is the value of the autocorrelation number calculated during the processing of the immediate preceding sample value. If the presently calculated autocorrelation number ACS is greater than the previously calculated autocorrelation number PACF, a jump to the NXT routine 286 is indicated by block 252. However, if the PACF value is greater than the ACS value, the PACF value represents a maximum point in the wave. In that event, block 250 indicates a determination is then made whether the PACF value exceeds the THR value calculated and stored at block 352 during the performance of PHASE1 program 322 in FIG. 9. If the PACF value is less than the THR value, then block 252 indicates that a jump to the NXT routine 286 occurs because the detected maximum is not the R wave being sought.

If the PACF value is determined to be greater than the THR value at block 250, then a continuation with block 254 results. This can occur only after the R wave in the QRS complex is detected because only the values surrounding the R wave will be sufficiently high to provide an autocorrelation value, stored at ACS location which is less than the previous autocorrelation value stored at the PACF location, where the previous autocorrelation value is greater than the threshold value stored at the THR location. It should be noted that this situation may in addition occur for several sample values after the R wave is detected until such time as the previous autocorrelation value falls below the threshold value.

When the previous autocorrelation number PACF is greater than the THR value, block 254 indicates the value of ST is determined. When ST is equal to 2, block 256 indicates that the A register in computer 20 is set to a value equal to −36 and if ST is not equal to 2, block 258 indicates the A register is also set to a value equal to −TRR/4, where TRR is an average number of the times ACQ program 192 is performed between detection of successive QRS complexes during acquisition, and is explained in more detail with respect to the PHASE2 program in FIG. 10. In either event, according to block 260, the value in the A register and the value in the NUL location of this patient's P.P.F. and then exchanged, so that the value previously in the NUL location is transferred to the A register and either −36 or −TRR/4 is transferred to the NUL location.

As will be apparent hereinafter, the NUL location will previously have been incremented to 0 after the last QRS complex had been detected, so that the first time the exchange indicated by block 260 occurs, the value in A register will be equal 0. Thereafter for at least the next portion of a heartbeat, the value NUL will be nonzero, and thus, the value transferred to A register at block 260 thereafter will be nonzero.

According to block 262, the value in the A register is then checked to determine whether or not it is 0. If it is not 0, that is, if this is not the first time during this heartbeat that the previously calculated autocorrelation number both exceeded the presently calculated autocorrelation number and exceeded the THR value, thereby indicating the detection of the R wave in the QRS complex, block 2 indicates that a jump to the NXT routine 286 occurs. However, if the value in the A register is equal to 0, that is, the R wave in the QRS complex for this heartbeat has then been detected, the processing for the detected R waves continues. Thus, by using the NUL location as a countdown timer, the subsequent occurring situations during the following one quarter cycle, where the PACF value is greater than the THR value will not be processed as detected R waves.

The processing of the detected R wave begins with block 266 which indicates the value in location CRR is transferred to location PRR, and the value in ACS is transferred to location PACF in this patient's P.P.F. Then according to block 268, the last R-R interval is computed and stored in the R-R file and in location CRR in this patient's P.P.F. The R-R interval is computed by determining the number of times ACQ program 192 was performed between the last time this situation occurred and the present time and the value stored and the R-R file and location CRR (as well as the value transferred to PRR at block 266) will be a number, which, when divided by 120, gives the number of seconds between detected R waves. At the same time, the stored values used to compute the R-R interval are updated so that future R-R interval values may be determined.

L2 routine 246 continues with block 270, which indicates the ST value is again checked. If it is not equal to 2, then the lesser of the values (1) (−TRR/2) + 6 or (2) −54, are stored in the CPYFLG location in that patient's P.P.F., as indicated by block 272 and a jump to NXT routine 286 occurs, as indicated by block 274. However, if the ST value is equal to 2, block 276 indicates that the PC2 counter is incremented and then, according to block 278 a check is made to determine whether the PC2 value is equal to 0. If the PC2 value is nonzero, a jump to the NXT routine 286 is indicated by block 274. If should be recalled that the PC2 value initially had been set to minus nineteen in ATTACH program 174, shown in FIG. 8. Thus, before PC2 equals 0, 19 R-R intervals will be stored in the R-R file. It should also be noted that the R-R file is only 18 character file and that the first value stored therein will be overwritten by the 19th R-R interval value. This is because when the first R wave is detected the value calculated for the R-R interval will not have been based on then existing clock settings, but rather, preexisting ones, and thus will not be accurate. Accordingly, with the overwritten first value, there will be eighteen true values of the R-R intervals in the R-R file.

After 19 R waves are detected, block 276 increments the PC2 value to 0, and after the determination of this at block 278 block 280 indicates that the PHASE2 program, shown in FIG. 7C is scheduled for execution at the next available time. Then, according to block 282, the ST value is reset to 0, just in case ACQ program 192 is executed prior to or interrupts the completion of the PHASE2 program. At this point, block 284 indicates a jump to L4 routine 304 and the sampled value for the next patient number is then applied to computer 20 and the appropriate processing occurs therefore. This is repeated until all eight sampled values are processed.

If the determination made at block 248, 250, 262, 270 or 278 in L2 routine 246, shown in FIG. 7B, had resulted in a jump to NXT routine 286, a determination is made whether or not COPY program in FIG. 11 should be scheduled for execution. Block 288 first checks to determine whether the value in the NUL location of this P.P.F. is 0. If NUL equals 0, a jump to block 292 occurs. If NUL is not 0, then the value in NUL is incremented by 1, as indicated by block 290. Then, according to block 292 a determination is made whether the value in the CPYFLG location of this P.P.F. equals 0, and if so, a jump to L4 routine 304 occurs and the next sample value is not equal to 0, then after the determination at block 292, the CPYFLG value is incremented, as indicated by block 294, and another determination is made whether CPYFLG value is equal 0, as indicated by block 296. If at this time the CPYFLG value is still not equal to 0, a jump to L4 routine 304 occurs. However, if at block 296, the CPYFLG value equals 0, block 298 indicates a determination is made whether the ST value equals 5 and, if so, block 302 indicates the COPY program in FIG. 11, is scheduled for execution. Thereafter, L4 routine 304 is performed, causing the sampled value for the next patient to be processed or a return to the executive program to occur, as may be the case.

If at block 300, it was determined that the ST value was not equal to 5, then block 302 indicates that a determination is made whether the value in the CRR location is less than 0.87 times the value of TRR. If the CRR value is greater than 0.87 TRR, then block 302 is performed, as indicated above, however, if the CRR value is less than, or equal to 0.87 TRR, block 302, which schedules COPY for execution, is skipped and a continuation with L4 routine 304 results. The reason for this determination is to insure no ectopic beats are processed by the COPY program during acquisition, because such beats would make the acquired data inaccurate.

It should be noted from blocks 270 and 272 in FIG. 7B that the CPYFLG value will not be set when the ST equals 2, is an immediate jump to L4 routine 304 occurs from block 292 prior to the execution of the PHASE2 program in FIG. 11, until after the PHASE2 program 232 has been executed.

Referring now to FIG. 10, PHASE2 program 358 will now be described and includes blocks 360 through 386 (even numbers only). Block 360 indicates that a check of the acquisition flag is made to determine whether an acquisition is still underway. If for some reason the acquisition is no longer occurring, block 362 indicates a return to the executive program occurs. Assuming that the acquisition is still underway, block 364 indicates that the average, or mean, R-R interval value for the 18 values stored in the R-R file is then found. This is found by taking the average of the middle 16 of those 18 values, or in other words the highest value and the lowest value of the last 18 R-R interval values stored in the R-R file are discarded. Also according to block 364, the rhythm of the patient's heartbeat is found by calculating the standard deviation of the rate.

Block 366 then indicates that a determination is made whether the mean R-R interval value is greater than 30 beats per minute and less than 240 beats per minute, as these are the limits which system 10 can comprehend. In the event that the determination made in block 366 is that the patient's heartbeat is less than 30 beats per minute or greater than 240 beats per minute, then block 368 indicates that this patient's P.P.F. and acquisition flag are all cleared and then, according to block 370, printer 36 prints

"CANNOT ACQUIRE __,__ __ __ __ __ __ __ __ __".

Block 372 then indicates a return to the executive program.

However, assuming that the determination at block 366 is that the heart rate was between 30 and 240 heartbeats per minute, then block 374 indicates that the mean R-R value calculated at block 364 is stored at the TRR location. Thus, the TRR value is equal to an average value of the rate during acquisition, with the value being in terms of executions of ACQ program 192. It is this TRR value that is used for storing values in the NUL and CPYFLG location at block 258 and 272 in FIG. 7B, previously discussed, when the ST value equals 3 or more.

FIG. 10 continues with block 376 which indicates that the RHYTHM location in this patient's P.P.F. is set to a value equal to the greater of: (1) the standard deviation of the R-R value calculated at block 364; (2) ⅛th of the mean R-R value stored in the TRR location; or (3) 10. This value will be the value of the patient's heart rhythm and is set to the greater of the above noted three values to minimize rhythm errors detections for a patient having steady rhythm. The program continues with block 378, which indicates that the cumulation buffer CB is then cleared for use during the COPY program shown in FIG. 11. Block 380 indicates that the location PHCNT is set to a value of −16 and block 382 indicates that the ST value is set equal to 3. Block 382 indicates the real time at this point is then stored in location RTIM to indicate the time the TRR rate was last set. At this point, block 386 indicates a return to the executive program occurs.

When ACQ program 192 processes sampled values every 120th of a second after PHASE2 program 338 is executed, it does so with the ST value equal to 3. This changes the previously described ACQ program 192 processing after block 254 in FIG. 7B, in which case a value equal to −TRR/4 is placed in the A register rather than −36, and which value, in turn, is placed in the NUL location. This means that once the maximum autocorrelation number has been detected, a second maximum cannot be detected for ¼th of the TRR interval following the time at which the autocorrelation number is less than the value in the location THR. The fact that the ST value equals three also causes the determination made at block 270 to be such that block 272 is executed and the lesser of the values (1) (−TRR/4) + 6, or (2) −54, is stored at the CPYFLG location. Thereafter, whenever a branch to NXT routine 286 occurs, the NUL value is incremented until it is equal to 0. Similarly the CPYFLG value is incremented until it equals 0 at which time the COPY program in FIG. 11 is scheduled for execution by block 302. The result of setting the CPYFLG location in the manner described is that the COPY program is scheduled for execution ½ an interval after the QRS complex is detected.

The effect of incrementing the negative counts in the CPYFLG and NUL locations can be more easily understood by again referring to FIG. 2. After the point 388 has been sampled at sample time 56 and stored in the proper data buffer location and the D0 location, the autocorrelation value for the sample values 388, 390, 392, 394, 396 and 398 taken at respective sample times 46, 48, 50, 52, 54 and 56, is found by multiplying these sample values, reduced to 0 means, times corresponding values, reduced to 0 means, stored in the F1 through F6 storage locations in the patient's P.P.F. The value of this calculated autocorrelation value is less than the previous calculated autocorrelation value (the maximum autocorrelation value), which, of course, would have been calculated by finding the products of the corresponding sample values at sample times 45, 47, 49, 51, 53 and 55. Further, the value of the previously calculated autocorrelation value exceeds the THR value, previously established. Accordingly, the determinations made in blocks 248 and 250 are both affirmative and the test then made at block 254 indicates the ST value equals three, so according to block 258, a number equal to −TRR/4, is placed in the NUL location. For wave 63 in FIG. 2, TRR equals 100, so the NUL location is set equal to a value of −25. Since the NUL value prior to this time has been decremented to 0, FIG. 7B continues through blocks 268 and 270 to block 272, which indicates that a number equal to (−TRR/2) + 6 or −54, whichever is smaller, is placed in the CPYFLG location. In the assumed example, the number −44 is placed in the CPYFLG location.

After the next sample is taken 120th of a second later and ACQ program 192 is performed, an autocorrelation value for points 47, 49, 51, 53, 55 and 57 is found. Again the previous autocorrelation value (found from points 46, 48, 50, 52, 54 and 56) will be greater than the then calculated autocorrelated value, with both still being above the THR value. Accordingly, the NUL value will again be set to −25 by the action at blocks 258 and 260. However, the value in CPYFLG will not be reset since the test this time at block 262 indicates the A register does not have a 0 count and thus, block 272 is never reached for this sample due to block 264 causing a jump to NXT routine 286. In NXT routine 282, the value previously stored in the CPYFLG location will be incremented towards 0, at block 294.

However, after a few more sample times, the autocorrelation value will fall below the THR value and will remain there for the duration of the samples taken on the particular beat shown in FIG. 2. At this point the test made at block 250 will result in a jump to the NXT routine 286. Then, the number in the NUL location will no longer continually be reset, and thus can be incremented, according to block 290, until such time as it equals 0. Thereafter, the test at block 288 on subsequent ACQ program 192 executions will cause block 290 to be skipped, and the value in the NUL location will remain 0 until set again after the next QRS complex is detected.

The result accomplished by incrementing of the NUL value to 0 is that any maximum point of the electrocardiac wave in which the autocorrelation number exceeds the THR value will not be processed as a QRS complex during the time the NUL value is nonzero. For instance, in any electrocardiac wave, the T wave shown in FIG. 2 will be a large magnitude wave which, but for the NUL technique, would be detected as another QRS complex. The same thing would be true of any stray pulse following the QRS complex, whether or not the stray pulse is due to heart action or due to noise.

During the whole time that the NUL value was set, reset and incremented to 0, the CPYFLG value is incremented to 0, as indicated by block 294. It should be recalled that after sample time 56, the CPYFLG value was set to −44. Thus, it will not be until sample point 100 is made that the CPYFLG value will be 0, and only at that time will the test performed in block 296 allow the COPY program in FIG. 11 to be scheduled for execution. Thus, the COPY program is executed ½ of an interval following the detection of the R wave, or the peak value, of the PRS complex. It should be noted that in the event the R-R interval is greater than 1 second, then a COPY program is executed 60 sample times, or ½ second after the detection of the R wave rather than ½ an interval thereafter. This, as will be explained hereafter, is because the system is set up to compare one entire heartbeat wave, up to maximum of 120 sample times in duration, against the master image.

Referring now to FIG. 11, COPY program 400 which was scheduled for execution at block 302 in FIG. 7B, will now be described. COPY program 400 includes blocks 402 through 498 (even numbers only) and is divided into the basic COPY routine, the M4 routine 432 and MON routine 466.

The only time COPY program 400 can be scheduled for execution is only half a beat after a QRS complex for a particular patient has been detected. Block 402 indicates that this detection is communicated to the outside world by causing the proper one of the QRS lights 48 to blink. This may be done by causing computer 20 to send a signal over line 52, which signal controls circuit 44 to turn on and then off the proper light. This signal also resets the failsafe unit 46. Thus, as long as QRS complexes are detected, failsafe are detected, failsafe unit 46 is continually reset before the time it will alarm. This is the primary manner in which failsafe unit 46 is reset. It should be recalled that in the event no patients are being monitored, failsafe unit 46 is reset at block 318 in ACQ program 192 and in the event all beds being monitored had lost EKG conditions, the failsafe unit 46 is reset at block 114 in ARCHK program 88.

Next, a determination is made whether the ST value is equal to or greater than 3, as indicated by block 404. If the ST value is less than 3, block 406 indicates that a return to the executive program occurs. This can happen if the DROP key is depressed just prior to scheduling COPY program 400, thereby setting ST to 0. However, assuming the ST value is equal to or greater than 3, block 408 indicates that the most recent effective interval number of sample values, each reduced to a 0 mean, is transferred from the data buffer in patient's P.P.F. to the work buffer. As used in this detailed description, the term "effective interval number" means the lesser of (1) the mean R-R interval value stored in the TRR location, or (2) 120. In the case of wave 62 shown in FIG. 2, the effective interval number is 100. To accomplish the function of block 408, each of the last effective interval number of sample values made on wave 62, which values are stored in the data buffer in that patient's P.P.F., are added together and thereafter divided by the effective interval number, whereby the mean value of these sample values is determined. Thereafter, each of the effective interval number of values has the determined mean value subtracted therefrom in a given order, with the remainder being stored in a corresponding ordered location of the work buffer in the working memory. The data stored in the work buffer is called the current image because it represents the data from the most recent occurring heartbeat. During monitoring, it is this image that is compared against the master image to determine whether a morphological change in the signal has occurred.

Next, block 410 indicates that the ST value is again checked. If it is less than 3, block 412 indicates a return to the executive program takes place. If the ST value is greater than three, a jump to M4 routine 432 is indicated by block 414. If at block 410, ST value is determined to be equal to 3, then according to block 416, each of the current image values in the work buffer is added, point by point, to the corresponding value in the cumulation buffer and the sum is stored in the cumulation buffer. It should be recalled that the cumulation buffer was cleared at block 378 in PHASE2 program 358, shown in FIG. 10. Block 418 then indicates that the PHCNT value is incremented. It should be recalled that this value was set to −16 at block 380 in PHASE2 program 358, shown in FIG. 10. Block 420 indicates the value in the PHCNT location is then determined. If it is not equal to 0, then block 422 indicates a return to the executive program occurs and this above process is repeated until 16 QRS complexes have been so processed.

After 16 QRS complexes have been processed, as described above, each of the locations of the cumulation buffer CB will contain the point by point sum of corresponding points of each of the last 16 beats. At this time, the test at block 420 indicates that the PHCNT value is equal to 0 and FIG. 11A continues with block 424, which indicates that each of the values in the cumulation buffer are divided by 16 to determine the mean value of corresponding sampled values for the last 16 beats. Thereafter, the sum of each of the values in the cumulation buffer, as divided, is found and this sum is divided by the effective interval number, in or in other words, the mean value of all of the values in the cumulation buffer is found. Then, each of the values in the cumulation buffer is transferred, one by one, reduced to 0 mean, to the master image storage locations in this patient's P.P.F. These values constitute the patient's master image and, as will be explained hereinafter, serve as the values against which corresponding sampled values for subsequent heartbeats are compared.

Block 426 indicates that the ST value is then set equal to 4 and the PHCNT location is set equal to a count of −18. Block 428 indicates that the deviation table pointer is then reset to point to the first location in a 72 word deviation table. The deviation table pointer is then reset to point to the first location in a seventy two word deviation table. The deviation table is divided into four groups of 18 locations each, with each group being for one of the PR, QR, ST and T contour intervals shown in FIG. 2. This table is used to store the cumulative deviation of each contour interval for each wave during the next 18 detected beats. Finally, block 430 indicates that a return to the executive program then occurs.

After the next QRS complex is detected and COPY program 300 is scheduled, the test at block 410 indicates that the ST value is now greater than three, and thus, a jump to M4 routine 432 occurs. This occurs, as previously explained with respect to block 408, with each of the values in the work buffer being from the patient's most recent beat, which values are reduced to a 0 mean. Block 434 in M4 routine 432 indicates that four contour interval counters PCNT, QCTN, SCNT and TCNT are respectively set to counts equal to the negative of the number of samples taken during each of the respective PR, QR, ST, and T contour intervals, shown in FIG. 2. As previously discussed, the QR contour interval is equal to the time required for 20 samples to be made so the value set into contour interval counter QCNT is −20. In the same manner, the value set into SCNT contour interval counter is −4, and the value set into the PCNT and TCNT contour interval counters is equal to −½ of the remaining number of samples made during the effective interval and this may be simply (−effective interval/2) + 12

In the case shown in FIG. 2, those values will each be −38. Next, according to block 436, the four deviation counters, which are respectively called as PDV, QDV, SDV and TDV, and generally referred to in FIG. 11A as "DV", are all set to a count of 0.

According to block 438, the absolute value of the difference between corresponding sample values of the current image, which are stored in the work buffer, and the master image for this patient, which are stored in the master image buffer in this patient's PPF, is found and is added to the value in the proper one of the deviation counter PDV, QDV, SDV or TDV and the sum is then stored in that deviation counter. The proper deviation counter is the one of the PR, QR, ST or T contour intervals from which the particular sample value was taken. For wave 62 shown in FIG. 2, the cumulative absolute deviation on a point by point basis between the current image in the work buffer and the master image in the patient's P.P.F. for the first 38 sample values is stored in the PDV deviation counter. Similarly, the cumulative absolute deviation for the next 20 sample values is stored in the QDV deviation counter, the cumulative absolute deviation for the NXT four sample values stored in the SDV deviation counter and the cumulative absolute deviation for the last 38 sample values is stored in the TDV deviation counter. This procedure utilizes the values set into the counter interval counters at block 434. By doing this for the effective internal number of sample values for a given beat the cumulative deviation for each contour interval PR, QR, ST, and T, is found and stored in the respective one of the deviation PDV, QDV, SDV and TDV.

Next, according to block 440, ST is again checked to see if it equals 4 or 5. If ST equals 5, then block 442 indicates that a jump to the MON routine 466 occurs. If ST equals 4 at the determination in block 440, then block 444 indicates that the values stored in the four deviation counters, PDV, QDV, SDV and TDV are transferred to the deviation table. As previously noted with respect to block 428, the pointer for the deviation table was set to the first location thereof, which is location 0. At this point, the value in the PDV deviation counter is stored at location 0 of the deviation table, the value of the QDV location is stored at location 18 of the deviation table, and the value in TDV deviation counter is stored at location 54 of the deviation table. The deviation table pointer is then incremented to prepare for storing the cumulated deviation during the next detected heartbeat and the value of PHCNT is incremented, as indicated by block 446. Then, as indicated by block 448, the value of PHCNT is checked; if it is not equal to 0, block 450 indicates that a return to the executive program occurs.

At this point ACQ program 192 is again scheduled for performance every 120th of a second until such time as COPY program 400 is again scheduled for execution ½ cycle after the next QRS complex is detected. Thereafter, the above described events take place with the exception that at block 444 the cumulated deviation values in the particular deviation counters PDV, QDV, SDV and TDV are stored at respective locations 1, 19, 37, and 55 of the deviation table. This continues until 18 QRS complexes have been detected, at which time in block 444 the cumulative deviation values for each of the four contour intervals are stored in locations 17, 35, 53 and 71 of the deviation table. At this point, the value of PHCNT is then incremented to 0 at block 446 and the determination at block 448 indicates a continuation with block 452, where the mean deviation value for each of the 18 contour intervals deviation values PDV, QDV, SDV, and TDV stand in the deviation table is found. Then, each mean deviation value is multiplied by four, and stored in the respective location PLIM, QLIM, SLIM and TLIM in this patient's PPF, which locations constitute the deviation limit table. The mean deviation value is calculated by determining the average value of the middle 16 of the 18 stored cumulative deviation values in the deviation table for each contour interval.

Next, according to block 454, ST is set equal to 5, which indicates that the acquisition phase is complete and henceforth a monitoring of each beat occurs by comparing it with the previously established master image. Then according to block 456 the event counter is started. Henceforth, it will be incremented each time the execution of COPY program 400 occurs after a QRS complex is detected. It should be recalled that ARCHK program 88, shown in FIG. 5, checks and resets the event counter every 3 seconds to determine whether it is 0 in an attempt to detect a lost signal.

Next, according to block 458, the LOHIST value is set to the maximum value of 32,767 and the HIHIST value is set to the minimum value of −32,768. Next, according to block 460, printer 36 prints the message "Monitoring —,— — — — — — — —"

to indicate the acquisition phase has been completed and the monitoring phase is to begin. Next, according to block 462, the acquisition flag is cleared to indicate that this acquisition is completed and to allow another patient to be acquired. Finally, block 464 indicates that a return to the executive program occurs.

After the next QRS complex has been detected and COPY program 400 has been scheduled for execution, the effective interval of the sample values will be transferred to the work buffer and each of the contour interval counters will be set to the appropriate values, as indicated by blocks 408 and 434. Further, the deviation counters will be cleared and the cumulative deviations in each contour interval will be stored therein, as indicated by blocks 436 and 438. Finally, block 440 indicates that jump will occur to the MON routine 466 which controls the monitoring.

Figure 11A:
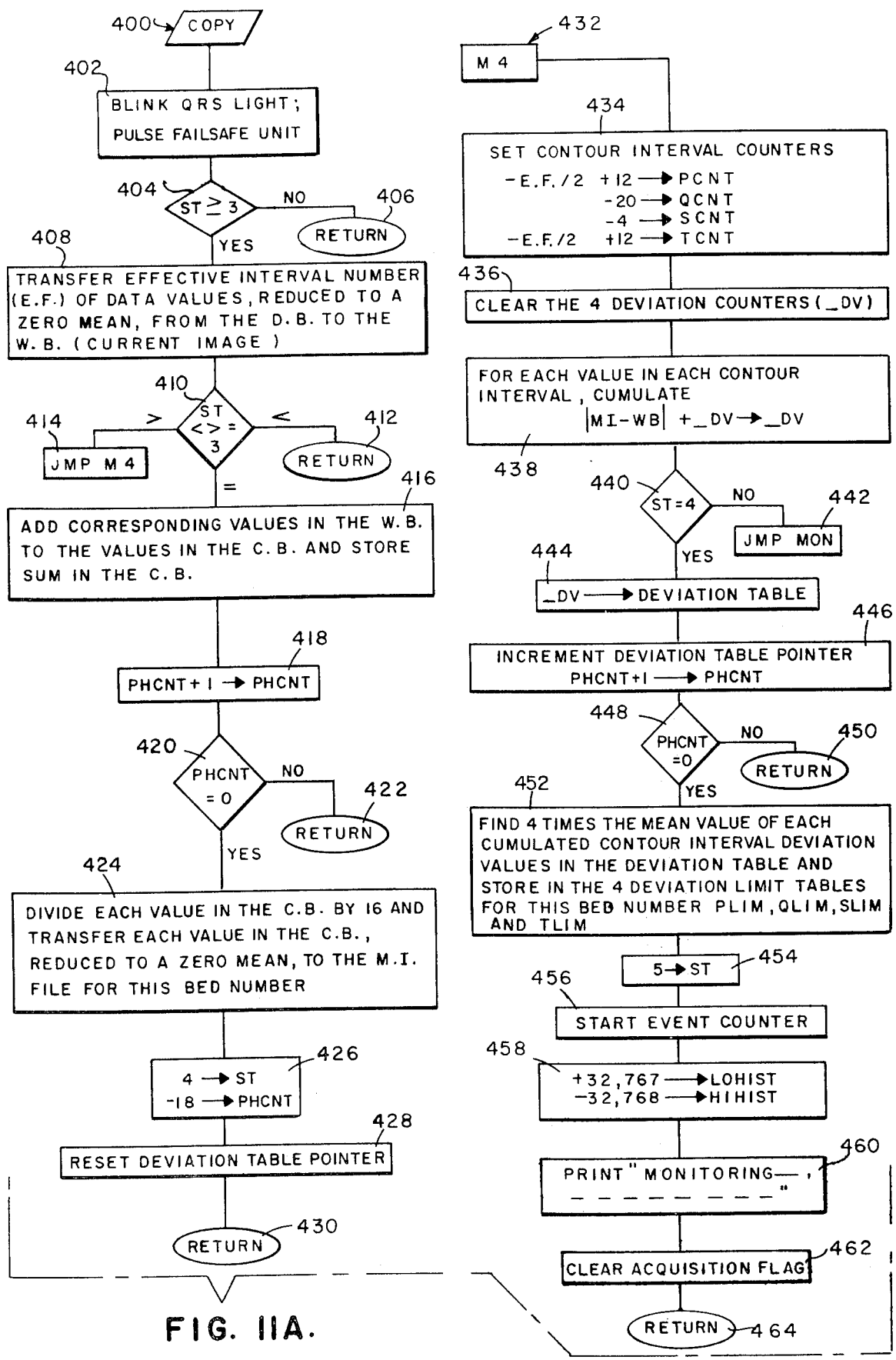
FIGS. 11A and 11B show a flow diagram of the COPY program used to store the master image of the electrocardiac signal during acquisition, and further, to monitor that signal after acquisition has been completed.
Figure 11B:
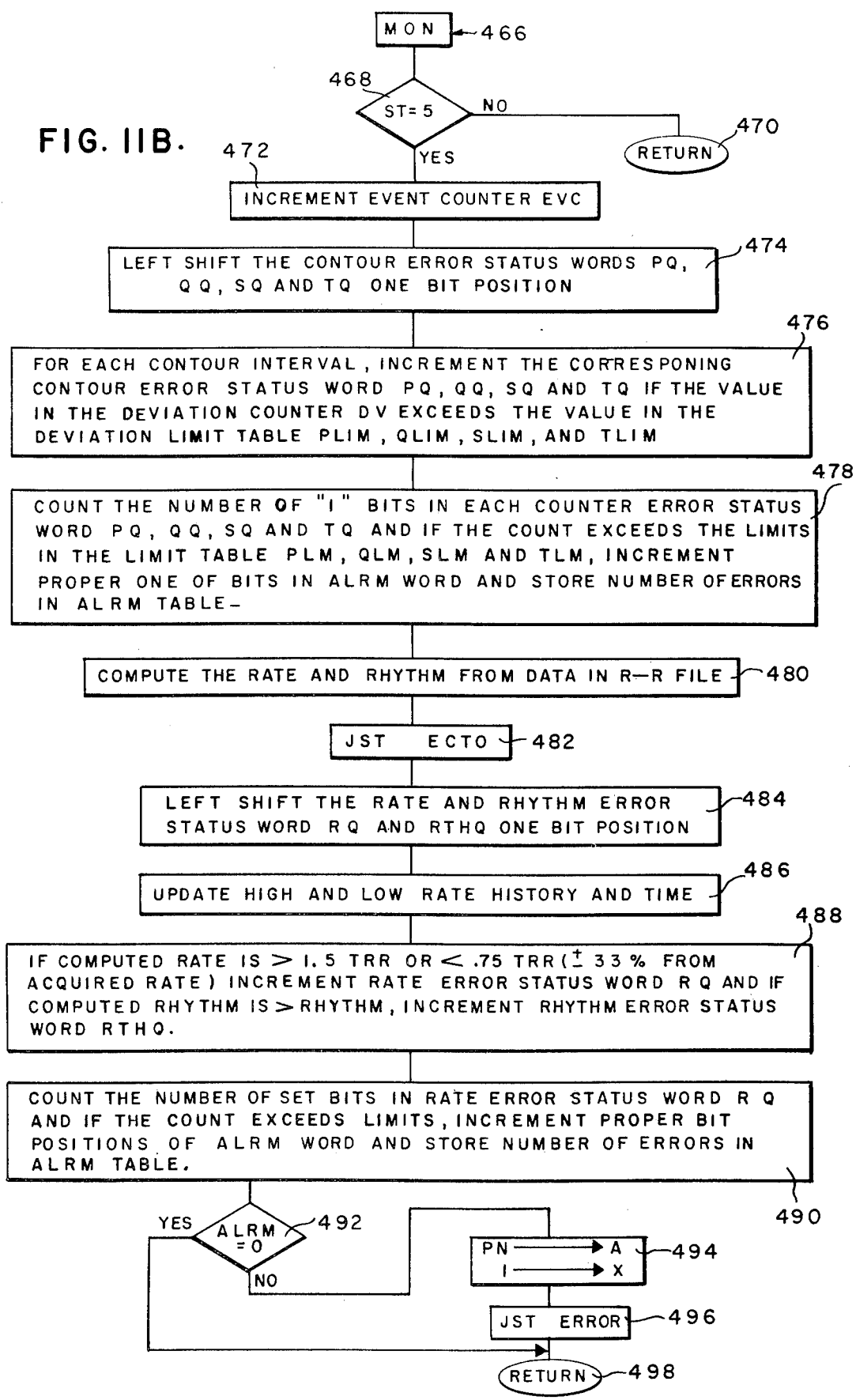

Referring now to FIG. 11B and MON routine 466, the first determination made at block 468 is whether ST is set to 5. If it is not, a return to the executive program occurs, as indicated by block 470. Assuming ST is 5, indicating a monitoring situation, then block 472 indicates that the event counter is incremented. Next, block 474 indicates that each of the four contour interval error status words PQ, QQ, SQ, and TQ is left-shifted one bit position. It is these words in which the occurrence of an error in any portion of a heartbeat is indicated. Each time a new beat is detected, each of the bits in each of the four contour error status PQ, QQ, SQ, and TQ words is left-shifted with the most signigicant bit thereof being lost and the least significant bit being set to zero. If the cumulative deviation for any particular contour interval exceeds the previously calculated deviation limits stored in the deviation limit table PLIM, QLIM, SLIM and TLIM, then the least significant bit of that contour interval error status work is set to one. Thus, a determination of the number of errors occuring in the last 16 beats can easily be made by merely counting the number of one bits in each contour interval error status word PQ, QQ, SQ, and TQ.

Block 476 indicates how this is done. Each respective error contour interval deviation counter PDV, QDV, SDV and TDV is compared against the corresponding contour interval deviation limit table PLIM, QLIM, SLIM and TLIM value previously calculated and stored, as indicated at block 452 in FIG. 11. If the value in the deviation counter exceeds the corresponding value in the deviation limit table, then the corresponding contour error status word PQ, QQ, SQ, and TQ is incremented. Next, according to block 478, the number of one bits in each contour error status word is counted and if the count in any one exceeds the limits stored in the corresponding word in the limit table PLIM, QLIM, SLIM and TLIM then a message is to be printed indicating morphological error in the particular contour interval. Whenever a morphological error is found in a contour interval, the corresponding one of the first four bits of location ALRM is incremented and the number of errors detected for each contour interval are stored in the ALRM table following the ALRM location. As will be hereafter explained, the ALRM word and table are used to determine the format of the morphological error message.

Figure 13:
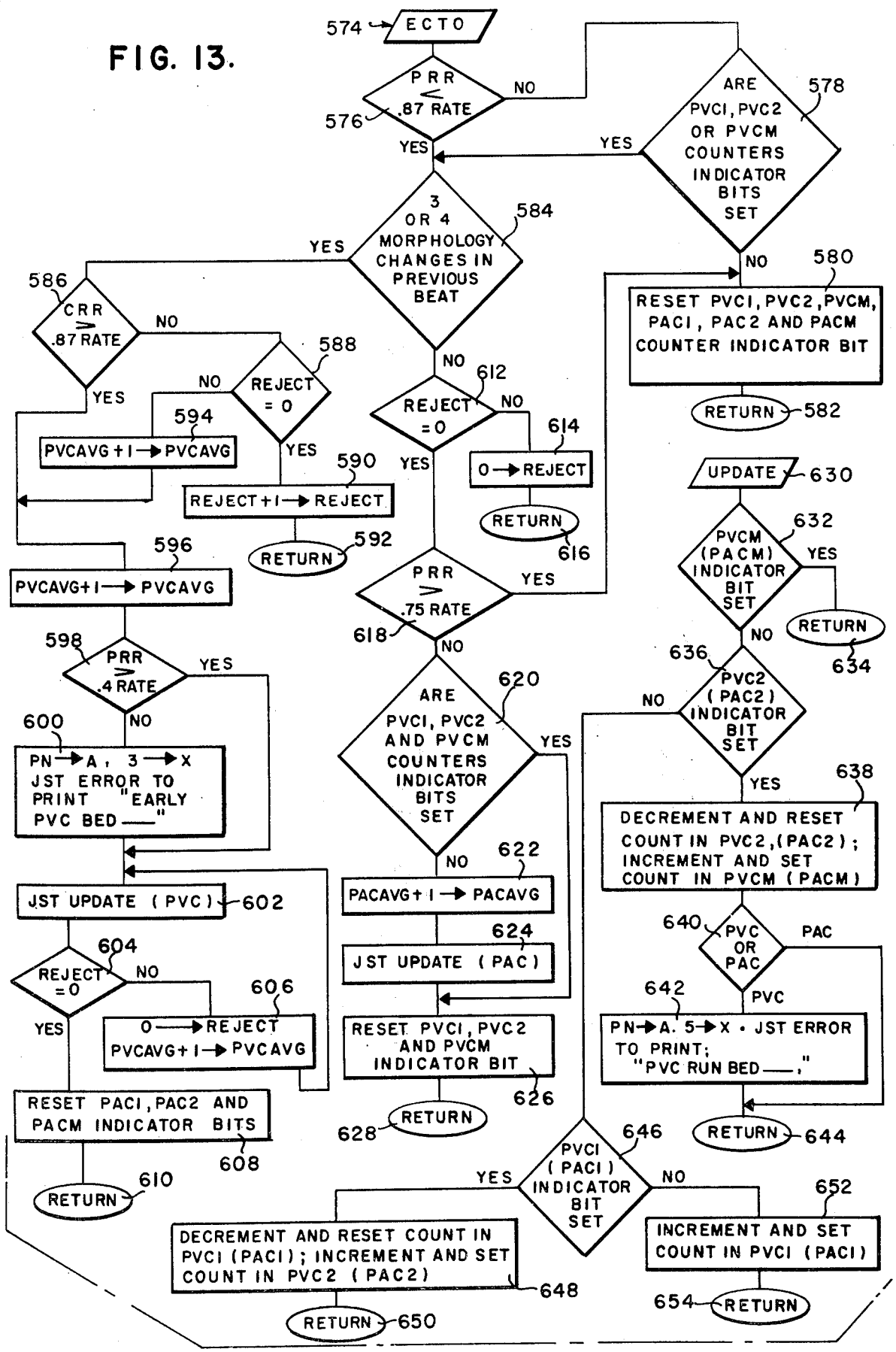
FIG. 13 is a flow diagram of the ECTO program for detecting ectopic beats in the electrocardiac signal of a particular patient.

Next, block 480 indicates that the rate and rhythm are computed from the data stored in the R-R file. It should be recalled that the values stored in the R-R file are equal to the number of times the ACQ program is performed between successive QRS complex detection for the last eighteen such QRS detections. The rate is merely the average value of the middle 16 of the 18 values stored in the R-R file, whereas the rhythm is the standard deviation of the rate. Block 482 then indicates that a jump and store return to the ECTO program shown in FIG. 13 is made. As will be explained hereafter, the ECTO program is used to detect ectopic beats, such as premature ventricular contractions and premature atrial contractions. Block 484 then indicates that the rate and rhythm error status words RQ and RTHQ are each left-shifted one bit position. Block 486 indicates that if the rate just calculated is greater than any previous rate, then the HIHIST word is set equal to this higher rate and similarly, if the rate is lower than any previous rate, then the LOHIST word is set equal to this lower value.

Block 488 indicates that once the rate and rhythm have been determined, they are compared against set values. In the case of the rate it should not vary by more than one-third from the acquired rate TRR or, in other words, the value of the rate calculated at block 480 should be less than 1.5 times the TRR value and greater than 0.75 times the TRR value. If the calculated rate is not within these limits, the rate error status word RQ is incremented. In the case of the rhythm, the calculated rhythm must be less than the value stored in the RHYTHM location by the action indicated at block 376 in FIG. 10. The value stored in the RHYTHM location is the greater of (1) the standard deviation of the acquired mean R-R value, (2) ⅛th of the TRR value, or (3) 10, whereas the computed rhythm value is the standard deviation of the rate during the last 18 beats. In the event that the computed rhythm is greater than the value stored in the RHYTHM location, then the rhythm error status work RTHQ is incremented. According to block 490, the number of one bits in the rate error status word RQ is then counted, and if this count exceeds the limits stored in rate limit location RLIM, then the fifth bit of the ALRM word location is incremented. In any event, the number of one bits in the RQ word is stored in the fifth word of the ALRM table following the ALRM location.

Next according to block 492, a determination is made whether the ALRM word is equal to 0. If the ALRM word is not equal to 0, then block 494 indicates that the patient number is stored in the A register of computer 20 and 1 is stored in the X register of computer 20. Then according to block 496, a jump in store return to the error program, shown in FIG. 17, is indicated. The error program provides the message signal to printer 36, which causes printer 36 to inform the operator of system 10 of the particular error. The number 1 in the X register of computer 20 causes a certain error message relating to morphological change or rate change to be printed whereas other numbers in the X register when the ERROR program is executed cause different messages to be printed. After a return from the ERROR program or if the ALRM word had been determined to be equal to 0 at block 492 thereby indicating no error had occurred, then block 498 indicates a return to the executive program occurs. Thereafter the above procedures are continually repeated as long as ST equals 5.

Figure 12:
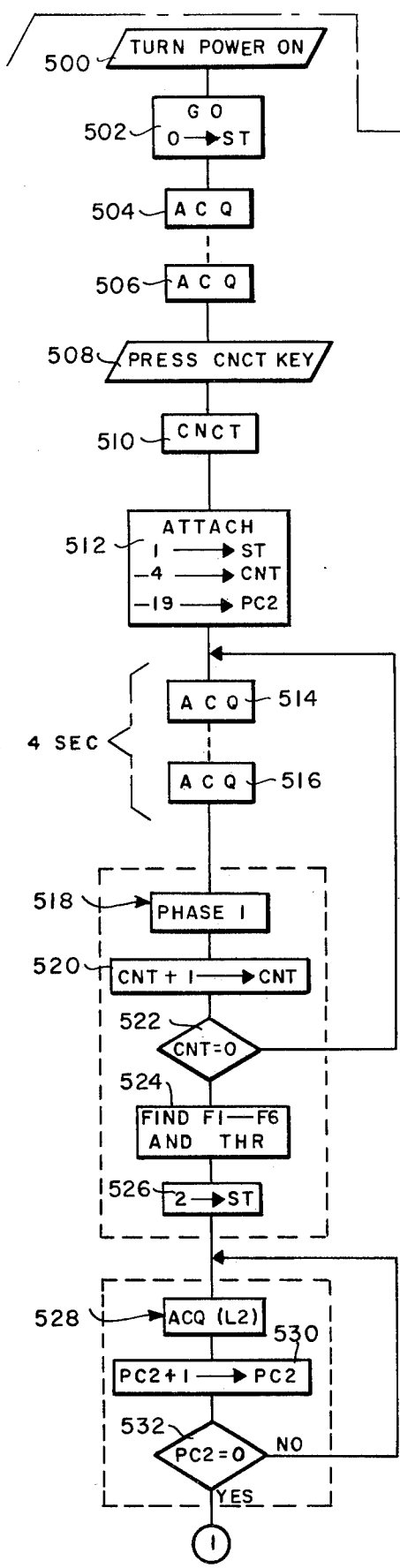
FIG. 12 is a generalized flow diagram showing the process acquiring a patient as described in detail in FIG. 11.
Figure 12:
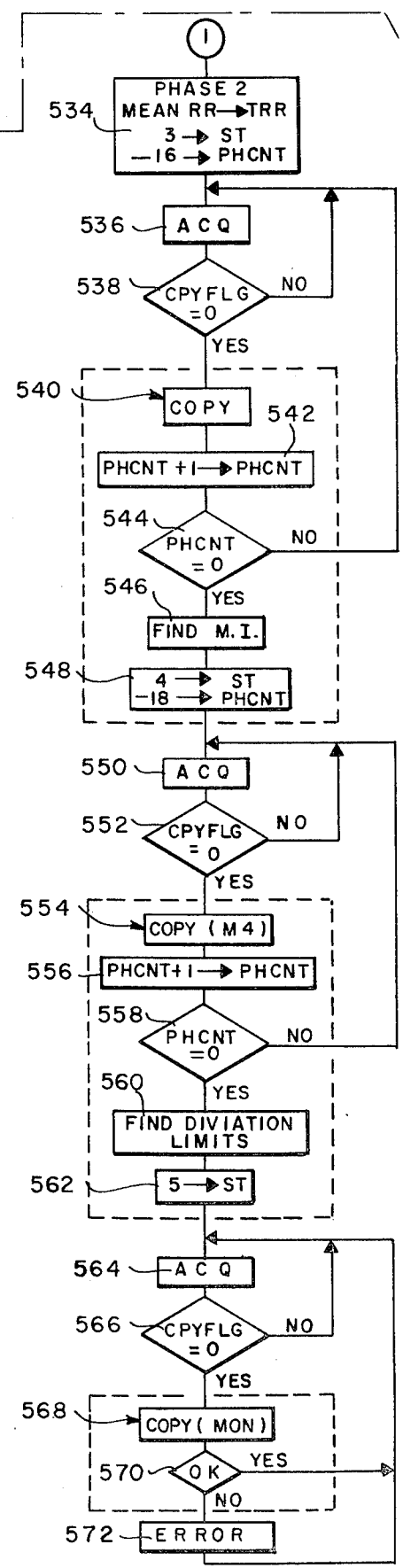

Referring now to FIG. 12, a summary diagram consisting of blocks 500 through 572 of the acquisition and monitoring procedure discussed to this point is shown. The first event which takes place is that the power is turned on, as indicated in block 500. Then, according to block 502, GO program 64 is executed during which time ST is set equal to 0. Thereafter, every 120th of a second, ACQ program 192 is executed, as indicated by blocks 504 and 506.

At the appropriate time the operator of system 10 depresses the ACQ key, followed by a bed number of the patient desired to be connected to the system and the ENTER key, as indicated by block 508. Thereafter, CNCT program 116 is performed, as indicated by block 510, and as indicated by block 512, ATTACH program 174 is then performed. During ATTACH program 174, the value of ST is set equal to 1, the value of CNT is set equal to −4, and the value of PC2 is set equal to −19.

For the next 4 seconds ACQ program 192, with ST equaling one, is continually performed every 120th of a second, as indicated by blocks 514 and 516. After 4 seconds, PHASE1 program 322 is executed, as indicated by block 518. During the execution of PHASE1 program 322, the CNT value is incremented, as indicated by block 520, and a test is made to determine whether or not it equals zero, as indicated by block 522. If not, PHASE1 program 322 is rescheduled to be performed in another four seconds and blocks 514, 516, 518, 520 and 522 are repeated until such time as the CNT value is determined to be 0 at block 522. As indicated by block 524, the F1 through F6 locations are then set to the values which will subsequently be used to find the autocorrelation value, and the threshold autocorrelation value is calculated and stored in the THR location. At that point, as indicated by block 526, ST is set to 2.

Thereafter, the ACQ program 192 with ST equaling two (that is, L2 routine 246) is performed every 120th of a second until such time that 19 QRS complexes have been detected, as indicated by block 528. After each QRS complex is detected, the PC2 value is incremented, as indicated by block 530. This is repeated until 19 QRS complexes are found, as indicated by block 532. Then, PHASE2 program 358 is performed, as indicated by block 534. During the execution of PHASE2 program 358, the mean R-R value is found and stored in the TRR location, ST is set equal to three, and PHCNT is set equal to −16.

Thereafter, ACQ program 192 is continually performed with ST equaling three every 120th of a second until such time as the CPYELG word has been set and incremented to 0, as indicated by blocks 536 and 538. This will occur ½ the effective interval after each QRS complex is detected. Thereafter, as indicated by block 540, COPY program 400 is performed for ST equaling 3. During this time, the value of PHCNT is incremented each time COPY program 400 is executed and the value of PHCNT is checked to see if it equals 0, as indicated by blocks 542 and 544. When PHCNT is nonzero at block 544, another QRS complex will have to be found as indicated by the branch back to block 536. When PHCNT equals 0, 16 QRS complexes will have been found and thereafter, as indicated by block 546, the master image is found. Then, as indicated by block 548, ST is set equal to 4 and PHCNT is set equal to −18.

At this point ACQ program 192 with ST equaling 4 is performed until another QRS complex is detected and the CPYFLG value is incremented to 0, as indicated by blocks 550 and 552. Then, as indicated by block 554, the COPY program 400 with ST equaling 4 (that is, the M4 routine 432 thereof) is executed and the value in the PHCNT location is incremented each time COPY program 400 is executed until such time as it is equal to 0, as indicated in block 560, and ST is set equal to 5 to indicate that the acquisition is complete and the monitoring is to begin, as indicated by block 562.

During the monitoring phase, ACQ program 192 is performed with ST equaling 5 every 120th of a second until a QRS complex is detected and the CPYFLG value is incremented to 0, as indicated by blocks 564 and 566. At this time COPY program 400 is executed for ST equaling 5, (that is MON routine 466 thereof), as indicated by block 568. During this portion, a test is made to determine whether an error condition exists, that is whether the error limit number of the last 16 beats contained either a morphological or rate error therein, as indicated by block 570. If no error condition is indicated then blocks 564, 566, 568 and 570 are repeated for the next beat. However, if an error condition is found at block 570, then the ERROR program showing in FIG. 17, is executed, as indicated by block 572, prior to repeating blocks 564, 566, 568 and 570 again.

Referring now to FIG. 13, ECTO program 574 is shown. It should be recalled that at block 482 the MON routine 466 of COPY program 574 was made to determine whether a premature ventricular contraction or a premature atrial contraction occurred. This jump in store return is made each time a QRS complex is detected and COPY program 400 is scheduled for execution. Before discussing the exact processes defined by ECTO program 574, it is necessary to first understand what is a premature ventricular contraction (hereafter PCV) or a premature atrial contraction (PAC).

A PCV is beat of the heart stimulated by electrical pulses other than normal pulses in which the morphological shape of the electrocardiac signal differs from the shape of a normal beat and further which the occurrence thereof is earlier in time than would be normally expected, given the patient's then occurring rate. PVCs may occur singly or in runs of two or more. In the case of multiple PVCs, only the first in the series will normally be premature, although each of the PVCs will have a morphology completely foreign to the normal morphology of the patient's electrocardiac signal. Normally single PVCs occurring are not considered dangerous in and of themselves; however, runs of three or more PVCs together may be considered dangerous and should be indicated. Further, a PVC occuring during the T wave of the preceding beat, while the heart is recharging in preparation for the next beat, is considered dangerous and its occurrance should be indicated to the operator.

A PAC is a heartbeat which appears early with no substantial morphological change. In the case of a PAC it should appear at least 25% early. PAC's, as such, are not normally considered dangerous; however, it is helpful to know the trend of PACs over a given time period in a particular patient and this information may be meaningful to the physician treating the patient.

Referring to table I previously set out, it is noticed that in each P.P.F. eight word are dedicated for PCV and PAC storage and these words are PVC1, PVC2, PVCM, PAC1, PAC2, PACM, PVCAVG and PACAVG. As previously explained bits 0 through 14 of the PCV1, PCV2, PVCM, PAC1, PAC2, and PACM words are used to cumulative count the number of respective single PCV double PVC's, runs of three or more PVC's single PAC, double PAC's, and runs of three or PAC's. Bit 15 of each of these words is used as an indicator to indicate whether single PVC, a pair of PCV's, a run of three or more PVC's, a single PAC, a pair of PAC's or a run of 3 or more PAC's has just occurred. In the case of the PVCAVG and PACAVG words, the right half of each contains the absolute number or respective PVC's or PAC's which had occurred during the last 4 minutes, or since the ERST program (which is scheduled to be performed every 4 minutes) had been executed. The left half of each of the PVCAVG and PACAVG words in used during the execution of the ERST program shown in FIG. 15 to temporarily store the number of PVC's per minute or PAC's per minute respectively which occurred during the preceding 4 minutes interval.

Referring now specifically to ECTO program 574, it consist of blocks 576 through 654. As indicated by block 576, the first determination made is whether the value stored in PRR location in the P.P.F. is less than 87% of the rate calculated during COPY program 400, just prior to the jump and store return to ECTO program 574. The value in PRR location is equal to the number of times the ACQ program 192 is performed between QRS complex detections for the previous beat. It should be recalled that this PRR value was stored by the action at block 266 in ACQ program 192 at the time the most recent QRS complex was detected. It also should be recalled that at block 266, the number of times ACQ program 192 was executed the two most recently detected QRS complexes is stored in the CRR location as the current R-R interval value. A half a cycle after these two storages occur, COPY program 400 is executed and during COPY program 400, ECTO program 574 is executed. Thus, it is seen that at block 576, the determination made is for the previous R-R value, not the current R-R value found.

If it is determined at block 576 that PRR value is less than 87% of the rate computed during COPY program 400 at block 480, then according to block 578, a determination is made of whether the indicator bit of one of the counters PCV1, PVC2, or PVCM is set. If the indicator bit in these counters is not set, then according to block 580, the indicator bit of each of the PVC1, PVC2, PVCM, PAC1, PAC2 and PACM counters is reset, and according block 582, a return to COPY program 400 occurs.

However, if at block 576 it was determined that the PRR value was less than 87 percent of the rate, or if at block 578 it was determined that one of the PVC counter indicator bits had been set, then according to block 584, a determination is made of whether three or four morphology changes in the four portions of the previous beat had been detected. Again it should be noted, it is the previous beat, not the current beat. This may be accomplished by checking the value of the bit 1 position of each of the contour error status words PQ, QQ, SQ, and TQ which at this time indicates the error status of the previous beat. If at block 584, it is determined that three or four morphology changes in the four contour intervals of the previous beat have occurred, then there is good indication that PVC has occurred. If, in fact, a PVC has occurred, the R-R interval following the PVC beat should be at least as long as a normal duration interval; however, if the early beat, as detected at block 576, with morphology change, as detected at block 584, had been a noise or artifact caused pulse, then the interval between that pulse and the next QRS complex would be less than a normal interval because it occurred between two normal QRS complexes. Thus, according to block 586, a determination is made of whether the value in the CRR location in the P.P.F. corresponding to the duration of the last detected interval between QRS complexes, is greater than 87% of the rate determined at block 480 in COPY program 400.

If it is determined at block 586 that the CRR value is not greater than 87% of the rate, then according to block 588, a determination is made whether the value in the word REJECT in the P.P.F. is equal to 0. If this is the case, then according to block 590 the word REJECT is incremented by one and according to block 592 a return to COPY program 400 results. If at block 588 it was determined that the value in word REJECT was not equal to zero, then according to block 594, the value in the word PVCAVG is incremented by one.

What is being accomplished by the action at blocks 586, 588, 590, 592, and 594 is that in the event the current R-R interval CRR is not approximately of normal duration, then it is assumed that the detected pulse is not a PVC, but rather, noise or artifacts. This assumption is recorded by incrementing the REJECT word. However, if the REJECT word had previously set to a value at one that is, the same assumption wad made for the preceding beat, then this is an indication that both beats are actually PVCs. Thus, block 594 indicates that the PVCAVG word is incremented for the first assumed beat, and a continuation with the normal PVC processing results.

If at block 586 it was determined that the value in CRR was greater than 87% of the rate, or after PCVAVG is again incremented by one. Then, according to block 598, a determination is made of whether the value in PRR location corresponding to the previous R-R interval, is greater than 40% of the then occurring rate. If it is determined that the PRR value is less than 40% of the rate, than the PVC detected is considered an early PVC and should be reported to the operator of system 10. To do this, according to block 600, the patient number is loaded into the A register of computer 20 and the number three is loaded into the X register of computer 10 and a jump in store return to ERROR program, shown in FIG. 17 occurs. This results in printer 36 printing the message

"EARLY PVC BED __,__ __ __ __ __ __ __ __".

The exact manner of how this is accomplished will be explained hereafter in more detail with regard to FIG. 17.

If it is determined at block 598 that the PRR value is greater than 40 percent of the rate, and thus no early PVC has occurred, then block 600 is skipped. Next, according to block 602, a jump in store return in UPDATE (PVC) routine 630 occurs. UPDATE routine 630 is also shown in FIG. 13 and as will be explained hereafter in more detail, sets the indicator bits in the PVC and PAC counter words, as well as incrementing the count in the particular PVC and PAC counter. In block 602, it is noted that "(PVC)" occurs after the word UPDATE. This indicates that UPDATE routine 630 is to operate on the PVC counters only.

Next, according to block 604, a determination is made of whether the REJECT word is equal to 0. If it is determined the REJECT word is not equal to 0 than according to block 606 the REJECT word is reset to 0 and PVCAVG is incremented by one and then a return to block 602 occurs whereupon the jump and store return to UPDATE (PVC) routine 630 again occurs. Upon a return from the UPDATE routine 630 this time, the determination at block 604 will be that REJECT is equal to 0. Then according to block 608 the indicator bits of the PAC1, PAC2 and PACM counters are reset to 0. This is because a PAC can not occur when a PVC occurs, and this procedure clears prior indications of PAC's, if any. Finally, according to block 610 a return to COPY program 400 occurs.

If at block 584, it was determined that no morphological change had occurred for the previous beat, block 612 indicates that a determination is made of whether the value in the REJECT word is equal to 0. If the REJECT word is not equal to 0, then according to block 614, the REJECT word is cleared and, according to block 616, a return to COPY program 400 occurs. The sequence of block 612, 614, 616 is confirmation of correctness of the assumption originally made at block 590, where it was determined that the current R-R interval was not greater than 87% of the rate and that the REJECT word had been incremented to assume nonectopic beat detection. Thus, due to the return to COPY program 400 as indicated at block 616, the beat assumed to be due to noise or artifacts at block 590 is ignored, as far as the PVC and PAC counters are concerned.

If at block 612 it was determined that the value in REJECT word was equal to 0, then according to block 618, a determination is made of whether the previous R-R interval PRR is greater than 75% of the current rate. If the PRR value is greater than 75% of the current rate and no morphology changes have occurred in the previous beat, then there are no PVCs and no PACs involved but just an early beat. In this event block 580 indicates that the indicator bit in the PVC1, PVC2, PVCM, PAC1, PAC2 and PACM counters are all reset to zero and, according to block 582, a return to copy program 400 occurs.

However, if at block 618 it had been determined that the PRR value was less than 75 percent of the rate, then the detection of a PAC has occurred. Next, according to block 620, a determination is made of whether the PVC1, PVC2, or PVCM indicator bits are set. If they are not set, than a PAC has been detected and according to block 622, the value in PACAVG word is incremented by one and, according to block 624, a jump in store return to UPDATE (PAC) occurs and the PAC counters and indicator bits are updated. If at block 620 it had been determined that one of the indicator bits of PVC1, PVC2, or PVCM counter had been set, then there would not have been a PAC. In that event, block 622 and 624 would be skipped. Continuing with block 626, either after the determination that an indicator bit is set at block 620 or upon return from the UPDATE (PAC) PAV1, PVC2 and PVCM indicators bits are all reset, if not already reset. Finally, according to block 628 a return to COPY program 400 occurs.

Referring now to UPDATE routine 630 which consists of block 632 through 654, it is used to set the indicator bit and to increment the counts in the PVC1, PVC2, PVCM, PAC1, PAC2, and PACM counters. First, according to block 632 a determination is made whether the PVCM counter, indicator bit, in the case of a JST UPDATE, or the PACM counter indicator bit, in the case of a JST UPDATE PAC is set. If the PVCM or PACM indicator bit is set, it indicates that the last detected PVC or PAC is just one more in a run of three or more PVCs or PACs, for which no further action is required, and thus, according to block 634, a return to the ECTO program 574 occurs. However, if the PVCM or PACM indicator bit is not set, then a determination is made of whether the PVC2 indicator bit is set in the event of a JST UPDATE (PVG) or whether the PAC 2 indicator bit is set in the case of a JST UPDATE (PAC). If at block 536, it is determined that the PVC2 or PAC2 indicator bit is set, thereby indicating a pair of PVC or PAC detection had occurred just prior to the present detection, then according to block 638 the count in proper one of the PVC2 or PAC2 counters is decremented and the indicator bit therein is reset. Further, the count in the proper ones of the PVCM or PACM counters is incremented and the indicator bit therein is set. Next, according to block 640 a determination is made whether the UPDATE routine 630 is for a PVC or a PAC. If it is for a PVC, then according to block 642, it is desired to indicate to the operator of system 10 that a run of three PVCs has just occurred, that is, that three PVCs in a row have just occurred. This is accomplished, according to block 642, by installing the patient number in the A register of computer 20 and number 5 in the X register of computer 20 and making a jump and store return to ERROR program, shown in FIG. 17, to cause the message

"PVC RUN BED __,__ __ __ __ __ __ __ __"

to be printed on printer 36. In the event a PAC is determined at block 640, or upon return from the ERROR program after block 642, block 644 indicates that a return to ECTO program 574 occurs.

If at block 636 it had been determined that the indicator bit of the proper one of the PVC2 or PAC2 counters had not been set, then according to block 646 a determination of whether the indicator bit of the PVC1 or PAC1, as the case may be, counter is set. If it is determined at block 646 that PVG1 or PAC1 indicator bit is set, then, according to block 648, the indicator bit of the PVC1 or PAC1 counter is reset and the count therein is decremented by one, and the indicator bit of the PAC2 or PAC2 counter is set and the count therein incremented. Next, according to block 650, a return to ECTO program 574 occurs.

If a block 646 it had been determined that the indicator bit in the PVC1 or the PAC1 counter had not been set, then according to block 652, it is set and the count in the PVC1 or PAC1 counter is incremented. Next, according to block 654, a return to ECTO program 574 occurs.

The reason for cumulating the count in the PVCAVG and PACAVG counters at blocks 596 and 622 during ECTO program 574 is to accumulate information regarding ectopic beat occurrence during a 24 hour period and to output, upon command from keyboard 38, and ectopic beat trend history. The cumulation and storage of the data necessary for reporting this trend history is accomplished by two programs, both of which are initially scheduled by GO program 64 during the time power was initially applied to the system. These programs are the ERST programs 656 shown in FIG. 14 which is performed on the hour, as indicated at block 82.

Referring now to FIG. 14, ERST program 656 includes block 658 through 690. First according to block 658, the word CNT in ERST program 656 is set equal to −8. Next, as seen from block 660, P.P.F1 is accessed and, according to block 662, a determination is then made whether the patient whose P.P.F. is then accessed in being monitored by checking the ST value in the P.P.F to see if it is equal to 5. If the patient is being monitored, then according to block 664 the values in the right half of the words PVCAVG and PACAVG are each divided by 4 and stored in the left half thereof.

Next, according to block 666 the value in the left half of the word CURECB is transferred to the word ZAP and the value in the left half of the word PACAVG is added to the contents of the word ZAP and that sum is stored in the right half of the word ARCHK. The word CURECB is used to store the information relating to the ectopic beat history during the current hour, with the left half being used for the number of PACs and the right half being used for the number of PVCs. Next, according to block 668 a determination is made whether the sum just stored in ARCHK is greater than 255, inasmuch as this is the maximum number that can be stored in the right half of the word ARCHK. If the sum is greater than 255, then according to block 670, the number 255 is stored in the right half of the word ARCHK. If not, block 670 is skipped.

Next, according to block 672 the right half of the word ARCHK is shifted to the left half of the word ARCHK, and according to block 674, the left half of the word PVCAVG added to the right half of the word CURECB and the sum is stored in the right half of the word ZAP. It should be recalled from block 664 of the left half of the PVCAVG contains the number of PVCs per minute during the last four minute intervals, whereas the right half of the word CURECB contains the cumulation during the current hour of the number of PVCs per minute which have occurred. Next, according to block 676, a determination is made of whether the sum currently in location ZAP is greater than 255. If it is, then according to block 678, the number 255 is stored in the word ZAP. If not, then block 678, the number 255 is stored in the word ZAP. If not, then block 678 is skipped and the true value of the sum remains stored in loaction ZAP. Again, the reason for this is that the maximum value which can be stored in eight bits is 255.

Thus, at this point, the word ARCHK contains in the right half the number of PACs per minute which have occurred during the current hour and the word ZAP contains in the left half, the number of PVCs per minute which have occurred during the current hour. Then, according to block 680, the words ZAP and ARCHK are added together with the sum being stored and the word CURECB, which now contains, in the left half, the number of PVCs per minute during the current and, in the right half, the number of PACs per minute during the current hour. Next, according to block 682, the value in the word PVCTIM is incremented by four. The value in PVCTIM is equal to the number of minutes during which PVCs have been counted. Since ERST program 656 is called every 4 minutes, then PVCTIM must be incremented four times at block 682 to maintain current numbers of minutes stored therein.

If at block 662, it had been determined that the patient whose P.P.F. had been accessed was not being monitored, then a skip to block 684 would occur, which, in any event, is performed after block 682. According to block 684, the next patient's P.P.F. is accessed and the value M location CNT is incremented by 1. Then according to block 686 a test is made to determine whether the value in the CNT location is equal to 0. If it is not, a return to block 662 is indicated and the preceding step 662 through 686 (even numbers only) for the next patient are again performed. This continues until all eight patients have had their ectopic beat counts updated for the preceeding 4 minute interval, at which time the value in location CNT will be equal to 0.

Then, according to block 688, ERST program 656 is scheduled to be performed again in 4 minutes. Thus, it is seen that ERST program 656 will be performed every 4 minutes because it rescheduled itself after its completion. Finally, according to block 690 a return to executive program is indicated.

During a given hour, ERST program 656 will have been executed 15 times. On the hour, the executive program automatically schedules HPLY program 692, shown in FIG. 15. HRLY program 692 consists of blocks 694 through 708. First, according to block 694, the value −8 is inserted into the CNT location therein and P.P.F.1 is accessed. Then, according to block 696 a determination is made of whether the patient for the access P.P.F. is being monitored. This may be done by checking the ST value in that accessed P.P.F.

Next, according to block 698, the cumulative count of PACs per minute stored in the left half of the word CURECB are divided by 15 and stored in the left half of the word ZLOG. Further, the cumulative count of PVC per minutes stored in the right half of the word CURECB is divided by 15 and moved to the right half of A register. Then the A register and the ZLOG word are added and stored in the ZLOG location. Thus, the ZLOG location contains in the left half, the average number of PACs per hour during the last hour. Next according to block 700, the contents of the ZLOG location are stored in the ECBHIS table at the location set aside for the last completed hour. The ECBHIS table is 24 words in duration with each word being assigned to a particular hour of a 24 hour day. It should be noted that the time from 12:00 midnight until 12:59 A.M. is the 0 hour and so forth until the time from 11:00 P.M. is the 23 hour. Next according to block 702, the word CURECB is set equal to 0 to begin accumulating new ectopic beat information during the next hour.

If it has been determined at block 696 that the patient for the access P.P.F had not been monitored, or in any event, after block 702, then according to block 704 the P.P.F. for the next patient is access and the value in the CNT location is incremented by 1. Next, according to block 706, a determination of whether the value in the CNT location is equal to 0 is made. If it is not equal to 0, a return back to block 696 occurs and block 696, 698, 700, 702 and 704 and 706 are repeated. If it is determined at block 706 that the value in the CNT location equals 0, then block 708 indicates a return to the executive program occurs.

With this ectopic beat information being accumulated for each patient, it is necessary to provide a method for reporting the information quickly and concisely in a meaningful format to the operator of system 10. As previously mentioned, this may be accomplished by depressing the ECT TRND key on keyboard 38 followed by a number 1 through 8 corresponding to the particular patient 1 through 8 for which the ectopic trend history is requested and the ENTER key. This causes the executive program to schedule REPORT program 710 shown in FIGS. 16A, 16B and 16C to be executed, after previously scheduled programs have been executed. REPORT program provides the information regarding PVGs and PAGs in a histogram format with the S axis being in numbers of ectopic beats during a given hour and the Y axis being time, beginning with the hour 24 hours prior to the most recent complete hour on the left and the most recent complete hour on the right then, for each hour, a "*t*" for a PIC, a "__" for a PAC or a "__" for both is printed at the interaction of the time and number per hour axises.

REPORT program 710 includes blocks 712 through 736 (even numbers only) and has associated therewith REENT program 738 containing blocks 740 through 814 (even numbers). Before proceeding to describe each of the blocks in detail, it is necessary to understand the organization of certain portions of the memory associated with and used by REPORT program 710. First in each patient's P.P.F, there is a 24 word table called ECBHIS, in which each word is associated with the number of PVCs and the number of PACs which occurred during a particular hour. The first word of the ECBHIS table will contain the number of PACs and the number of PVCs during the 0 hour from midnight until 12:59 A.M. The second word contains the number during the first hour from 1:00 A.M. until 1:59 A.M. and so forth until the last word of the ECBHIS table contains the number PACs and PVCs during the 23 hour from 11:00 P.M. until 11:59 P.M. Within REPORT program 710 are also contained several tables, and an output buffer. A message which reads "TWENTY-FOUR HOUR ECTOPK HISTORY BED " is contained in byte format ASCII coding in the MESSAGE table. The TIMBF table contains ASCII coding for the time information, which is used for the X axis. This coding provides a message, such as "N..3..6..9..M..3..6..9..", and represents each of the 24 hour time period. As will be seen hereafter, this message is printed beginning with the dot, letter or number to signify the time beginning with the hour 24 hours preceeding the most recent completed hour at the left and ending with the most recent occurring completed hour at the right.

There is also provided an ASCLIM table which contains ASCII coding for the information to be printed as the Y axis that is, number of PVCs per hour or PACs per hour. These numbers are divided into the nonlinear scale of 0 through 1, 2 through 3, 4 through 5, 6 through 8, 9 through 12, 13 through 16, and 17 and up. There is also provided a LIM table of seven words in length, with each word having two bytes therein, each of which constitute binary code for the limits just described with respect to the ASCLIM table. Finally there is provided an output buffer OUTBUF of 17 words length into which various messages are planned for subsequent transfer to printer 36. The last two words of the output buffer OUTBUF contain a reentrance code and an address to REENT program 730, which causes REENT program 730 to be scheduled for execution.

Figure 16A:
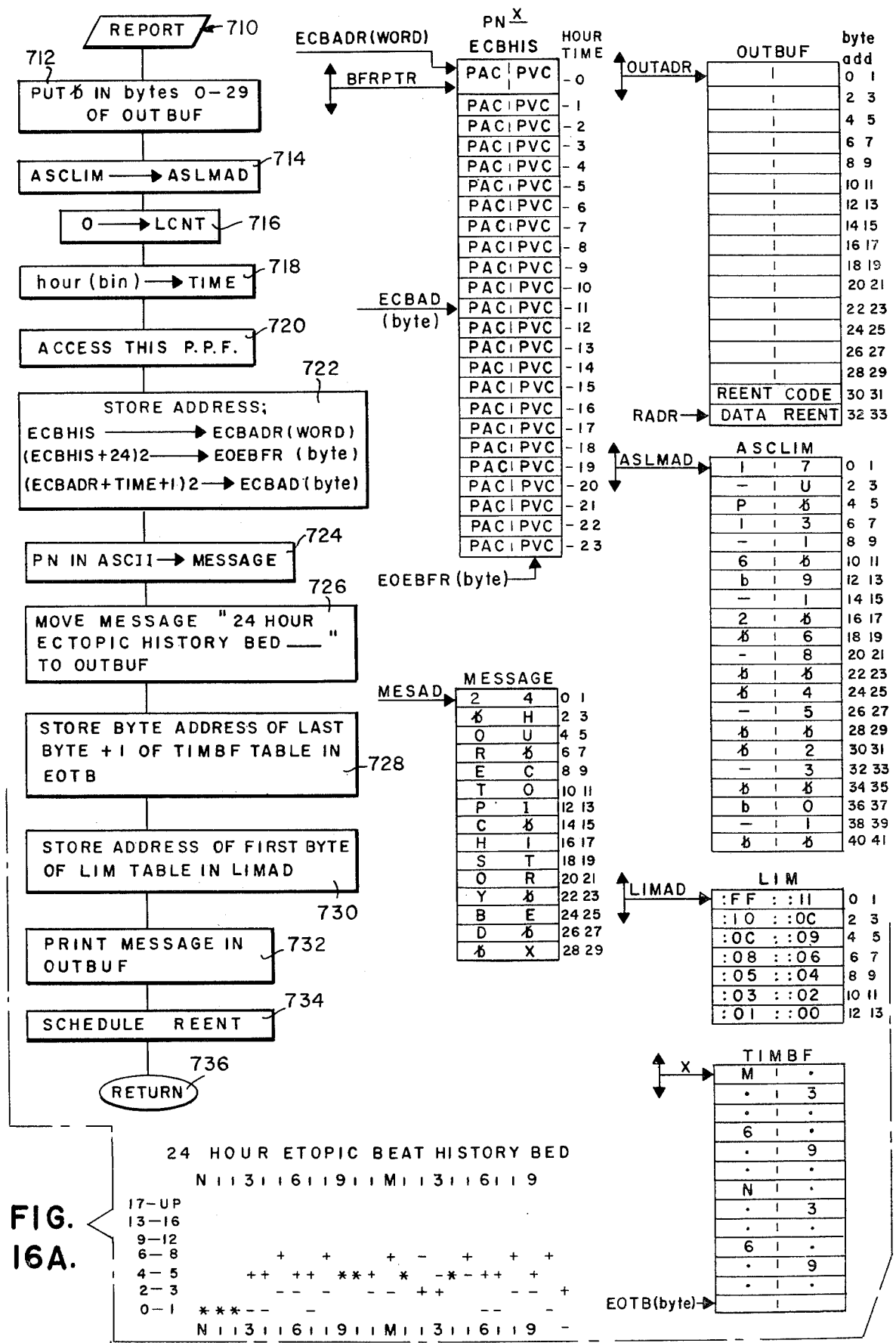
FIGS. 16A, 16B and 16C are flow diagrams of REPORT and REENT programs, which are performed in response to a command entered on the keyboard to provide a histogram of the ectopic history during the last 24 hours.

As will be noted in FIG. 16A, some of the blocks of memory described above contain one or more pointers for addressing individual locations thereof. Each of these pointers will be described in more detail with respect to the detailed description of REPORT program 710, and REENT program 738.

Before referring specifically to REPORT program 710 and REENT program 738 a general statement concerning the overall operation directed by these programs is in order. What will be occurring is a line by line printing of the ectopic beat history histogram. First, the line "TWENTY-FOUR HOUR ECTOPIC BEAT HISTORY BED " will be printed. Then there will be printed the message in the TIMBF table beginning with the complete hour 24 hours preceeding. Thereafter, there will be printed seven lines containing the information found in the ECBHIS ectopic beat history table in the patient's P.P.F. Each of these lines will begin with the next sequential one of the limits stored in ASCLIM table. Finally, their time stored in the TIMBF table will again be printed. It should be noted that each of these lines will be scheduled after the prior line has been printed. In this case occurring in the interim will be printed between the histogram lines, if they are scheduled during the printing of a given line but prior to the end of the completion of the entire histogram.

Referring now specifically to REPORT program 710, block 712 indicates that the ASCII code for a blank is placed for a blank is placed in each of the bytes 0 through 29 of the output buffer OUTBUF. Next the address of the ASCLIM table is moved to the ASLMAD pointer so that the ASLMAD pointer points to byte 0 of the ASCLIM message. As will be hereafter explained, the ASLMAD pointer may be incremented to address any of the bytes 0 through 41 of the ASCLIM message. Next according to block 716, the value in location LCNT is SCT equal to 0 and according to block 718 the current hour in binary, is placed in each of the bytes 0 through 29 of the output buffer OUTBUF. Next the address of the ASCLIM table is moved to the ASLMAD pointer so that the ASLMAD pointer points to byte zero of the ASCLIM message. As will be hereafter explained, the ASLMAD pointer may be incremented to address any of the bytes 0 through 41 of the ASCLIM message. Next according to block 716, the value in location LCNT is set equal to 0 and according to block 718 the current hour in binary, is placed in the TIME location. It should be noted that an address of a table equal to the current hour refers to a table location containing information relating to the hour completed 24 hours ago. Next, according to block 720, the P.P.F for the patient for whom the trend history is to be printed is accessed.

Then, according to block 722, the address of the ECBHIS table is stored in the ECBADR word, the byte address of the last byte of the ECBHIS table is stored in the EOEBFR location, and the address of the time 24 hours ago is stored in the ECBAD word. This address is stored in byte format and may be determined by adding the value stored in TIME location last complete hour plus a count of 1 to the value stored in the ECBADR location and multiplying this sum by 2 to get the byte address.

Next, according to block 724, the patient number in ASCII code is placed in byte 29 of the MESSAGE table. Then, according to block 726 the message "TWENTY-FOUR HOUR ECTOPIC HISTORY BED__" is moved to the OUTBUF buffer. Then, according to block 728, the byte address of the last byte, plus 1, of the TIMBF table is stored in location EOTB, whereby location EOTB points to the byte following the end of the TIMBF table. Then, according to block 730, the address of the first byte of the LIM table is stored in location LIMAD, which location is a pointer to address a particular byte of the limit table LIM.

Next, according to block 732, the contents of the OUTBUF buffer is printed. It should be noted from block 726 that this message is "TWENTY-FOUR HOUR ECTOPIC HISTORY BED ". As previously explained, a reentrance code and the REENT address as the last four bytes of the OUTBUF causes the REENT program 738 to be scheduled for execution in its normal order so that REENT program 738 is executed after any other previously scheduled programs have been executed. This is indicated by block 734. Finally as indicated by block 736 a return to the executive program occurs.

Figure 16B:
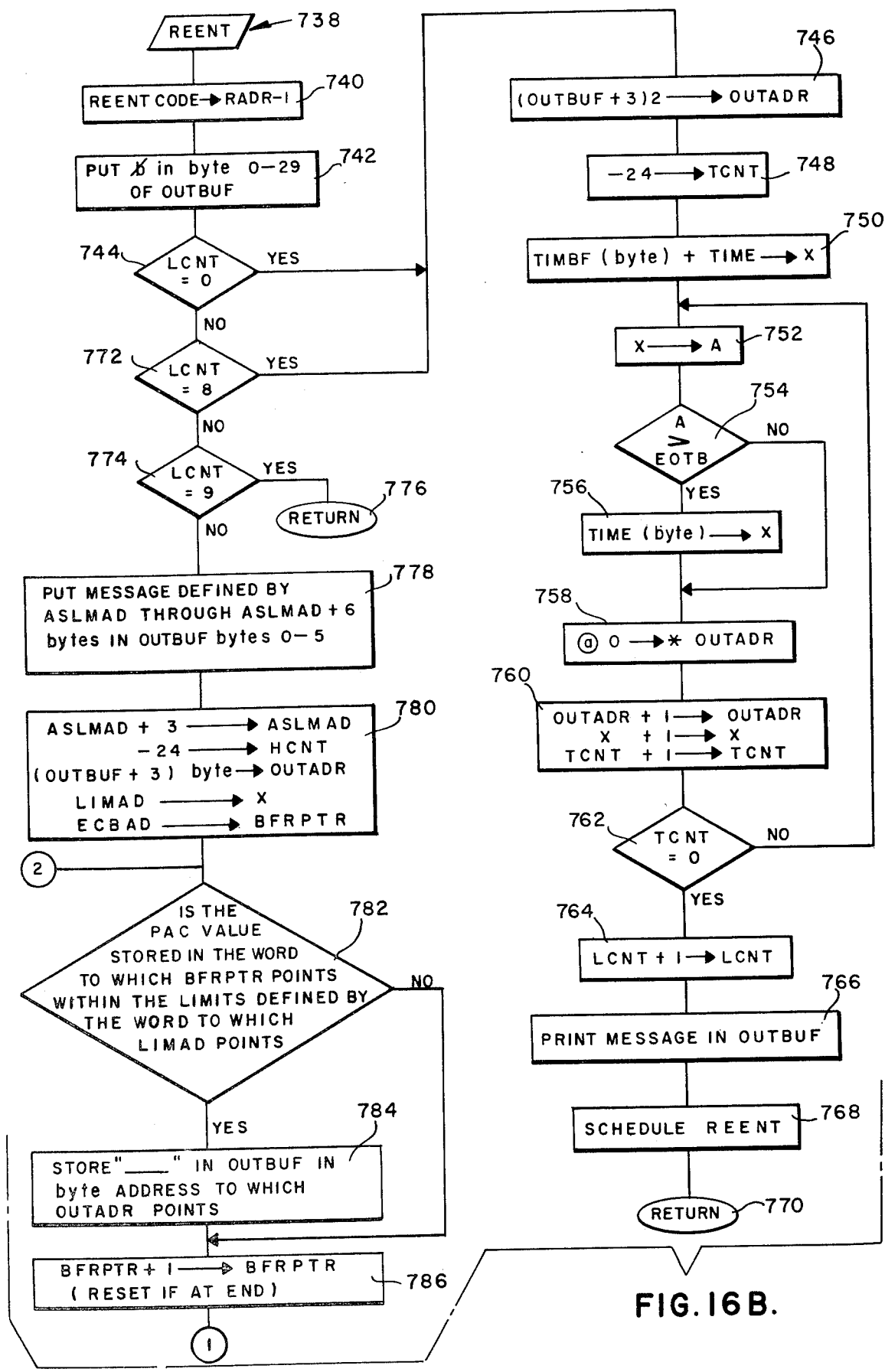
Figure 16C:
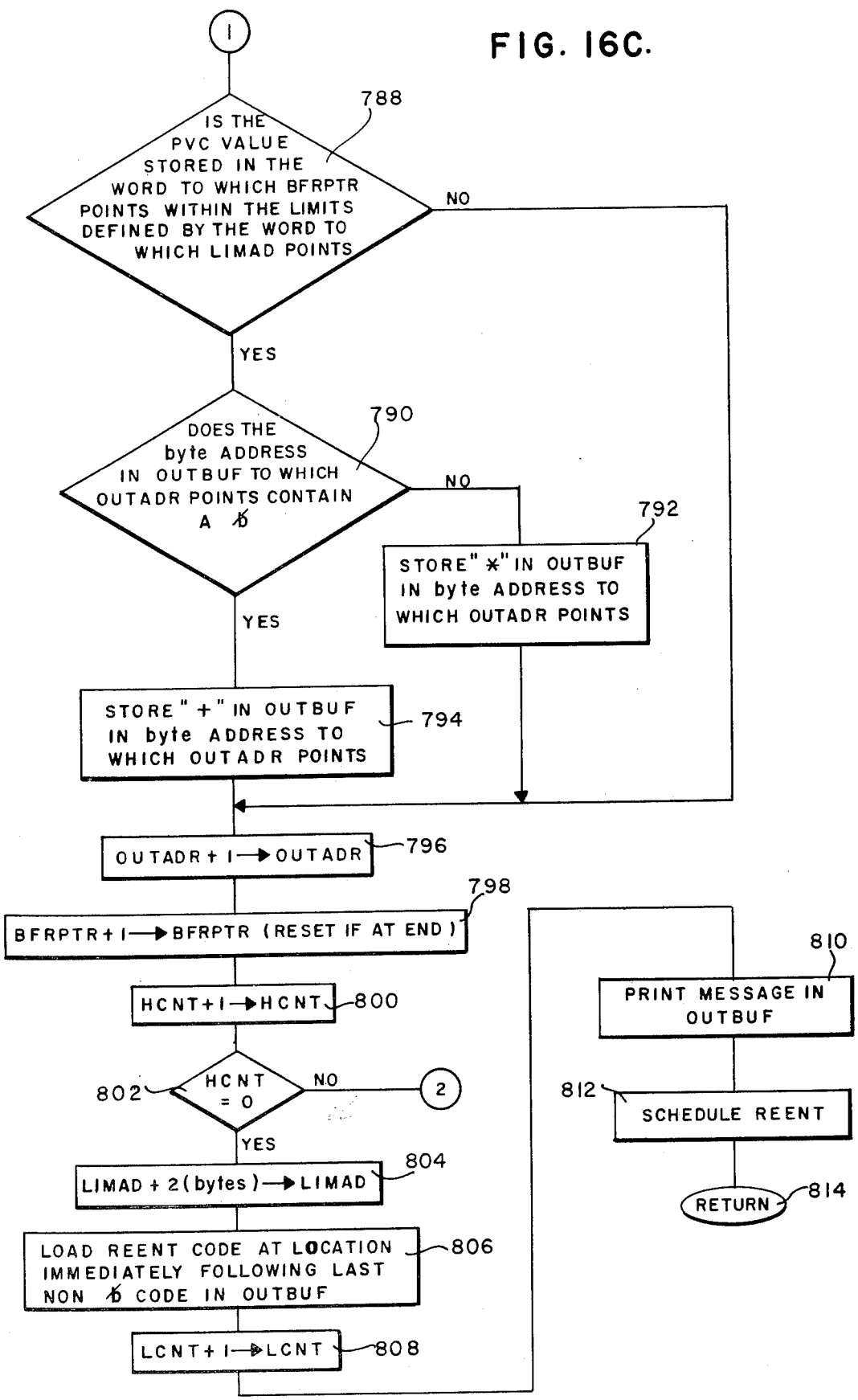

Referring now to FIGS. 16B and 16C, REENT program 738 will now be described. This program is scheduled for execution upon the completion of the execution of the REPORT program 710. The first occurrence in REENT program 738, as indicated by block 740, is that the REENT code is placed in address RADR −1 that is, in bytes 30 and 31 of the OUTBUF buffer. Next according to block 742, bytes 0 through 29 of the output buffer OUTBUF are filled with ASCII code for a blank.

It should be recalled at this point that at block 716 in REPORT program 710, a 0 was placed in the LCNT location. The LCNT location value is used to track which line of the histogram is being printed as previously mentioned, the top line (LCNT=0) and the bottom line (LCNT=8) are the message in the TIMBF table and the lines between (LCNT=1-7) are the data forming the histogram. Referring now to block 744, a determination is made of whether the value in LCNT location is equal to 0. If it is, a branch to block 746 occurs where the address of the OUTBUF buffer plus times two is loaded in the outbuffer pointer word OUTADR. Thus, the word OUTADR points to byte six in the OUTBUF buffer. Then according to block 748, a value of −24 is stored in location TCNT. Next according to block 750 the byte address of the beginning of the TIMBF table plus the value in the TIME location current hour is stored in the X register of computer 20 and according to block 752, this is transferred to the A register of computer 20. Then, according to block 754, a determination is made of whether the value in the A register is greater than the value of the EOTB word, which points to the last location, plus 1, of the TIMBF table, as previously explained with respect to block 728 in the REPORT program 710. If the determination at block 754 is that the value in the A register is greater than the EOTB value, then block 756 indicates that the byte address of TIMBF is stored in the X register. However, if it is determined at block 754 that the value in the A register is not greater than the value in the EOTB word, then block 756 is skipped and the value previously stored in the X register at block 750 remains therein because at block 752 when the value in the X register was transferred to the A register. Thus, in the event of a negative determination at block 754 or in the event of a transfer as indicated by block 756, the value in the X register will be the address of the completed hour 24 hours in the past, as indicated in the TIMBF table.

One of the capabilities of the particular computer 20 utilized in system 10 is that it is possible to operate on a word addressed by the values stored in the X register. This is symbolically noted by the sign "a" followed by a number. This means that the contents of the location of memory addressed by the value in the X register, plus the value of the number following "a" is to be operated upon. It is further possible with computer 20 to operate on a word having an address stored in another location. This is symbolically noted by a star "*" followed by a location definition. In this instance the word operated on is addressed by the contents of the location following the "*" rather than that word being the address. Thus, in block 758, the designation "@0→* OUTADR" means the contents of the word defined by the address stored in the X register is stored in a location of memory defined by the address stored in the word OUTADR. In other words the ASCII code for the dot, number or letter manifesting the time as addressed by the value TIMBF + TIME in the X register is transferred to byte location six in the OUTBUF buffer which byte location is pointed to by the word OUTADR, as discussed with respect to block 746. Thus, the dot, number or letter manifesting the hour 24 hours earlier is byte six of OUTBUF buffer.

Next according to block 760, the address in word OUTADR is incremented by 1, the value in the X register is incremented by 1, and the value of TCNT is incremented by 1. Thus, at this point, the value in OUTADR is the seventh byte of the OUTBUF buffer, the value in the X register is the address of the location of the hour 23-hours earlier, becomes −23.

At block 762, a determination is made whether the value of TCNT is equal to 0. Since it is not, a return to block 752 occurs and block 752, 754, 756, 758, 760, and 762 are repeated. At this time, ASCII code for a dot, number or letter manifesting the hour 23 hours earlier, as found from the TIMBF tables stored in the seventh byte address of the OUTBUF buffer and the value of TCNT is incremented −22. Then, a repetition of blocks 752 through 762 (even numbers only) got the hour 22 hours earlier is repeated. This continues until such time as the entire time message in TIMBF table is transferred to the OUTBUF buffer, which the hour 24 hours earlier to the SIXTH byte location thereof and the last completed hour in byte 29 of OUTBUF buffer.

At this point, the termination at block 762 indicates that the value in TCNT location is equal to 0. Then according to block 764, the value of LCNT is incremented by 1. Since it previously had been 0, it is now equal to a value of 1. Then, according to block 766, the message will be six blank spaces followed by dots, numbers, and the letters and in order manifesting the time 24 hours earlier until the most recent complete hour from left to right and will constitute the top line of the ectopic beat trend histogram.

Since the re-entrance code and REENT program 738 are included as the last two words of OUTBUF buffer message, then according to block 768 REENT program 738 is again scheduled for execution and, as indicated by block 770, a return to the executive program occurs.

When the REENT program 738 is again scheduled by the executive program, blocks 740 and 742 are repeated as previously described. The determination then at block 744 is now the value in location LCNT is not equal to 0 because it has been incremented to a count of one at block 764. In that event according to block 772, is made whether the value in location LCNT is equal to 8. This determination turns out to be negative. Then, at block 774, a determination is made whether the value at location LCNT is equal to 9. Again, this determination is negative.

Therefore, continuing with block 778, the message defined by the address in word ASLMAD to the address ASLMAD plus six bytes is placed in the output buffer. At this point, as previously discussed with respect to block 714, the address in the word ASLMAD is equal to byte zero of the ASCLIM table and the six bytes beginning with this address contain ASCII code for the message "17-UP", which code is placed in the first six bytes of the OUTBUF buffer, that is, in bytes 0 through 5 thereof. Next, according to block 780, the contents of the word ASLMAD is incremented by 3 and the value −24 is stored in the word HCNT. Further, the contents of word OUTADR is incremented by 3 to point to byte six of OUTBUF buffer. In addition, the value in word LIMAD is placed in the X register and the value in location ECBAD is placed in the word BFRPTR. As previously mentioned with respect to block 730, the value in word LIMAD is equal to byte zero of the LIM table and the value which was in word ECBAD, as indicated by block 722 is the address in ECBHIS table containing the PVC and PAC data for the hour 24 hours earlier.

Next, at block 782 a determination is made of whether the PAC value stored in the word of the ECBHIS table to which the contents of the word BFRPTR addresses is within the limits defined by byte zero and byte one of the LIM table to which the contents of the word LIMAD addresses. In other words, a determination is made of whether the number of PACs which occurred during the hour 24 hours earlier is 17 or more. If it is determined that the number of PACs which occurred during the hour earlier is 17 or more, then according to block 784, a minus sign (" ") is placed in the location of OUTBUF buffer in the byte address thereof to which the contents of the word OUTPT addresses, or in the sixth byte of the OUTBUF buffer. If the determination of block 782 had been that the number of PACs was not seventeen or greater than block 784 skipped, and a blank remains in byte six of OUTBUF buffer.

Next, according to block 786, the byte address pointing to ECBHIS table is incremented by 1 so that it points to the PVC value in the hour 24 hours earlier. If, at block 786, the value in BFRPTR location has been incremented to point past location EOEBFR, then it would have been reset to point to the PAC value in word 0 of the ECBHIS. Then, according to block 788, a determination is made whether the PVC value stored in the word which the BFRPTR pointer addresses is within the limits defined by the word which the LIMAD pointer addresses or in order words, whether 17 or more PVCs occurred during the hour which occurred 24 hours earlier. If it is determined that the number of PVCs occurring 24 hours earlier was greater or equal to seventeen then, according to block 790, a determination is made whether the byte address in the OUTBUF buffer which the word OUTADR addresses contains a code manifesting a blank space. If it contains a blank, then a plus sign ("+") is placed in that address of the OUTBUF buffer. However, if it had not contained the blank, it would have contained a minus due to the action at block 784 and, in this case, block 792 indicates that a star ("*") is placed in the byte address of the OUTBUF buffer which the OUTADR pointer address. If at block 788, a negative determination had been made, then blocks 790, 792 and 794 would have been skipped.

Thus, at this point, byte six in the OUTBUF buffer contains either a plus, a minus, a star or a blank value, depending on whether the number of PACs and PVCs which occurred during the hour which occurred 24 hours earlier exceeded a count of 17.

Next, according to block 796, the byte address stored in location OUTADR is incremented by one so that it points to byte seven of the OUTBUF buffer. Also, the word address in location BFRPTR pointing to the hour 24 hours earlier in ECBHIS table is incremented by 1 to point to the hour which occurred 23 hours earlier. If BFRPTR points to the end of ECBHIS table, it is reset to point to the first hour therein. Then, according to block 800, the value in location HCNT is incremented by one so that it is now −23. Next, according to block 802, a determination is made whether the value in location HCNT is equal to 0. If it is not equal to 0, a branch back to block 782 in FIG. 16B occurs and a determination is made whether the number of PACs which occurred during the hour 23 hours earlier is within the limit defined by the LIM table to which the LIMAD word then points. In other words, it is determined whether 17 or more PACs occurred during the complete hour 23 hours earlier. REENT program 738 continues in the same manner as described above through blocks 784, 786, 788, 790, 792, 794, 796, 798 and 800 for the PAC and PVC values which occurred 23 hours earlier. Then, according to block 802, a return to block 782 again occurs and the same procedure is repeated for the number of PACs and PVCs which occurred 22 hours earlier. This continues until such time as the value in location HCNT is incremented to 0. During this time, the number of all of the PACs and PVCs recorded in the ECBHIS table are compared against the limits seventeen and up and at the intersection of each hour and the "17-up" line either a blank, in a case the number of each is below 17, a plus, in the case the number of PVCs and PACs is 17 or greater will be stored in each of the byte addresses of the OUTBUF buffer.

At this point block 804 indicates that the byte address in the LIMAD is incremented by 2, to address the location in LIM table defined by bytes two and three, or in other words, to the limits 13 through 16. Then according to block 806, the re-entrance code is loaded in the OUTBUF buffer in the location, thereof following the last non-blank code therein. Thereafter according in block 808 the value of LCNT is incremented from a value of 1 to a value of 2. Then, according to block 810, the message in the output buffer is printed. This message will be the word "17-up" followed by a blank, a plus, a minus, or a star, depending upon whether the number of PVCs, or PACs, or both were greater than 17. Then, according to block 812, REENT program 738 is scheduled for execution by the executive program and according to block 814, a return to the executive program occurs.

When REENT program 738 is again executed the procedure above described again occurs with the exception that the OUTFUB buffer is loaded with the message "13-16" in bytes zero through five thereof and has a plus, a minus, a star or a blank in bytes six through 29 thereof depending upon whether or not the number of PVCs, PACs or both during a given hour fell within the limits defined by bytes two and three of LIM table, that is between the numbers 13 through 16. Again according to blocks 808 the value in LCNT location is incremented, this time to a value of 3, and the above procedure will again be repeated for the limits 9 through 12. Thereafter the procedure is repeated for the limits 6 through 8, the limits 4 through 5, the limits 2 through 3, and finally the limits 0 through 0, with in each case, a blank, plus, minus or star being inserted in the location of the OUTBUF buffer corresponding to the determined value of the number of the PVCs and PACs during a given hour. At this point, the value of LCNT at block 808 is incremented to a count of 8, and REENT program is again scheduled for execution at block 812. The above described printing of the blank, plus, minus and star characters results in a histogram showing the history of PVC and PAC activity during the preceeding 24 hours for the particular patient.

When REENT program 738 is again executed, the determination at block 772 will be that the value in LCNT is equal to eight and thus the previously described processes with respect to blocks 746 through 770 (even numbers only) is repeated and the time beginning with hour twenty-four hours earlier is printed below the blank, plus, minus, and stars histogram which previously have been printed while the LCNT value was between 1 and 7, inclusive. At block 764, the value of LCNT is incremented to 9, and at block 768 REENT program 738 is again scheduled for execution.

When REENT program 738 is again executed, the determination at block 774 will be that LCNT is equal to nine. In this instance, according to block 776, a return to the executive program occurs. It should be noted at this point that the REENT program 738 is not rescheduled. Thus, the entire ectopic beat trend history printout is complete and no further action is undertaken in response to the depression of the ECT TRND key on keyboard 38.

Figure 17A:
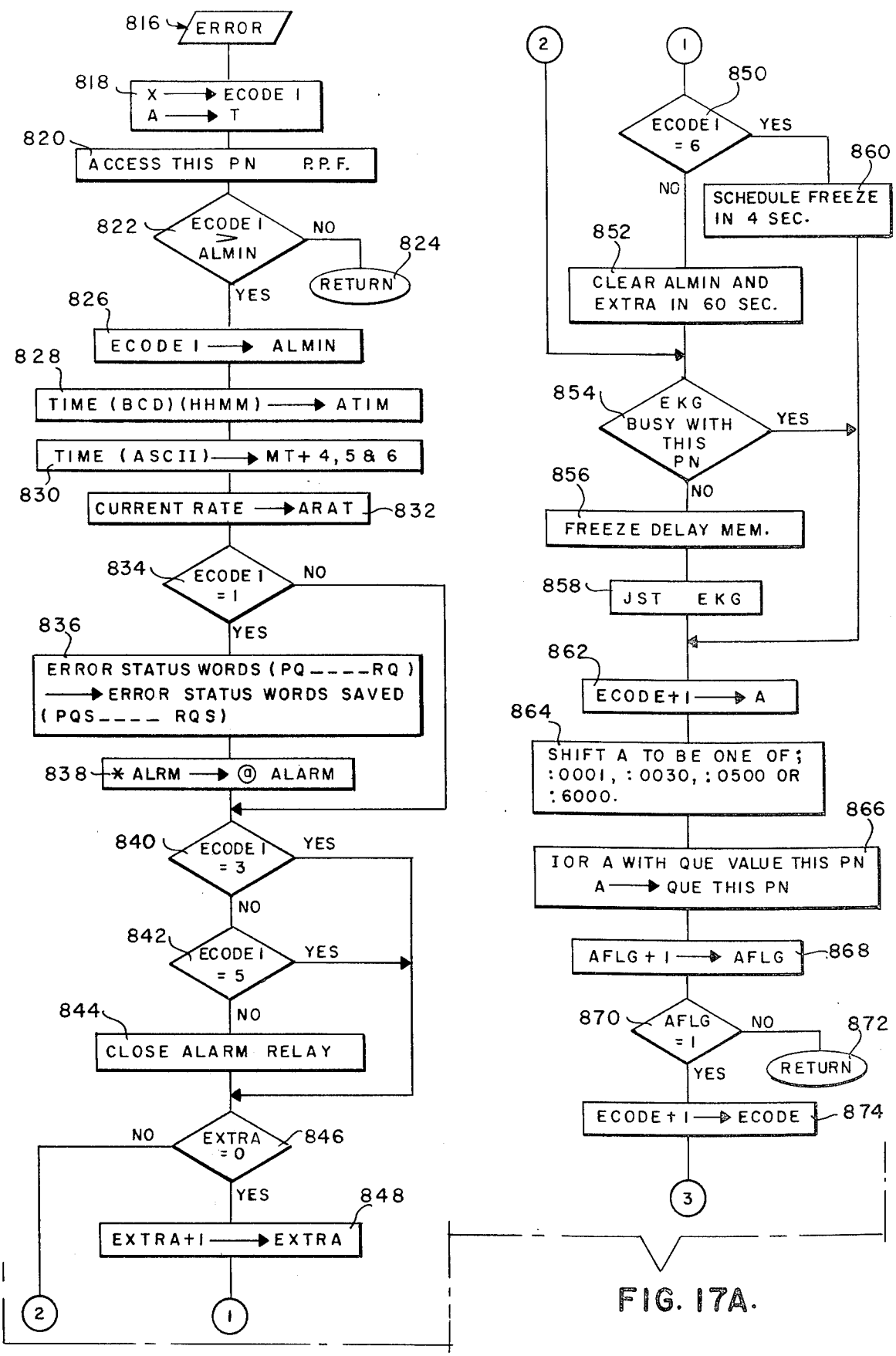
FIGS. 17A, 17B and 17C are a flow diagrams of a ERROR and RENT programs used to report various abnormalities occurring in a particular electrocardiac signal which are detected during the monitoring.
Figure 17B:
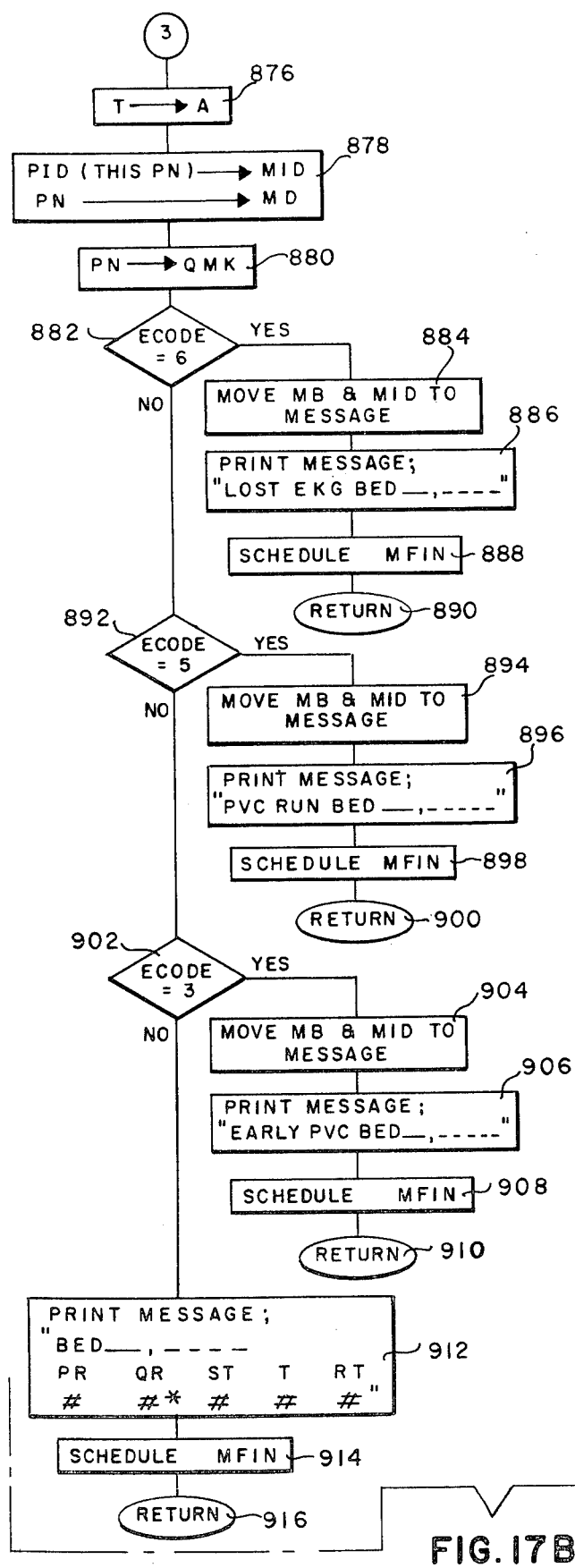
Figure 17B:
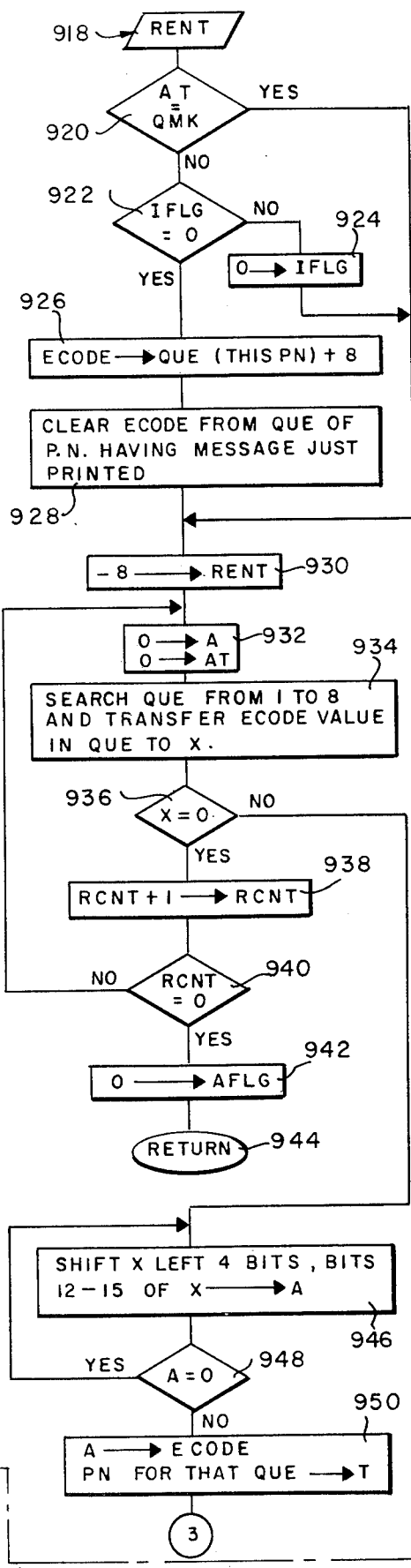
Figure 17C:
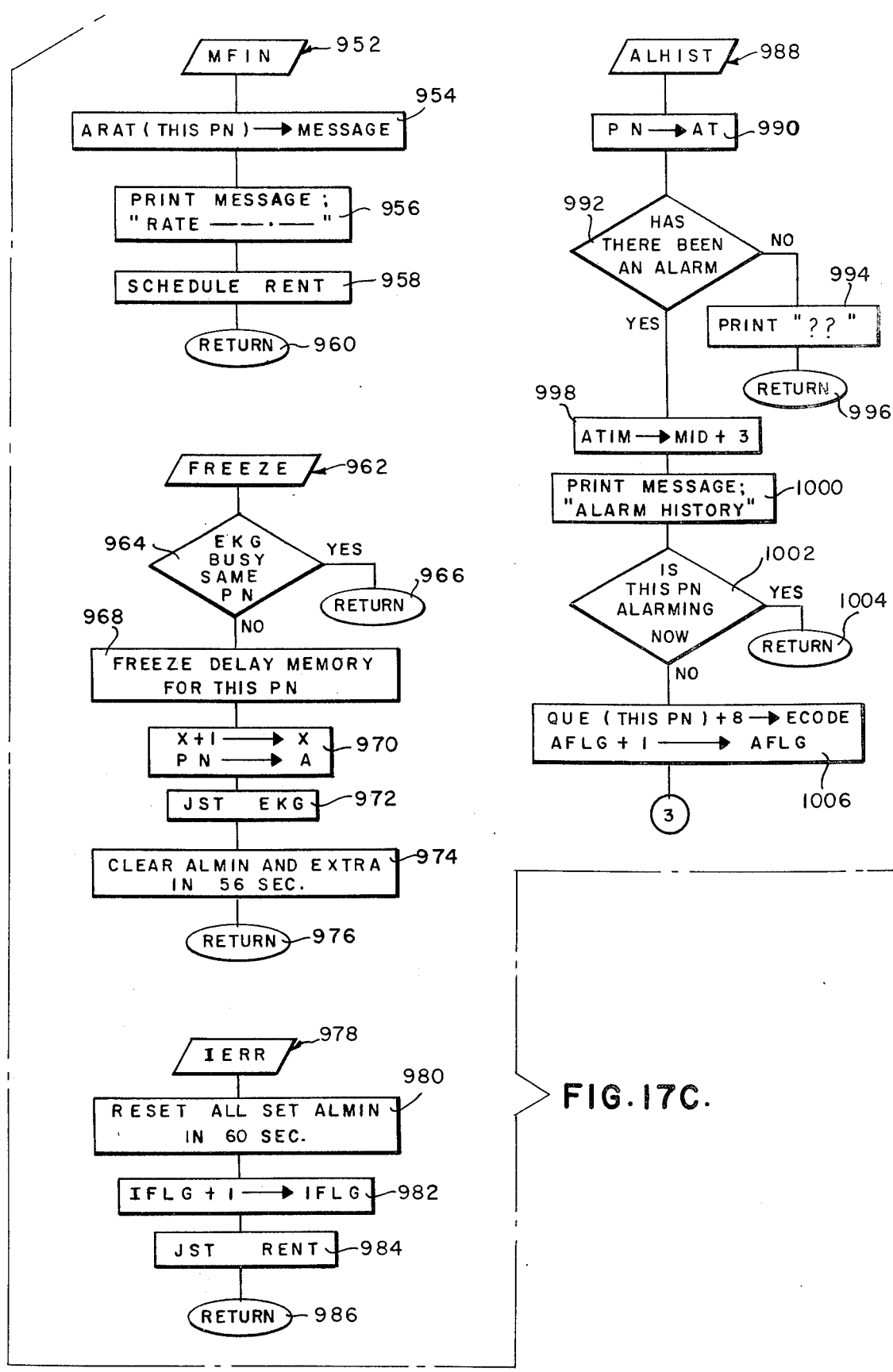

Referring now to FIGS. 17A, 17B and 17C, a description of ERROR program 816 will now be given. It should be recalled that ERROR program 816 is branched to during COPY program 400 in the event that a morphology or rate change beyond limits occurs also, it may be branched to during ECTO program 574 in the event of the detection of either an early PVC or a run of three or more PVCs. Finally it may be branched to during ARCHK program 88 in the event that a lost EKG situation is detected. Whenever ERROR program 816 is branched to, it is by a jump and store return instruction, the A register is loaded with the patient number having the error condition and the X register would be loaded with a priority code 1, 3, 5, or 6 respectively indicating a morphology or rate change, an early PVC a run of three PVCs, or a lost EKG situation can only control computer 20 to, in turn, control printer 36 to print one error at a time. However, ERROR PROGRAM 816 is capable of storing information relating to up to 32 different messages (four different error conditions for each of eight beds) so each can be printed as time permits. In addition, ERROR program 816 prints the message having the highest priority code therefore first, thereby giving a priority structure to the printing of a particular ERROR message. It should be noted from the manner in which the ERROR program 816 shown in FIG. 17A, 17B and 17C is configured that the priority is only partial in that it applies only to a particular bed number. The messages for the patients printed in order from patient one to patient eight; however, it is within the skill of the art to change the priority structure to print all highest priority messages first M order of first in, first out, or in any other priority structure desired.

ERROR program 816, includes blocks 818 through 916 has associated there with, but independent therefrom, REENT program 918, includes blocks 920 through 950 shown in FIG. 17B. In addition there are four programs shown in FIG. 17C which are also associated with ERROR program 816 and these include MFIN program 952, having blocks 954 through 960, FREEZE program 962, having blocks 964 through 976, IERR program 978 having blocks 980 through 986 and ALHIST program 988 having blocks 990 through 1,006.

Referring now specifically to ERROR program 816 block 818 indicates that the priority code in the X register of computer 20 is stored in location ECODE1 and the patient number in the A register of computer 20 is stored in location T. Then, according to block 820 the P.P.F. for the patient number in the A register of computer 20 is stored in location T. Then, according to block 820, the P.P.F. for the patient number in the A register of computer 20 is accessed. Next, according to block 882, a determination is made of whether the value stored in location ECODE1 is greater than the value in location ALMIN. If it is not greater, block 824 indicates a return to the executive program occurs. However, if the value in the location ECODE1 is greater than the value in location in ALMIN, then block 826 indicates that the value stored in location ECODE1 is stored in location ALMIN. It should be recalled that the value in location ECODE1 is the priority code for the particular event causing an error situation. The function of blocks 822, 824, and 826 is to serve to inhibit equal or lower priority alarms from occurring for a period of sixty seconds after the initial occurrence of an alarm but to allow higher priority, more severe alarms, to be printed during that 60 seconds. It should be noted that the starting point of the 60 seconds interval remains the same even though a more severe alarm occurs during the interval.

Next, according to block 828, the time in binary coded decimal (BCD) format indicating the hours and minutes is stored in location ATIM to indicate the time at which the last alarm occurred. According to block 830, this time is converted to ASCII format and then stored in locations MT+4 MT+5 and MT+6 of the message MT. Each of the locations MT+4 MT+5 and MT+6 may contain two digits in byte format with a colon separating the hours and minutes. According to block 832, the current rate, as computed during COPY program 400 at block 480, is then stored in location ARAT in the accessed P.P.F. for the alarming patient to indicate the heartbeat rate at the times of the alarm.

Next, according to block 834, a determination is made whether the value of the priority code in location ECODE1 is equal to 1. If it is equal to 1, thereby indicating either a morphology or rate error, then block 836 indicates that the error status words saved location PQS, QQS, SQS, TQS, and RQS in the accessed P.P.F. in order that the status of these words is not lost in the event that the error status words are further incremented if another QRS complex is detected prior to printing the message. Then, according to block 838, the value in the word ALRM, previously discussed with respect to block 474 and 490 in COPY program 400 is moved to the words ALARM in the accessed P.P.F. This information is used in printing the morphology and ratio error message.

If at block 834, it had been determined that the code in location ECODE1 had not been equal to 1, then blocks 836 and 838 would have been skipped. In any event, next according to block 840, a determination is made whether the values stored in location ECODE1 is equal to 3. If it is not equal to three, then according to block 842, a determination is made whether the value in location ECODE1 is equal to 5. If not, by process of elimination, the value in location ECODE1 must be equal to either 1 or 6, thereby indicating respectively a morphology or rate change or a lost EKG condition. For either of these events, according to block 844, the alarm rely in relay control circuit 26 is closed thereby connecting power to alarm 34 to cause it to emit an audible sound. Thus, alarm 34 is sounded whenever a rate or morphology change occurs, or whenever a lost EKG condition occurs. In the event of a early PVC or a run of PVCs, as detected by ECTO program 574, the bell on printer 36 is caused to sound either one or three times, respectively. As previously mentioned, in order to turn off alarm 34, it is necessary to depress the TONE OFF key on keyboard 38, and this merely causes the alarm relay to be opened. However, it should be noted, whenever an alarm, due to morphology or rate change or due to a lost EKG situation occurs, an operator response is necessary to turn off the alarm.

If it had been determined at block 840 or 842 that the value stored in location ECODE1 had been equal to either 3 or 5, then block 844 is skipped. In any event, next according to block 846, a determination is made whether the word EXTRA stored in the accessed P.P.F. is equal to 0. If it is equal to 0, then according to block 848, it is incremented by one.

Whenever, at block 846, the value in location EXTRA is determined to be equal to 0, it indicates that the alarm condition then occurring is the one which begins the 60 second alarm inhibit time. Thus, at block 848, it is necessary to increment the value in location EXTRA so subsequent and higher priority alarms do not restart the 60 second inhibit time. After incrementing the value in location EXTRA, it is necessary to direct the executive program to schedule that the ALMIN and EXTRA locations be cleared after the inhibit time.

Continuing with block 850, a determination is made whether the value stored in location ECODE1 is equal to 6. If it is determined that it is not equal to 6, then according to block 852, the ALMIN and the EXTRA location in the accessed P.P.F. are scheduled to be cleared in 60 seconds. If it had been determined at block 846 that the value in the EXTRA location had not been equal to 0, then blocks 848, 850 and 852 are skipped.

Next, according to block 854, a determination is made whether EKG strip chart recorder 30 is busy providing a strip recording for this patient. If it is not, then according to block 856, delay memory 50 for this patient is frozen and block 858 indicates that a jump and store return to the EKG program, shown in FIG. 18, occurred. The effect of freezing the delay memory in block 856 is to cause the EKG program, as will be hereinafter described, to provide a signal to EKG strip recorder 30 which shows the events preceeding causing the alarm, whether that event be in morphology or rate change, an early PVC, or a run of PVCs.

In order to freeze delay memory 50 for this particular patient, a signal is provided from computer 20 over line 52 to unit 44 to signal the delay memory portion 50 thereof to freeze the one of the eight shift registers therein which one is that associated with this particular patient having an alarm condition. Thus, whenever a signal is applied to EKG recorder 30, it will be the signal which occurs during the 8.3 seconds immediately preceeding the detection of the alarm. Therefore, the events leading to the alarm condition will be shown on the EKG recorder 30.

If at block 854 it had been determined that EKG recorder 30 was already busy providing the strip recording of this patient's signal, then blocks 856 and 858 are skipped in as much as that strip recording then in progress will show the alarm condition.

Referring again to block 850 if it had been determined that the value in location ECODE1 had been equal to 6, thereby indicating a lost EKG condition, then according to block 860, FREEZE program 962 shown in FIG. 17C, is scheduled to be performed in four seconds. Referring now to FIG. 17C and FREEZE program 962, first, according to block 964, a determination is made whether EKG recorder 30 is busy with this patient number. If it is, then block 966 indicates a return to ERROR program 816. However, assuming that EKG recorder 30 is not busy providing a strip recording for this patient, then according to block 968, the delay memory 50 for this patient is frozen. It should be noted that this occurs 4 seconds after the lost EKG condition was detected because FREEZE program 962 is not scheduled until 4 seconds after the detection is made. Thus, when the values in delay memory 50 for this patient are ultimately provided to the EKG recorder 30, it will provide a recording of the electrocardiac signal both before and after the detection of the lost EKG condition. Next, according to block 970, the X register of computer 20 is incremented and the patient number is stored in the A register of computer 20 and according to block 972, a jump and store return to the EKG program, shown in FIG. 18, occurs. After a return from the EKG program, block 974 indicates that the ALMIN and EXTRA words in the accessed P.P.F. are scheduled to be cleared in 56 seconds. This, together with the 4 second delay in executing FREEZE program 962, constitutes the same 60 seconds alarm inhibit involved with block 852 in ERROR program 816. Finally, according to block 976, a return to block 862 of ERROR program 816 occurs.

Continuing with block 862, the priority code value stored in location ECODE1 is then stored in the A register of computer 20 and, according to block 864, this value is shifted so that the A register will have an error code of one stored in bits 0 through 3 thereof, an error code of 3 stored in bits 4 through 7 thereof, an error code of 5 stored in bits 8 through 11 thereof, an error code of 6 stored in bits 12 through 15 thereof. Then, according to block 866, a logical inclusive OR function is performed between the A register and the value stored in a location or the error queue (QUE) included in ERROR program 816, and specifically with the value stored in the location of the error queue associated with this patient. The results of this inclusive OR function which remain in the A register, are then transferred to the location in the error queue for this patient.

The error queue associated with ERROR program 816 is 16 word table. The first half of the error QUE table, constituting eight words is used for storing the error codes to be printed and the last half of the error QUE, also constituting eight words, is used to store the last printed error code for each patient. With respect to the first half of the error queue, it is only used when printer 36 is unable to print an error message which is then occurring because it is busy printing another error message. It should be noted that in both the first half and the last half of the error queue, each of the respective eight words, the proof are associated with a respective one of the patients.

Next, according to block 868, the value in the location AFLG is then incremented by one and, according to block 870, a determination is made whether the value in the AFLG location is equal to 1. If the value in location AFLG is not equal to 1, thereby indicating at least one other error message is being printed or awaiting printing, then according to block 872, a return occurs to the executive program. The error just processed will subsequently be printed by use of the reentrance RENT program 918, to be hereafter discussed in detail. However, if at block 870, it had been determined that location AFLG contained a count of 1, thereby indicating that no other error messages except this particular message, is stored in the error queue and being printed d awaiting printing, then, according to block 870, the value in location ECODE1 is transferred to location ECODE.

Continuing in FIG. 17B with block 876, the patient number stored in location R is then transferred to the A register of computer 20 and according to block 878, this patient's identification number is transferred to the location MID in the message and the patient number in the A register is transferred to location MB in the message.

Then, according to block 880, the patient number in the A register is transferred to location QMK.

At block 882, a determiniation is made of whether the value in location ECODE is equal to 6. If the ECODE value is 6, then according to block 884, the patient ID and patient numbers from locations MID and MB are moved to the lost EKG message and the message

"LOST EKG BED__ , _____ "

is printed as indicated by block 886. Then, according to block 888, MFIN program 952 is scheduled for execution and according to block 890 a return to the executive program occurs. As will be understood in more detail hereafter, MFIN program 952 coops the ratio to be printed and RENT program 918 to be scheduled for execution.

If at block 882, it had been determined that the value in location ECODE was not equal to 6, then according to block 892, a determination is made whether the value in location ECODE is equal to 5. If equal to 5, then, according block 894, the patient ID and patient number stored in location MID and MD at block 878 are moved to the PVC run message. Then according to block 886, the message

"PVC RUN, BED __ , _____ "

is printed and according to block 898, MFIN program 952 is scheduled for execution. Then according to block 900 a return to the executive occurs.

If at block 892 it has been determined the value in ECODE location was not equal to 5, then, according to block 902, a determination is made whether the value in location ECODE is equal to 3. If equal to 3, then block 904 again indicates that the patient ID and patient number stored in locations MID and MB are moved to the early PVC message and, according to block 906, the message

"EARLY PVC BED __ , _____ "

is printed. Then according to block 908 the MFIN program 952 is scheduled for execution and according to block 910 a return to the executive program occurs.

If at block 902 it was determined ECODE was not equal to three, then by implication the value in location ECODE must equal to one and according to block 912, the following morphology and rate message is printed:

```
"BED __ ,__ __ __ __ __ __ __
 PR QR ST T RT
 #  #*  #  # #."
```

In this message, the notation "#" indicates that a number corresponding to the number of errors during the last 16 beats for that particular one of the contour intervals or rate is printed and the notation "*" indicates the one contour interval or rate which caused the alarm this information is obtained from the ALRM word transferred to location ALARM and from the error status words saved PQS, QQS, SQS, TQS and RQS.

Referring now to FIG. 17C MFIN program, which is scheduled for execution by one of blocks 888, 898, 908, or 914, will now be described. MFIN program 952 includes blocks 954 through 960. According to block 954, the values stored in ARAT location in the accessed P.P.F. is moved to the rate message. It should be recalled that the value stored in the ARAT location was the rate at the time the alarm condition occurred. Then, according to block 956, the message

"RATE ___ . ___ "

is printed. Then, according to block 958 the RENT program 918, shown in FIG. 17B, is scheduled for execution and according to block 960 a return to the executive program occurs.

Referring now to RENT program 918 in FIG. 17B, it includes blocks 920 through 950, from where a branch to block 876 in ERROR program 816 occurs. First, according to block 920, a determination is made whether the value stored in location AT is equal to the value stored in location QMK. It should be recalled from block 880 that the patient number of the patient having a message last printed is stored in location QMK. Locaton AT will have stored therein the patient number of a patient for which a message has just been printed in response to the ALARM HISTORY key on keyboard 38 being depressed. Thus, the determination at block 920 is whether the last message printed is due to an alarm history request rather than an error condition. Assuming that the determination at block 920 was that the previous message was due to an error condition, that AT is not equal to QMK, then, according to block 922 a determination is made whether the location IFLG is equal to 0. If IFLG is not 0, it indicates that GO program 64 is being executed due to a return of power and the jump and store return to IERR program 978 at block 74 in GO program 64 has occurred. If at block 922, it is determined that location IFLG is not equal to 0, then block 924 indicates that it is set equal to 0. However, if the value in location IFLG is 0, then, according to block 926, the value stored in location ECODE is stored in the second half of the error queue in the particular word thereof associated with the patient for whom the last alarm was printed. Then, according to block 928, the value stored in ECODE is cleared from the first half of the error queue in the particular word thereof associated with the patient for whom the last alarm was printed in order to prevent the same message from being again printed. It should be noted that only the particular ECODE value is cleared, not the entire word.

If at block 920, it had been determined that the value in locations AT and QMT were equal, then blocks 922, 924, 926 and 928 are skipped. Similarly, after block 924, blocks 926 and 928 are skipped. Thus, after an alarm history message, or after the first GO routine performance of RENT program 918, the error queue is not updated.

Next, according to block 930, locaton RCNT is set equal to minus eight and according to block 932, the A register in computer 20 and location AT are set equal to 0. Then, according to block 934, the upper half of the error queue is searched from locations one through eight. This may be accomplished by transferring first a location from the error QUE corresponding to patient one to the X register of computer 20. Then, according to block 936, a determination is made whether the register X is equal to 0. If it is determined that the X register is equal to 0, then according to block 938, the value in location RCNT is incremented and according to block 940, a determination is made whether the value in location RCNT is equal to 0. If not, a return to block 932 occurs and blocks 932, 934, 936, 938 and 940 are again performed for the next error queue location. This continues until the determination at block 936 indicates that the register does not contain a value equal to 0, or until the determination at block 940 indicates that the value in location RCNT is equal to 0. When the determination at block 940 is the value in location RCNT is equal to 0, then according to block 942, location AFLG is set equal to 0 and, according to block 944, a return to the executive program occurs. This indicates that no messages are presently in the error queue awaiting printing.

If at block 936 it is determined that the value in the X register is equal to 0, then, according to block 946 all of the bits in the X register are left shifted four bit position and the bits initially in bits position 12 through 15 in the X register are transferred to bits 0 through 4 of the A register. Then, according to block 948, a determination is made whether the A register is equal to zero. If the A register equals 0, a return to block 946 occurs and the next four bits in the X register are shifted into the A register. When the A register is not equal to 0 after four bits from the X register are shifted thereto, an error code previously stored in an error queue location will be stored in the A register. Accordingly, block 950 indicates that the value in the A register is loaded into location ECODE at the number of the error queue location having the non-zero value therein at block 936 and the patient number is loaded into location T. Thereafter, a jump to block 876 in ERROR program 816 occurs and the particular message corresponding to the value in location ECODE and the patient number in location T is printed. Thereafter, the MFIN program 952 is scheduled which as previously described, reschedules the RENT program 918 and the above described search of the error QUE is again repeated until such time as it is determined that no messages are stored in the error queue.

Referring again to FIG. 17C, and specifically to IERR program 978, which is branched to from block 74 of GO program 64, IERR program 978 consists of blocks 980, 982, 984, and 986. According to block 980, all of the ALMIN locations in the eight P.P.F.s are scheduled to be reset equal to 0 in 60 seconds. Then, according to block 982, the location IFLG is set equal to one and according to block 984, a jump and store return to the RENT program 918 occurs, this results in all of the messages in the error queue which were either stored therein or in the process of being printed at the time of the power failure to be printed in the manner previously described. After a return to JERR program 978, block 986 indicates a return to the executive program occurs. However, it should be noted that MAN program 952 will have been scheduled by this time, and this, in turn, will result in REENT program 918 being rescheduled until all of the messages in the error queue are printed.

Referring now to ALHIST program 988 in FIG. 17C, it consists of blocks 990 through 1,006 (even numbers only) from which a branch to block 876 in ERROR program 816 occurs. ALHIST program 988 is scheduled for execution whenever the ALRM HIST (alarm history) key on keyboard 38 is depressed. First, according to block 990, the patient number depressed on keyboard 38 is stored in location AT. Next, according to block 992, a determination is made whether there has been an alarm for this patient number. This may be simply looking at the location in the lower half of the error queue for this patient and determining whether it is 0. If it is determined at block 992 that no alarm has occurred for this patient, then according to block 994 two question marks are printed and, according to block 996, a return to the executive program occurs. If there had been an error printed for this patient, then, according to block 998, the time stored in locaton ATIM in the P.P.F. for this patient is transferred to locations MID+3 and, according to block 1,000, the message "ALARM HISTORY" is printed. Then, according to block 1,002, a determination is made whether this patient is then alarming. If so, then according to block 1,004 a return to the executive program occurs. If the patient is not then alarming, then according to block 1,006, the value stored in the lower half of the error queue for this patient, which indicates the last alarm, is transferred to location ECODE. Further, according to block 1,006, the value of AFLG is incremented by 1. Thereafter, a transfer to block 876 in ERROR program 816 occurs and the message indicated by the code in ECODE location is then printed in the manner previously described.

Referring now to FIG. 18, EKG program 1,008 will now be described. This program consists of block 1,010 through 1,030 (even numbers only). EKG programs 1,008 further has associated therewith MARK program 1,032 which consists of blocks 1034 through 1056 (even numbers only) and FIN program 1,058 which includes blocks 1,060 through 1,088 (even numbers only). In addition, MROFF program 1,090 consisting of blocks 1,092 and 1,094 is also shown in FIG. 18, and, it should be recalled, MROFF program 1,090 is jumped to from block 202 in ACQ program 192 to turn off the marker relay. This occurs according to block 1092 and then according to block 1094 a return to block 204 in ACQ program 192 is indicated.

Referring specifically to EKG program 1,008 any jump thereto will occur with the A register of computer 20 containing the patient number of the patient to whom the EKG strip recording is to relate and the X register of computer 20 containing either a positive value in the event of a delayed strip, or the information contained in the delay memory, is to be printed on the EKG strip or with the X register containing a zero in the event a real time strip, or the information applied as signals PN1 through PN8, is to be printed on the EKG strip. First, according to block 1,100, a determination is made whether EKG strip chart recorder 30 is busy. If it is, then, according to block 1,112, the value in the X register is stored in the EKG queue for this patient number. The EKG queue is an eight word table with one word of the table being assigned to each of the eight patient numbers. Then according to block 1,114, a return to the program causing the branch to EKG program 1,008 occurs.

If it has been determined at block 1,100 that the EKG recorder 30 was not busy, then, according to block 1,116, the code in the X register is transferred to location ECODE in EKG, program 1,008 and the patient number in the A register is transferred to the EKGBSY location. The value in the EKGBSY location indicates that EKG recorder 30 is busy providing an electrocardiograph strip record for that particular patient number and is the location checked at block 1,010. Next, according to block 1,118, the PN signal for this patient is connected to cardioscope 32 by sending the appropriate signal from computer 20 through line 28 to relay control circuit 26 to connect the PN signal through relay control circuit 26 to scope 32. Next, according to block 1,020, a determination is made whether the value in ECODE location is equal to 0. If not 0, then according to block 1022, delay memory 50 for the patient number in EKGBSY location is unfrozen and connected to the EKG recorder 30. This causes the delayed signal scored in the delay memory 50 for this patient to be printed by EKG recorder 30 and in this manner, the "event" leading up to the error condition manifested by the delayed signal becomes apparent to the operator. If at block 1020, it had been determined that the value in location ECODE was equal to 0, then according to block 1024, the one of the real time signals PN1 through PN8 for this patient is connected to EKG recorder 30 and a real time strip chart recording by EKG recorder 30 occurs. In either event, according to block 1025, EKG recorder 30 is turned on and then, according to block 1028, the executive program is directed to schedule FIN program 1058 for execution in 8.3 seconds to turn off recorder 30 under normal circumstances. In addition, the executive program is directed to schedule MARK program 1,032 for execution in 6.3 seconds to turn on the marker a number of times equal to the patient number during the last 2 seconds of the strip. Thereafter, according to block 1,030 a return occurs to the program from which EKG program 1,008 was branch when MARK program 1,032 is executed 6.3 seconds after EKG program 1,008 is completed, first, according to block 1,034 EKG recorder 30 is checked to determine if it is still busy with the same patient. If it is not, then a return to the executive program is indicated by block 1,036. This could occur if, for instance, the EKG OFF key on keyboard 38 is depressed prior to the expiration of the 6.3 seconds. Assuming EKG recorder 30 is still busy with the same patient number, then, according to block 1,038, the negative of the sum of the patient number plus 1, is stored in the MCNT location. Then, according to block 1,040, a determination is again made whether EKG recorder 30 is still busy with the same patient number. If not, block 1,042 indicates a return to the executive program occurs. Assuming again that EKG recorder 30 is still busy with the same patient number, then, according to block 1,044 the value in locaion MCNT is incremented by one. Then, according to block 1,046, a determination is made whether location MCNT is equal to 0. If it is, block 1,048 indicates a return to the executive program occurs. If MCNT is not equal to 0, then, according to block 1,050, the marker is turned on and according to block 1,052 a count of $-8$ is stored in location MRFTRG in ACQ program 192. As previously explained with respects to blocks 196, 198, 200, and 202, in ACQ program 192, MRFTRG location is incremented to zero by block 198 every 120th of a second until such time as MRFTRG is determined to be equal to 0 at block 200, at which time program MROFF 1,090 is executed to turn the marker off. Thereafter, as indicated by block 1,054, M1 program 1055 is scheduled for execution in 0.2 seconds and, according to block 1,056, a return to the executive program occurs. M1 program 1,055, when scheduled 0.2 seconds later, begins with block 1,040 in MARK program 1,032 and turns the marker on again as long as the value in MCNT is not equal to 0. Thus, for patient number 1 the marker will be turned on one time. For patient number 2 the marker will be turned on two times and so forth until for patient number 8, the marker is turned on eight times. In this manner the particular strip provided by EKG recorder 30 can be associated with a patient by counting the number of marks thereon. It should be noted that once it is determined that MCNT equals 0 at block 1,046, a return to the executive program occurs as indicated by block 1,048, prior to the time M1 program 1055 is rescheduled at block 1,054. Thus, MARK program 1,032 turns itself off after providing the proper number of marks on the strip record.

Referring now to FIN program 1,058 which is scheduled 8.3 seconds after the EKG program 1,080 has been scheduled, block 1,060 indicates that first the delay memory 50 signal is disconnected from EKG recorder 30, if it had been connected. Then, according to block 1,062, a determination is made whether EKG recorder 30 is busy with this patient number. If it is not, then, according to block 1,064, a return to the executive program occurs. Assuming EKG recorder 30 is still busy with this patient number, then, according to block 1,066, the X register in computer 20 is cleared and the patient number stored in location EKGBSY is transferred to the A register in computer 20.

Then according to block 1,068, a determination is made whether the value in location LONG is equal to the value in location EKGBSY. The value in location LONG will be 0 unless the STRIP button on keyboard 38 had been depressed followed by a particular patient number. In this event, the particular patient's number would be stored in the LONG location. It should be recalled that the depression of the STRIP button on keyboard 38 indicates a continuous EKG strip as desired. If at block 1,068 the values in the LONG and EKGBSY locations had been the same, then a branch to block 1,016 in EKG program 1,008 occurs and the EKG recorder 30 remains on.

However, if at block 1,068, the values in locations LONG and EKGBSY had not been equal, then according to block 1,070, the value $-1$ is stored in the EKG queue location for this patient. Then, according to block 1,072 the EKGBSY flag is cleared, that is, set equal to 0. Then, according to block 1,074, the real time signal is disconnected from the EKG recorder 30, if corrected. Thus, no signal will be applied to EKG recorder 30 at this point, so, according to block 1,076, EKG recorder 30 is turned off. Then, according to block 1,078, the value in LONG location is transferred to the A register and the X register is cleared. At this point, as indicated by block 1,080, a determination is made whether the value in location LONG is equal to 0. If it is not, then a branch back to block 1,016 and EKG program 1,008 occurs and the EKG recorder 30 is turned on for the patient number whose value is stored in LONG location in the manner previously described. If at block 1,080, the value in the LONG location had been equal to zero, then, according to block 1,082, a search of the EKG queue is made. If a value is stored in one of the locations of the EKG queue, as indicated by the determination at block 1,084, then, according to block 1,086, the value stored therein is transferred to the A register and the number of that location of the EKG queue is transferred to the X register which number corresponds of the patient number. Thereafter, a branch to block 1,016 in EKG program 1,008 occurs and EKG recorder 30 is turned on for that particular patient. If no values are stored in the EKG queue, as determined at block 1,084, then, according to block 1,088, a return to the executive program occurs.

Referring now to FIG. 19, DROP program 1096 is shown, which includes blocks 1,098 through 1,106 (even numbers only). This program is executed in a response to the depression of the DROP key on keyboard 38, followed by a patient number and the ENTER key. According to block 1,098, it is first determined whether this patient is being acquired. If so, then the ACQPN location is cleared, which location is used to indicate the patient is being acquired. If the patient is not being acquired, then block 1100 is skipped. Next according to block 1102 the P.P.F. for this patient is cleared and according to block 1104 the following message is printed:

"DROPPING __, _____
HH MM SS MONTH DAY YEAR"

In this message, the second line is the time and date. Finally, according to block 1106, a return to the executive program occurs.

Referring now to FIG. 20 SHOW program 1,108 is shown and consists of blocks 1,110 through 1,120 (even numbers only). SHOW program 1,108 is executed in response to the depression of the SHOW key followed by a patient number key and ENTER key on keyboard 38. First, according to block 1,110, a determination is made whether the EKG recorder 30 is busy. If it is, then according to block 1,112, printer 36 prints the message WAIT and, according to block 1,114, a return to the executive occurs. If the EKG recorder 30 was not busy as determined at 1,110, then, according to block 1,116 the PN signal corresponding to the patient requested is connected to cardioscope 32 by computer 20 applying a proper signal over line 28 to relay control circuit 26. Then, according to block 1,118, printer 36 prints the message " ON SCOPE". Finally, according to block 1,120 a return to the executive program occurs.

Referring now to FIG. 21, SUSP program 1,122 is shown and consists of blocks 1,124 through 1,132 (even numbers only). SUSP program 1,122 is called in response to the depression of the SUSP key followed by a patient number key and the ENTER key on keyboard 38. The first thing which occurs, as indicated by block 1,124, is that a determination is made whether this patient is being acquired. If that patient is being acquired then, according to block 1,126, printer 36 prints two question marks and, according to block 1,128, a return to the executive program occurs. However, is that patient is not being acquired, then according to block 1,130, a zero is transferred to the ST location in that patient's P.P.F. and according to block 1,132 a return to the executive occurs.

Referring now to FIG. 22, PVCSET program 1,134 is shown and includes blocks 1,136 and 1,138. This program is executed in response to the depression of a ECT RSET (eitopic history reset) key on keyboard 38, followed by a patient number key and ENTER key. As indicated by block 1,136, the PVC1, PVC2, PVCM, PAC1, PAC2, PACM, PVCAVG locations are all set equal to zero, and then, according to block 1,138, a return to the executive program occurs.

Referring now to FIG. 23, RSET program 1,140 is shown and includes blocks 1,142, 1,144, and 1,146. RSET program 1,140 is executed and a response to the depressions of the RHST RSET (rate history reset) key, followed by a patient number key and ENTER key on keyboard 38. First, according to block 1,142, the maximum positive value is placed in location LOHIST and the maximum negative value is placed in location HIHIST, Then, according to block 1,144, the current time is placed in location LOTIM, HITIM, and RTIM. Then, according to block 1,146, a return to executive program 48 occurs.

Referring now to FIG. 24, RATE program 1,148 is shown and consists of blocks 1,150 through 1,162 (even numbers only). This program is executed in response to the depression of the RATE HIST key followed by a patient number key and ENTER key on keyboard 38. First, according to block 1,150, this patient's P.P.F. is accessed and, according to block 1,152, a determination is made whether location REJECT is equal to 0, to indicate a suspension. If location REJECT is not equal to 0, then according to block 1,156, printer 36 prints two question marks, and according to block 1,158, a return to the executive program occurs. However, if at block 1,152, it is determined that the value in location ST is equal to 5, or if at block 1,154 it is determined that the value in locaton REJECT is equal to 0, then the following value from the P.P.F. are transferred to the message, as indicated by block 1,160: PID, RTIM, PVCTIM, HITIM, LOTIM, HIHIST, LOHIST, TRR CRR PN, PVC1, PVC2, PVCM, PAC1, PAC2, PACM, PVCAVG, and PVCAVG. Then, as indicated by block 1,162, the following message is printed:

| BED __ | | TIME |
|---|---|---|
| ORIGINAL | __ __ . __ | |
| CURRENT | __ __ . __ | |
| MAXIMUM | __ __ . __ | __ __ . __ |
| MINIMUM | __ __ . __ | __ __ . __ |
| TIME SET | __ __ . __ | |

Finally, as indicated by block, 1,164, a return to the executive program occurs.

What is claimed is:

1. In an electrocardiac monitoring apparatus including means for generating limits for signals indicative of parameters which are functions of an electrocardiac waveform and means indicating an error condition when sampled signals of subsequently measured waveforms indicate measured parameters outside of the limits, the improvement for reporting error conditions comprising: utilization means for displaying a selected error message uniquely corresponding to an error code signal, computer means for producing error code signals in response to and uniquely corresponding to a type of error condition, storage means for storing a current error code signal, and means connected to said utilization means for causing said utilization means to provide an error message corresponding to the current error code signal, further means in said storage means for storing error code signals during provision of the error message in said computer means for clearing the current error code signal and providing to said storage means a next error code signal in the position of said current error code signal, whereby said utilization means may provide error messages indicative of all error code signals.

2. The improvement according to claim 1 wherein said utilization means is a printer.

3. The improvement according to claim 1 or claim 2 wherein each unique error code includes a priority code and wherein said computer means provides error code signals to said storage means in order in correspondence with priority assigned thereto.

4. The improvement according to claim 3 wherein said electrocardiac monitoring apparatus comprises means for providing error signals indicative of error conditions of lost EKG, PVC run, EARLY PVC, and parametric error and wherein said computer means generates priority codes in error code signals corresponding to said error conditions respectively as most important to least important.

5. A method for practice on an electrocardiac monitoring apparatus which comprises means for measuring parameters associated with electrocardiac waveforms and responding to error conditions associated with each parameter when monitored signals are measured outside of predetermined limits with respect to each parameter, the method comprising: generating an error code signal uniquely corresponding to a type of error condition, storing each error code signal in storage means, periodically interrogating the storage means for error code signals, accessing individually an error code signal stored in said storage means, producing a further signal indicating the presence of an error code signal, operating utilization means in response to the further signal to provide a message indicative of the error condition, storing any subsequently produced error code signal while said utilization means is being operated and repeating the steps of accessing for any further stored error code signals and operating said utilization means in response thereto.

6. The method of claim 5 wherein the step of generating a unique error code signal comprises assigning a priority corresponding to each type of error condition and wherein the step of accessing said error codes comprises accessing in order in correspondence with their priority.

* * * * *